United States Patent
Roth et al.

(10) Patent No.: US 6,794,395 B1
(45) Date of Patent: Sep. 21, 2004

(54) SUBSTITUTED INDOLINONES, THEIR MANUFACTURE AND THEIR USE AS MEDICAMENTS

(75) Inventors: Gerald Juergen Roth, Biberach (DE); Armin Heckel, Biberach (DE); Rainer Walter, Biberach (DE); Ulrike Tontsch-Grunt, Baden (AT); Walter Spevak, Oberrohrbach (AT); Jacobus C. A. Van Meel, Moedling (AT)

(73) Assignee: Boehringer Ingelheim Pharma GmbH & Co. KG, Ingelheim (DE)

( * ) Notice: Subject to any disclaimer, the term of this patent is extended or adjusted under 35 U.S.C. 154(b) by 0 days.

(21) Appl. No.: 10/069,557

(22) PCT Filed: Aug. 22, 2000

(86) PCT No.: PCT/EP00/08149
§ 371 (c)(1),
(2), (4) Date: Jul. 22, 2002

(87) PCT Pub. No.: WO01/16130
PCT Pub. Date: Mar. 8, 2001

(30) Foreign Application Priority Data

Aug. 27, 1999 (DE) .......................................... 199 40 829
Jun. 14, 2000 (DE) .......................................... 100 29 285

(51) Int. Cl.$^7$ .................. A61K 31/404; A61K 31/454; C07D 209/34; C07D 401/08
(52) U.S. Cl. ...................... 514/323; 514/418; 546/201; 548/486
(58) Field of Search ................. 514/418, 323; 548/486; 546/201

(56) References Cited

FOREIGN PATENT DOCUMENTS

| DE | 198 150 20 | 10/1999 |
| DE | 198 166 24 | 10/1999 |
| WO | WO 99/15500 | 4/1999 |

OTHER PUBLICATIONS

STN International ® Database, Accession No. 1981:603820; Pavlenko et al., Khimiya Geterotsiklicheskikh Soedinenii (1981), (8), 1088–93.*
International Search Report, Oct. 25, 2000.

* cited by examiner

Primary Examiner—Taofiq Solola
(74) Attorney, Agent, or Firm—Robert P. Raymond; Anthony P. Bottino; Timothy X. Witkowski

(57) ABSTRACT

The present invention relates to substituted indolinones of general formula

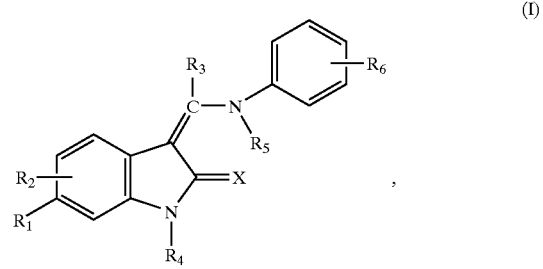

wherein $R_1$ to $R_6$ and X are defined as in claim 1, the isomers and the salts thereof, in particular the physiologically acceptable salts thereof which have valuable pharmacological properties, especially an inhibitory effect on various receptor-tyrosine kinases, and cycline/CDK complexes as well as on the proliferation of endothelial cells and various tumor cells, pharmaceutical compositions containing these compounds, their use and processes for preparing them.

8 Claims, No Drawings

SUBSTITUTED INDOLINONES, THEIR MANUFACTURE AND THEIR USE AS MEDICAMENTS

This application is a 35 USC § 371 case of PCT EP 00/08149 which in turn claims priority to German cases DE 199 40 829.7 filed Aug. 27, 1999 and 100 29 285.2 filed Jun. 14, 2000.

The present invention relates to new substituted indolinones of general formula

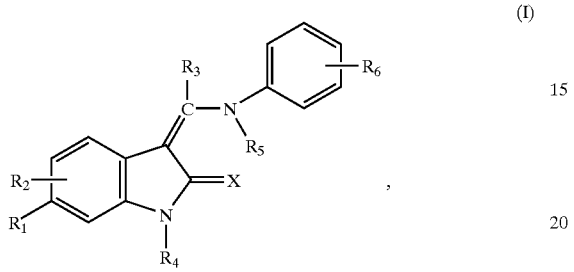

(I)

the isomers thereof, the salts thereof, particularly the physiologically acceptable salts thereof which have valuable properties.

The above compounds of general formula I wherein $R_4$ denotes a hydrogen atom or a prodrug group have valuable pharmacological properties, in particular an inhibiting effect on various kinases, especially receptor tyrosine kinases such as VEGFR2, PDGFRα, PDGFRβ, FGFR1, FGFR3, EGFR, HER2, IGF1R and HGFR, as well as complexes of CDK's (Cycline Dependent Kinases) such as CDK1, CDK2, CDK3, CDK4, CDK5, CDK6, CDK7, CDK8 and CDK9 with their specific cyclines (A, B1, B2, C, D1, D2, D3, E, F, G1, G2, H, I and K) and to viral cycline (cf. L. Mengtao in J. Virology 71 (3), 1984–1991 (1997)), to the proliferation of cultivated human cells, in particular endothelial cells, e.g. in angiogenesis, but also to the proliferation of other cells, in particular tumour cells.

The other compounds of the above general formula I wherein $R_4$ does not denote a hydrogen atom or a prodrug group are valuable intermediate products for preparing the abovementioned compounds.

The present invention thus relates to the above compounds of general formula I, whilst those compounds wherein $R_4$ denotes a hydrogen atom or a prodrug group have valuable pharmacological properties, pharmaceutical compositions containing the pharmacologically active compounds, the use thereof and processes for preparing them.

In the above general formula I

X denotes an oxygen or sulphur atom, $R_1$ denotes a $C_{2-3}$-alkenyl, $C_{2-3}$-alkynyl, aryl, aryl-$C_{1-3}$-alkyl, heteroaryl, heteroaryl-$C_{1-3}$-alkyl, trifluoromethyl or cyano group, a hydroxy, $C_{1-3}$-alkoxy, hydroxy-$C_{1-3}$-alkyl, $C_{1-3}$-alkoxy-$C_{1-3}$-alkyl, aryloxy or heteroaryloxy group, a mercapto, $C_{1-3}$-alkylsulphenyl, phenylsulphenyl, benzylsulphenyl, $C_{1-3}$-alkylsulphinyl, phenylsulphinyl, benzylsulphinyl, $C_{1-3}$-alkylsulphonyl, phenylsulphonyl, benzylsulphonyl, sulpho, $C_{1-3}$-alkoxysulphonyl, phenoxysulphonyl or benzyloxysulphonyl group, an amino, $C_{1-3}$-alkylamino, di-($C_{1-3}$-alkyl)-amino, hydroxycarbonyl-$C_{1-3}$-alkylamino, N—($C_{1-3}$-alkyl)-hydroxycarbonyl-$C_{1-3}$-alkylamino, $C_{1-3}$-alkoxycarbonyl-$C_{1-3}$-alkylamino, N—($C_{1-3}$-alkyl)-$C_{1-3}$-alkoxycarbonyl-$C_{1-3}$-alkylamino, phenylamino, N-phenyl-$C_{1-3}$-alkylamino, N,N-diphenylamino, benzylamino, N-benzyl-$C_{1-3}$-alkylamino, N,N-dibenzylamino, $C_{1-3}$-alkylcarbonylamino, benzoylamino or benzylcarbonylamino group or an N—($C_{1-3}$-alkyl)-$C_{1-3}$-alkylcarbonylamino group wherein the two alkyl groups may be replaced by a $C_{2-5}$-n-alkylene bridge or wherein one or both alkyl groups may be replaced by a phenyl or benzyl group, a $C_{1-3}$-alkylsulphonylamino, phenylsulphonylamino or benzylsulphonylamino group or an N—($C_{1-3}$-alkyl)-$C_{1-3}$-alkylsulphonylamino group wherein the two alkyl groups may be replaced by a $C_{2-5}$-n-alkylene bridge or wherein one or both alkyl groups may be replaced by a phenyl or benzyl group, an aminosulphonyl, $C_{1-3}$-alkylaminosulphonyl, phenylaminosulphonyl, benzylaminosulphonyl, di-($C_{1-3}$-alkyl)-aminosulphonyl, oN,N-diphenyl-aminosulphonyl or N,N-dibenzyl-aminosulphonyl group, a phosphono, ($C_{1-3}$-alkoxy)PO(H), ($C_{1-3}$-alkoxy)PO ($C_{1-3}$-alkyl), ($C_{1-3}$-alkoxy)PO(OH), di-($C_{1-3}$-alkoxy)-PO or ($C_{2-4}$-n-alkylenedioxy)-PO group, a ureido group optionally mono-, di- or trisubstituted by $C_{1-3}$-alkyl groups, a 4- to 7-membered cycloalkyleneimino or cycloalkyleneiminosulphonyl group, wherein in each case the methylene group in the 4 position of a 6- or 7-membered cycloalkyleneimino group may be replaced by an oxygen or sulphur atom, by a sulphinyl, sulphonyl, —NH or —N($C_{1-3}$-alkyl) group, $R_2$ denotes a hydrogen, fluorine, chlorine, bromine or iodine atom, a $C_{1-6}$-alkyl or trifluoromethyl group, a hydroxy, $C_{1-3}$-alkoxy, mercapto, $C_{1-3}$-alkylsulphenyl, $C_{1-3}$-alkylsulphinyl, $C_{1-3}$-alkylsulphonyl, sulpho, $C_{1-3}$-alkoxysulphonyl, aminosulphonyl, $C_{1-3}$-alkylaminosulphonyl or di-($C_{1-3}$-alkyl)-aminosulphonyl group, a nitro, amino, $C_{1-3}$-alkylamino or di-($C_{1-3}$-alkyl)-amino group, a $C_{1-3}$-alkylcarbonyl, cyano, carboxy, $C_{1-3}$-alkoxycarbonyl, aminocarbonyl, $C_{1-3}$-alkylaminocarbonyl or di-($C_{1-3}$-alkyl)-aminocarbonyl group, a phosphono, ($C_{1-3}$-alkoxy)PO(H), ($C_{1-3}$-alkoxy)PO ($C_{1-3}$-alkyl), ($C_{1-3}$-alkoxy)PO(OH) or di-($C_{1-3}$-alkoxy)-PO group, a 4- to 7-membered cycloalkyleneimino, cycloalkyleneiminocarbonyl or cycloalkyleneiminosulphonyl group, wherein in each case the methylene group in the 4 position of a 6- or 7-membered cycloalkyleneimino group may be replaced by an oxygen or sulphur atom, by a sulphinyl, sulphonyl, —NH or —N($C_{1-3}$-alkyl) group, or $R_1$ and $R_2$ together denote a methylenedioxy, ethylenedioxy, n-propylene, n-butylene or 1,4-butadienylene group, $R_3$ denotes a hydrogen atom, denotes a $C_{1-6}$-alkyl, $C_{3-7}$-cycloalkyl, trifluoromethyl or heteroaryl group, a phenyl or naphthyl group optionally mono- or disubstituted by a fluorine, chlorine, bromine or iodine atom, by a trifluoromethyl, $C_{1-3}$-alkyl or $C_{1-3}$-alkoxy group, whilst in the case of disubstitution the substituents may be identical or different, which may additionally be substituted
by a hydroxy, hydroxy-$C_{1-3}$-alkyl or $C_{1-3}$-alkoxy-$C_{1-3}$-alkyl group,
by a cyano, cyano-$C_{1-3}$-alkyl, cyano-$C_{2-3}$-alkenyl, cyano-$C_{2-3}$-alkynyl, carboxy, carboxy-$C_{1-3}$-alkyl, carboxy-$C_{2-3}$-alkenyl, carboxy-$C_{2-3}$-alkynyl, $C_{1-3}$-alkoxycarbonyl, $C_{1-3}$-alkoxycarbonyl-$C_{1-3}$-alkyl, $C_{1-3}$-alkoxycarbonyl-$C_{2-3}$-alkenyl or $C_{1-3}$-alkoxycarbonyl-$C_{2-3}$-alkynyl group,
by a $C_{1-3}$-alkylcarbonyl, $C_{1-3}$-alkylcarbonyl-$C_{1-3}$-alkyl, $C_{1-3}$-alkylcarbonyl-$C_{2-3}$-alkenyl or $C_{1-3}$-alkylcarbonyl-$C_{2-3}$-alkynyl group,
by an aminocarbonyl, aminocarbonyl-$C_{1-3}$-alkyl, aminocarbonyl-$C_{2-3}$-alkenyl, aminocarbonyl-$C_{2-3}$-alkynyl, $C_{1-3}$-alkylaminocarbonyl, $C_{1-3}$-alkylaminocarbonyl-$C_{1-3}$-alkyl, $C_{1-3}$-alkylaminocarbonyl-$C_{2-3}$-alkenyl, $C_{1-3}$-alkylaminocarbonyl-$C_{2-3}$-alkynyl, di-($C_{1-3}$-alkyl)-aminocarbonyl, di-($C_{1-3}$-alkyl)-aminocarbonyl-$C_{1-3}$-alkyl, di-($C_{1-3}$-alkyl)-aminocarbonyl-$C_{2-3}$-alkenyl or di-($C_{1-3}$-alkyl)-aminocarbonyl-$C_{2-3}$-alkynyl group,
by a nitro, nitro-$C_{1-3}$-alkyl, nitro-$C_{2-3}$-alkenyl or nitro-$C_{2-3}$-alkynyl group,
by an amino, $C_{1-3}$-alkylamino, di-($C_{1-3}$-alkyl)-amino, amino-$C_{1-3}$-alkyl, $C_{1-3}$-alkylamino-$C_{1-3}$-alkyl or di-($C_{1-3}$-alkyl)-amino-$C_{1-3}$-alkyl group,
by a $C_{1-3}$-alkylcarbonylamino, $C_{1-3}$-alkylcarbonylamino-$C_{1-3}$-alkyl, N—($C_{1-3}$-alkyl)-$C_{1-3}$-alkylcarbonylamino, N—($C_{1-3}$-alkyl)-$C_{1-3}$-alkylcarbonylamino-$C_{1-3}$-alkyl, $C_{1-3}$-alkylsulphonylamino, $C_{1-3}$-alkylsulphonylamino-$C_{1-3}$-alkyl, N—($C_{1-3}$-alkyl)-$C_{1-3}$-alkylsulphonylamino or N—($C_{1-3}$-alkyl)-$C_{1-3}$-alkylsulphonylamino-$C_{1-3}$-alkyl group,
by a 4- to 7-membered cycloalkyleneimino, cycloalkyleneiminocarbonyl, cycloalkyleneiminosulphonyl, cycloalkyleneimino-$C_{1-3}$-alkyl, cycloalkyleneiminocarbonyl-$C_{1-3}$-alkyl or cycloalkyleneiminosulphonyl-$C_{1-3}$-alkyl group, wherein in each case the methylene group in the 4 position of a 6- or 7-membered cycloalkyleneimino group may be replaced by an oxygen or sulphur atom, by a sulphinyl, sulphonyl, —NH or —N($C_{1-3}$-alkyl) group,
or by a heteroaryl or heteroaryl-$C_{1-3}$-alkyl group, $R_4$ denotes a hydrogen atom, a $C_{1-3}$-alkyl group or a prodrug group, $R_5$ denotes a hydrogen atom or a $C_{1-3}$-alkyl group and $R_6$ denotes a hydrogen, fluorine, chlorine, bromine or iodine atom,
a trifluoromethyl or heteroaryl group, a $C_{1-3}$-alkoxy group optionally substituted by 1 to 3 fluorine atoms, an amino-$C_{1-3}$-alkoxy, $C_{1-3}$-alkylamino-$C_{2-3}$-alkoxy or benzylamino-$C_{2-3}$-alkoxy group, a cycloalkyleneimino-$C_{2-3}$-alkoxy group with 4 to 7 ring members, a di-($C_{1-3}$-alkyl)-amino-$C_{2-3}$-alkoxy or $C_{1-3}$-alkylmercapto group,
a nitro, cyano, carboxy, $C_{1-3}$-alkoxycarbonyl, aminocarbonyl, $C_{1-3}$-alkylaminocarbonyl, di-($C_{1-3}$-alkyl)-aminocarbonyl, piperidinocarbonyl or tetrazolyl group,
a $C_{1-3}$-alkylcarbonylamino group optionally substituted at the nitrogen-atom by a $C_{1-3}$-alkyl group,
an imidazolyl or piperazino group optionally substituted at the imino group by a $C_{1-3}$-alkyl group,
a $C_{1-4}$-alkyl group, which may be terminally substituted
by a hydroxy, $C_{1-3}$-alkoxy, carboxy, $C_{1-3}$-alkoxycarbonyl, amino, $C_{1-4}$-alkylamino, di-($C_{1-4}$-alkyl)-amino, phenylamino, N-phenyl-$C_{1-3}$-alkylamino, phenyl-n-$C_{1-3}$-alkylamino, N—($C_{1-3}$-alkyl)-phenyl-n-$C_{1-3}$-alkylamino or di-(phenyl-n-$C_{1-3}$-alkyl)-amino group,
by a 4- to 7-membered cycloalkyleneimino group wherein
a methylene group linked to the imino group may be replaced by a carbonyl or sulphonyl group or
one or two hydrogen atoms may each be replaced by a $C_{1-3}$-alkyl group and/or
in each case the methylene group in the 4 position of a 6- or 7-membered cycloalkyleneimino group may be substituted by a carboxy, $C_{1-3}$-alkoxycarbonyl, aminocarbonyl, $C_{1-3}$-alkylaminocarbonyl, di-($C_{1-3}$-alkyl)-aminocarbonyl, phenyl-n-$C_{1-3}$-alkylamino or N—($C_{1-3}$-alkyl)-phenyl-n-$C_{1-3}$-alkylamino group or may be replaced by an oxygen or sulphur atom, by a sulphinyl, sulphonyl, —NH or —N($C_{1-3}$-alkyl) group,
by a 5- to 7-membered cycloalkenyleneimino group wherein the double bond is isolated from the nitrogen atom,
by a $C_{4-7}$-cycloalkylamino, N—($C_{1-3}$-alkyl)-$C_{4-7}$-cycloalkylamino or $C_{5-7}$-cycloalkenylamino group wherein position 1 of the ring is not involved in the double bond and wherein the nitrogen atom may be substituted by a $C_{1-3}$-alkyl group,
by a $C_{1-3}$-alkylcarbonylamino, N—($C_{1-3}$-alkyl)-$C_{1-3}$-alkylcarbonylamino, aminocarbonyl, $C_{1-3}$-alkylaminocarbonyl or di-($C_{1-3}$-alkyl)-aminocarbonyl group,
or $R_6$ denotes a group of formula $$—N(R_a)—CO—(CH_2)_n—R_b \quad (II),$$

wherein
$R_a$ denotes a $C_{1-3}$-alkyl group,
n one of the numbers 0, 1 or 2 and
$R_b$ denotes an amino, $C_{1-4}$-alkylamino, phenylamino, N—($C_{1-4}$-alkyl)-phenylamino, benzylamino, N—($C_{1-4}$-alkyl)-benzylamino or di-($C_{1-4}$-alkyl)-amino group or a 4- to 7-membered cycloalkyleneimino group, wherein in each case the methylene group in the 4 position of a 6- or 7-membered cycloalkyleneimino group may be replaced by an oxygen or sulphur atom, by a sulphinyl, sulphonyl, —NH or —N($C_{1-3}$-alkyl) group,
a group of formula $$—N(R_c)—(CH_2)_m—(CO)_o—R_d \quad (III),$$

wherein
$R_c$ denotes a $C_{1-3}$-alkyl, $C_{1-3}$-alkylcarbonyl, arylcarbonyl, benzylcarbonyl, $C_{1-3}$-alkylsulphonyl, arylsulphonyl or benzylsulphonyl group,
m denotes one of the numbers 1, 2, 3 or 4,
o denotes one of the numbers 0 or 1 and
$R_d$ has the meanings given for $R_b$ hereinbefore or denotes a di-($C_{1-4}$-alkyl)-amino-$C_{1-3}$-alkylamino group optionally substituted in the 1 position by a $C_{1-3}$-alkyl group, or an N—(C$_{1-3}$-alkyl)-C$_{1-3}$-alkylsulphonylamino group,
whilst additionally any carboxy, amino or imino group present may be substituted by a group which can be cleaved in vivo (prodrug group), and by a group which can be cleaved in vivo from an imino or amino group is meant, for example, a hydroxy group, an acyl group such as the benzoyl or pyridinoyl group or a C$_{1-16}$-alkanoyl group such as the formyl, acetyl, propionyl, butanoyl, pentanoyl or hexanoyl group, an allyloxycarbonyl group, a C$_{1-16}$-alkoxycarbonyl group such as the methoxycarbonyl, ethoxycarbonyl, propoxycarbonyl, isopropoxycarbonyl, butoxycarbonyl, tert.butoxycarbonyl, pentoxycarbonyl, hexyloxycarbonyl, octyloxycarbonyl, nonyloxycarbonyl, decyloxycarbonyl, undecyloxycarbonyl, dodecyloxycarbonyl or hexadecyloxycarbonyl group, a phenyl-C$_{1-6}$-alkoxycarbonyl group such as the benzyloxycarbonyl, phenylethoxycarbonyl or phenylpropoxycarbonyl group, a C$_{1-3}$-alkylsulphonyl-C$_{2-4}$-alkoxycarbonyl, C$_{1-3}$-alkoxy-C$_{2-4}$-alkoxy-C$_{2-4}$-alkoxycarbonyl or R$_e$CO—O—(R$_f$CR$_g$)—O—CO group wherein R$_e$ denotes a C$_{1-8}$-alkyl, C$_{5-7}$-cycloalkyl, phenyl or phenyl-C$_{1-3}$-alkyl group, R$_f$ denotes a hydrogen atom, a C$_{1-3}$-alkyl, C$_{5-7}$-cycloalkyl or phenyl group and R$_g$ denotes a hydrogen atom, a C$_{1-3}$-alkyl or R$_e$CO—O—(R$_f$CR$_g$)—O group wherein R$_e$ to R$_g$ are as hereinbefore defined, and additionally the phthalimido group may be used for an amino group, whilst the abovementioned ester groups may also be used as a group which can be converted in vivo into a carboxy group, furthermore the term an aryl group denotes a phenyl or naphthyl group optionally mono- or disubstituted by a fluorine, chlorine, bromine or iodine atom or by a trifluoromethyl, C$_{1-3}$-alkyl or C$_{1-3}$-alkoxy group, whilst in the case of disubstitution the substituents may be identical or different, and by a heteroaryl group is meant a monocyclic 5 or 6-membered heteroaryl group optionally substituted by one or two C$_{1-3}$-alkyl groups, whilst the 6-membered heteroaryl group contains one, two or three nitrogen atoms and the 5-membered heteroaryl group contains an imino group optionally substituted by a C$_{1-3}$-alkyl group, an oxygen or sulphur atom or an imino group optionally substituted by a C$_{1-3}$-alkyl group and an oxygen or sulphur atom or one or two nitrogen atoms, and moreover a phenyl ring may be fused to the abovementioned monocyclic heterocyclic groups via two adjacent carbon atoms.

Particular mention should be made of the compounds of the abovementioned general formula I, wherein X and R$_1$ to R$_5$ are as hereinbefore defined and R$_6$ is as hereinbefore defined, with the exception of an aminocarbonyl, C$_{1-3}$-alkylaminocarbonyl, di-(C$_{1-3}$-alkyl)-aminocarbonyl, piperidinocarbonyl or tetrazolyl group, an imidazolyl or piperazino group optionally substituted by a C$_{1-3}$-alkyl group at the imino group, a C$_{1-4}$-alkyl group, the terminal carboxy, C$_{1-3}$-alkoxycarbonyl group, an N—(C$_{1-3}$-alkyl)-C$_{1-3}$-alkylsulphonylamino group or a group of formula

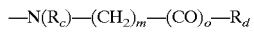    (III), wherein

R$_c$ denotes a C$_{1-3}$-alkyl group.

Preferred compounds of the above general formula I are those wherein

X denotes an oxygen atom,

R$_1$ denotes a C$_{1-3}$-alkoxy, trifluoromethyl, di-(C$_{1-3}$-alkyl)-amino, pyrrolidino or pyrrolo group, an amino or C$_{1-3}$-alkylamino group wherein an aminohydrogen atom may be replaced by a C$_{1-3}$-alkylcarbonyl, phenyl-C$_{1-3}$-alkylcarbonyl, benzoyl, aminocarbonyl, C$_{1-3}$-alkylsulphonyl, phenylsulphonyl, carboxy-C$_{1-3}$-alkyl or C$_{1-3}$-alkyloxycarbonyl-C$_{1-3}$-alkyl group, or a phenyl group optionally substituted by a C$_{1-3}$-alkyl group, R$_2$ denotes a hydrogen atom or a C$_{1-3}$-alkoxy group or R$_1$ and R$_2$ together denote a methylenedioxy group, R$_3$ denotes a C$_{1-3}$-alkyl or phenyl group or a phenyl group substituted by a cyano, amino-C$_{1-3}$-alkyl or N—(C$_{1-3}$-alkanoyl)-amino-C$_{1-3}$-alkyl group, R$_4$ denotes a hydrogen atom, R$_5$ denotes a hydrogen atom and R$_6$ denotes a hydrogen, fluorine, chlorine, bromine or iodine atom, a trifluoromethyl, 4-(C$_{1-3}$-alkyl)-piperazino, pyridinyl, imidazolyl, tetrazolyl, C$_{1-3}$-alkoxy or C$_{1-3}$-alkylmercapto group, a nitro, cyano, carboxy or C$_{1-3}$-alkyloxycarbonyl group or a C$_{1-3}$-alkylcarbonylamino group optionally substituted at the nitrogen atom by a C$_{1-3}$-alkyl group, a piperidinocarbonyl group or an aminocarbonyl group optionally substituted by one or two C$_{1-3}$-alkyl groups, a C$_{1-3}$-alkyl group, which may be terminally substituted by an amino, C$_{1-4}$-alkylamino, di-(C$_{1-4}$-alkyl)-amino, phenylamino, N-phenyl-C$_{1-3}$-alkylamino, phenyl-n-C$_{1-3}$-alkylamino, N—(C$_{1-3}$-alkyl)-phenyl-n-C$_{1-3}$-alkylamino or di-(phenyl-n-C$_{1-3}$-alkyl)-amino group, by a pyrrolidino, piperidino, hexamethyleneimino, morpholino, thiomorpholino, 1-oxido-thiomorpholino or piperazino group, whilst the piperidino group may additionally be substituted by one or two C$_{1-3}$-alkyl groups or by a carboxy, C$_{1-3}$-alkoxycarbonyl, aminocarbonyl, C$_{1-3}$-alkylaminocarbonyl-di-(C$_{1-3}$-alkyl)-aminocarbonyl or N—(C$_{1-3}$-alkyl)-phenyl-n-C$_{1-3}$-alkylamino group, by a C$_{5-7}$-cycloalkylamino or C$_{5-7}$-cycloalkenylamino group wherein position 1 of the ring is not involved in the double bond, by a C$_{1-3}$-alkylcarbonylamino, N—(C$_{1-3}$-alkyl)-C$_{1-3}$-alkylcarbonylamino, carboxy, C$_{1-3}$-alkoxycarbonyl, aminocarbonyl, C$_{1-3}$-alkylaminocarbonyl or di-(C$_{1-3}$-alkyl)-aminocarbonyl group, a C$_{1-3}$-alkoxy group, which is terminally substituted by an amino, C$_{1-3}$-alkylamino or di-(C$_{1-3}$-alkyl)-amino group, a group of formula

    (II), wherein

R$_a$ denotes a C$_{1-3}$-alkyl group, n denotes one of the numbers 0, 1 or 2 and $R_b$ denotes an amino, $C_{1-4}$-alkylamino or di-($C_{1-4}$-alkyl)-amino group or a pyrrolidino, piperidino, hexamethyleneimino, morpholino, thiomorpholino, 1-oxido-thiomorpholino or piperazino group, a group of formula

$$-N(R_c)-(CH_2)_m-(CO)_o-R_d \qquad (III),$$

wherein $R_c$ denotes a $C_{1-3}$-alkyl, $C_{1-3}$-alkylcarbonyl or $C_{1-3}$-alkylsulphonyl group, m denotes one of the numbers 1, 2, 3 or 4, o denotes one of the numbers 0 or 1 and $R_d$ has the meanings given for $R_b$ hereinbefore or denotes a di-($C_{1-4}$-alkyl)-amino-$C_{1-3}$-alkylamino group optionally substituted in the 1 position by a $C_{1-3}$-alkyl group, or an N—($C_{1-3}$-alkyl)-$C_{1-3}$-alkylsulphonylamino group, the isomers and the salts thereof.

Particularly preferred compounds of the above general formula I are those wherein X denotes an oxygen atom, $R_1$ denotes a methoxy, ethoxy, trifluoromethyl, phenyl, methylphenyl, dimethylamino, pyrrolidino or pyrrolo group, an amino group which may be substituted by a methyl, carboxymethyl, methoxycarbonylmethyl, acetyl, phenylacetyl, benzoyl, methanesulphonyl, benzolsulphonyl or aminocarbonyl group, $R_2$ denotes a hydrogen atom, a methoxy or ethoxy group or $R_1$ and $R_2$ together denote a methylenedioxy group, $R_3$ denotes an ethyl group or a phenyl group optionally substituted by a cyano, aminomethyl or N-acetyl-aminomethyl group, $R_4$ denotes a hydrogen atom, $R_5$ denotes a hydrogen atom and $R_6$ denotes a hydrogen, fluorine, chlorine, bromine or iodine atom,
  a methyl, trifluoromethyl, methoxy, ethoxy, methylmercapto, cyano, carboxy, methoxycarbonyl, ethoxycarbonyl, aminocarbonyl, dimethylaminocarbonyl, piperidinocarbonyl, nitro, 4-methyl-piperazino, imidazolyl, pyridinyl or tetrazolyl group,
  an ethyloxy or n-propyloxy group terminally substituted by a dimethylamino group,
  a methyl or ethyl group substituted by a carboxy, methoxycarbonyl, ethoxycarbonyl, aminocarbonyl or dimethylaminocarbonyl group,
  a $C_{1-3}$-alkyl group, which may be terminally substituted by an amino, $C_{1-4}$-alkylamino, cyclohexylamino, benzylamino or phenylamino group wherein a hydrogen atom of the amino-nitrogen atom may be replaced in each case by a $C_{1-3}$-alkyl, benzyl, acetyl or dimethylaminocarbonyl group,
    by a piperidino group optionally substituted by one or two methyl groups,
    by a piperidino group substituted by a carboxy, methoxycarbonyl, ethoxycarbonyl or dimethylaminocarbonyl group,
    by a pyrrolidino, 3,4-dehydro-piperidino, hexamethyleneimino, morpholino, thiomorpholino, 1-oxo-thiomorpholino or piperazino group, a $C_{1-3}$-alkylamino group wherein the hydrogen atom of the amino-nitrogen atom is replaced
    by an ethyl or n-propyl group, each of which is terminally substituted by a dimethylamino group,
    by a $C_{2-3}$-alkanoyl group which may be substituted in the 2 or 3 position by an amino, $C_{1-3}$-alkylamino, di-($C_{1-3}$-alkyl)-amino, pyrrolidino, piperidino, morpholino or piperazino group,
    by an aminocarbonyl, methylaminocarbonyl, dimethylaminocarbonyl, piperidinocarbonyl or methanesulphonyl group,
  and additionally the $C_{1-3}$-alkyl moiety of the $C_{1-3}$-alkylamino group may be substituted
    by an aminocarbonyl group,
    by a $C_{1-3}$-alkylaminocarbonyl or di-($C_{1-3}$-alkyl)-aminocarbonyl group wherein a $C_{2-3}$-alkyl moiety may additionally be terminally substituted by a dimethylamino group, by a pyrrolidinocarbonyl, piperidinocarbonyl, morpholinocarbonyl or piperazinocarbonyl group,
    whilst the $C_{2-3}$-alkyl moiety of the abovementioned $C_{1-3}$-alkylamino group may also be terminally substituted by an amino, $C_{1-3}$-alkylamino, di-($C_{1-3}$-alkyl)-amino, pyrrolidino, piperidino, morpholino or piperazino group, in particular those compounds of the above general formula I wherein
  either X, $R_1$ and $R_3$ to $R_6$ are as hereinbefore defined and $R_2$ denotes a hydrogen atom,
  or X and $R_3$ to $R_6$ are as hereinbefore defined, $R_1$ and $R_2$, which may be identical or different, each denotes a $C_{1-3}$-alkoxy group, the isomers and the salts thereof.

Quite specially preferred compounds of the above general formula I are those wherein X denotes an oxygen atom, $R_1$ denotes an amino, methoxy or ethoxy group, $R_2$ denotes a hydrogen atom or in position 5 a methoxy or ethoxy group, $R_3$ denotes a methyl, ethyl or phenyl group, $R_4$ and $R_5$ each denote a hydrogen atom and $R_6$ denotes a methyl or ethyl group substituted by a methylamino, ethylamino, piperidino or 4-(dimethylaminocarbonyl)-piperidino group, wherein the amino-hydrogen atom of the methylamino- and ethylamino group is replaced by a methyl or benzyl group, an N-dimethylaminomethylcarbonyl-N-methyl-amino group or an N-acetyl-N—($C_{2-3}$-alkyl)-amino group wherein the $C_{2-3}$-alkyl moiety in each case is terminally substituted by a dimethylamino group, and the salts thereof.

The following particularly useful compounds of general formula I are mentioned by way of example;

(a) 3-(Z)-{1-[4-(piperidin-1-yl-methyl)-anilino]-1-phenyl-methylidene}-5,6-dimethoxy-2-indolinone, (b) 3-(Z)-(1-{4-[(N-benzyl-N-methyl-amino)-methyl]-anilino}-1-phenyl-methylidene)-5,6-dimethoxy-2-indolinone, (c) 3-(Z)-{1-(4-(dimethylamino-methyl)-anilino)-1-phenyl-methylidene}-5,6-dimethoxy-2-indolinone, (d) 3-(Z)-{1-[4-(N-dimethylaminomethylcarbonyl-N-methyl-amino)-anilino]-1-phenyl-methylidene}-5,6-dimethoxy-2-indolinone, (e) 3-(Z)-(1-{4-[2-(4-dimethylcarboxamide-piperidin-1-yl)-ethyl]-anilino}-1-phenyl-methylidene)-5,6-dimethoxy-2-indolinone, (f) 3-(Z)-{1-[4-(N-dimethylaminomethylcarbonyl-N-methyl-amino)-anilino]-1-ethyl-methylidene}-5,6-dimethoxy-2-indolinone and (g) 6-amino-3-(Z)-{1-[4-(piperidin-1-yl-methyl)-anilino]-1-phenyl-methylidene}-2-indolinone, (h) 3-(Z)-(1-{4-[N-acetyl-N-(2-dimethylamino-ethyl)-amino]-anilino}-1-phenyl-methylidene)-5,6-dimethoxy-2-indolinone and (i) 3-(Z)-(1-{4-[N-acetyl-N-(3-dimethylamino-propyl)-amino]-anilino}-1-phenyl-methylidene)-5,6-dimethoxy-2-indolinone as well as the salts thereof.

According to the invention, the new compounds may be obtained, for example, by the following methods known in principle from the literature:

a. reaction of a compound of general formula

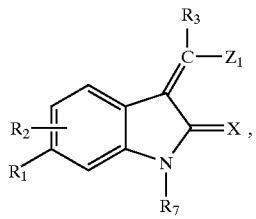

(IV)

wherein

X and $R_1$ to $R_3$ are defined as in claims 1 to 4, $R_7$ denotes a hydrogen atom, a protecting group for the nitrogen atom of the lactam group or a bond to a solid phase and $Z_1$ denotes a halogen atom, a hydroxy, alkoxy or arylalkoxy-group, e.g. a chlorine or bromine atom, a methoxy, ethoxy or benzyloxy group, with an amine of general formula

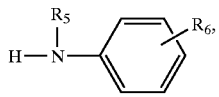

(V)

wherein $R_5$ and $R_6$ are defined as in claims 1 to 4, and if necessary subsequently cleaving any protecting group used for the nitrogen atom of the lactam group or cleaving from a solid phase.

A protecting group for the nitrogen atom of the lactam group might be for example an acetyl, benzoyl, ethoxycarbonyl, tert.butyloxycarbonyl or benzyloxycarbonyl group and the solid phase might be a Rink resin such as a p-benzyloxybenzylalcohol resin, whilst the bond may conveniently be formed via an intermediate member such as a 2,5-dimethoxy-4-hydroxy-benzyl derivative.

The reaction is conveniently carried out in a solvent such as dimethylformamide, toluene, acetonitrile, tetrahydrofuran, dimethylsulphoxide, methylene chloride or mixtures thereof, optionally in the presence of an inert base such as triethylamine, N-ethyl-diisopropylamine or sodium hydrogen carbonate at temperatures between 20 and 175° C., whilst any protecting group used can be cleaved simultaneously by transamidation.

If $Z_1$ in a compound of general formula IV denotes a halogen atom, the reaction is preferably carried out in the presence of an inert base at temperatures between 20 and 120° C.

If $Z_1$ in a compound of general formula IV denotes a hydroxy, alkoxy or aralkoxy group, the reaction is preferably carried out at temperatures between 20 and 200° C.

If any protecting group used subsequently has to be cleaved, this is conveniently carried out either hydrolytically in an aqueous or alcoholic solvent, e.g. in methanol/water, ethanol/water, isopropanol/water, tetrahydrofuran/water, dioxane/water, dimethylformamide/water, methanol or ethanol in the presence of an alkali metal base such as lithium hydroxide, sodium hydroxide or potassium hydroxide at temperatures between 0 and 100° C., preferably at temperatures between 10 and 50° C., or advantageously by transamidation with a primary or secondary organic base such as butylamine, dimethylamine or piperidine in a solvent such as methanol, ethanol, dimethylformamide and mixtures thereof or in an excess of the amine used at temperatures between 0 and 100° C., preferably at temperatures between 10 and 50° C.

Any solid phase used is preferably cleaved using trifluoroacetic acid and water in the presence of a dialkylsulphide such as dimethylsulphide at temperatures between 0 and 35° C., preferably at ambient temperature.

b. In order to prepare a compound of general formula I wherein $R_1$ denotes an amino group:

Reduction of a compound of general formula

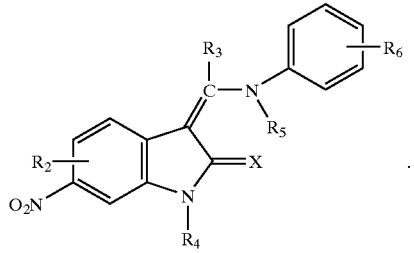

(VI)

The reduction of a nitro group is preferably carried out by hydrogenolysis, e.g. with hydrogen in the presence of a catalyst such as palladium/charcoal or Raney nickel in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

c. In order to prepare a compound of general formula I wherein $R_1$ or/and $R_2$ denotes one of the abovementioned substituted sulphinyl or sulphonyl groups:

oxidation of a compound of general formula

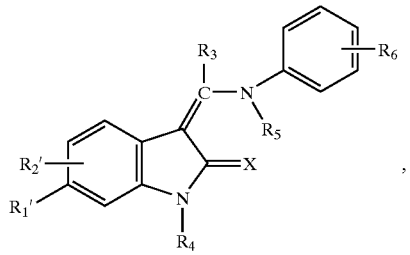

(VII)

wherein $R_3$ to $R_6$ are defined as in claims 1 to 4 and
one of the groups $R_1$ and $R_2{}'$ denotes one of the substituted mercapto or sulphinyl groups mentioned above for $R_1$ and $R_2$ and the other one assumes the meanings given above for $R_1$ or $R_2$ with the exception of the mercapto or sulphinyl groups or both groups $R_1{}'$ and $R_2{}'$, denote one of the substituted mercapto or sulphinyl groups mentioned above for $R_1$ and $R_2$.

The oxidation is preferably carried out in a solvent or mixture of solvents, e.g. in water, water/pyridine, acetone, methylene chloride, acetic acid, acetic acid/acetic anhydride, dilute sulphuric acid or trifluoroacetic acid, expediently at temperatures between −80 and 100° C., depending on the oxidising agent used.

In order to prepare a corresponding sulphinyl compound of general formula I the oxidation is expediently carried out with one equivalent of the oxidising agent used, e.g. with hydrogen peroxide in glacial acetic acid, trifluoroacetic acid or formic acid at 0 to 20° C. or in acetone at 0 to 60° C., with a peracid such as performic acid in glacial acetic acid or trifluoroacetic acid at 0 to 50° C. or with m-chloroperbenzoic acid in methylene chloride, chloroform or dioxane at −20 to 80° C., with sodium metaperiodate in aqueous methanol or ethanol at −15 to 25° C., with bromine in glacial acetic acid or aqueous acetic acid optionally in the presence of a weak base such as sodium acetate, with N-bromosuccinimide in ethanol, with tert.butylhypochlorite in methanol at −80 to −30° C., with iodobenzodichloride in aqueous pyridine at 0 to 50° C., with nitric acid in glacial acetic acid at 0 to 20° C., with chromic acid in glacial acetic acid or in acetone at 0 to 20° C. and with sulphurylchloride in methylene chloride at −70° C., the resulting thioether-chlorine complex is expediently hydrolysed with aqueous ethanol.

In order to prepare a sulphonyl compound of general formula I the oxidation is expediently carried out starting from a corresponding sulphinyl compound with one or more equivalents of the oxidising agent used or starting from a corresponding mercapto compound, expediently with two or more equivalents of the oxidising agent used, e.g. with hydrogen peroxide in glacial acetic acid/acetic anhydride, trifluoroacetic acid or in formic acid at 20 to 100° C. or in acetone at 0 to 60° C., with a peracid such as performic acid or m-chloroperbenzoic acid in glacial acetic acid, trifluoroacetic acid, methylene chloride or chloroform at temperatures between 0 and 60° C., with nitric acid in glacial acetic acid at 0 to 20° C., with chromic acid, sodium periodate or potassium permanganate in acetic acid, water/sulphuric acid or in acetone at 0 to 20° C.

If according to the invention a compound of general formula I is obtained which contains an alkoxycarbonyl group, this can be converted by hydrolysis into a corresponding carboxy compound, or If a compound of general formula I is obtained which contains an amino or alkylamino group, this may be converted by alkylation or reductive alkylation into a corresponding alkylamino, dialkylamino or pyrrolidino compound, or If a compound of general formula I is obtained which contains an amino or alkylamino group, this may be converted by acylation into a corresponding acyl compound, or If a compound of general formula I is obtained which contains an amino or alkylamino group, this may be converted by sulphonation into a corresponding sulphonyl compound, for example into the corresponding alkylsulphonylamino, phenylsulphonylamino, benzylsulphonylamino or N-alkyl-alkylsulphonylamino group, or If a compound of general formula I is obtained which contains an amino group, this can be converted by a reaction of condensation into a corresponding pyrrolo compound, or If a compound of general formula I is obtained which contains a carboxy group, this may be converted by esterification or amidation into a corresponding ester or aminocarbonyl compound, or If a compound of general formula I is obtained which contains a cyano group, this can be converted by reduction into a corresponding aminomethyl compound, or If a compound of general formula I is obtained which contains an amino or alkylamino group, this may be converted by reaction with cyanic acid or a corresponding isocyanate into a corresponding ureido compound.

The subsequent hydrolysis is preferably carried out in an aqueous solvent, e.g. in water, methanol/water, ethanol/water, isopropanol/water, tetrahydrofuran/water or dioxane/water, in the presence of an acid such as trifluoroacetic acid, hydrochloric acid or sulphuric acid or in the presence of an alkali metal base such as lithium hydroxide, sodium hydroxide or potassium hydroxide at temperatures between 0 and 100° C., preferably at temperatures between 10 and 50° C.

The subsequent reductive alkylation is preferably carried out in a suitable solvent such as methanol, methanol/water, methanol/water/ammonia, ethanol, ether, tetrahydrofuran, dioxane, methylene chloride or dimethylformamide optionally with the addition of an acid such as hydrochloric acid in the presence of catalytically activated hydrogen, e.g. hydrogen in the presence of Raney nickel, platinum or palladium/charcoal, or in the presence of a metal hydride such as sodium borohydride, sodium cyanoborohydride, lithium borohydride or lithium aluminium hydride at temperatures between 0 and 100° C., preferably at temperatures between 20 and 80° C.

The subsequent alkylation is carried out with an alkylating agent such as an alkyl halide or dialkyl sulphate such as methyliodide, dimethylsulphate or propylbromide preferably in a solvent such as methanol, ethanol, methylene chloride, tetrahydrofuran, toluene, dioxane, dimethylsulphoxide or dimethylformamide optionally in the presence of an inorganic or a tertiary organic base such as potassium carbonate, triethylamine, N-ethyl-diisopropylamine, pyridine or dimethylaminopyridine, preferably at temperatures between 20° C. and the boiling temperature of the solvent used.

The subsequent acylation is preferably carried out in a solvent such as methylene chloride, diethylether, tetrahydrofuran, toluene, dioxane, acetonitrile, dimethylsulphoxide or dimethylformamide, optionally in the presence of an inorganic or a tertiary organic base, preferably at temperatures between 20° C. and the boiling temperature of the solvent used. The acylation with a corresponding acid is preferably carried out in the presence of a dehydrating agent, e.g. in the presence of isobutyl chloroformate, tetraethyl orthocarbonate, trimethyl orthoacetate, 2,2-dimethoxypropane, tetramethoxysilane, thionylchloride, trimethylchlorosilane, phosphorus trichloride, phosphorus pentoxide, N,N'-dicyclohexylcarbodiimide, N,N'-dicyclohexylcarbodiimide/N-hydroxysuccinimide, N,N'-dicyclohexylcarbodiimide/1-hydroxy-benztriazole, 2-(1H-benzotriazol-1-yl)-1,1,3,3-tetramethyluronium-tetrafluoroborate, 2-(1H-benzotriazol-1-yl)-1,1,3;3-tetramethyluronium-tetrafluoroborate/1-hydroxy-benzotriazole, N,N'-carbonyldiimidazole or triphenylphosphine/carbon tetrachloride, and optionally with the addition of a base such as pyridine, 4-dimethylamino-pyridine, N-methyl-morpholine or triethylamine, conveniently at temperatures between 0 and 150° C., preferably at temperatures between 0 and 100° C., and the acylation with a corresponding reactive compound such as an anhydride, ester, imidazolide or halide thereof is optionally carried out in the presence of a tertiary organic base such as triethylamine, N-ethyl-diisopropylamine, N-methyl-morpholine or pyridine at temperatures between 0 and 150° C., preferably at temperatures between 50 and 100° C.

The subsequent sulphonation is preferably carried out in a solvent such as methylene chloride, diethylether, tetrahydrofuran, toluene, dioxane, acetonitrile, dimethylsulphoxide or dimethylformamide optionally in the presence of an inorganic or tertiary organic base, preferably at temperatures between 20° C. and the boiling temperature of the solvent used. The sulphonation is carried out with a corresponding reactive compound, for example the sulphonylhalides, optionally in the presence of a tertiary organic base such as triethylamine, N-ethyl-diisopropylamine, N-methyl-morpholine, pyridine or dimethylaminopyridine at temperatures between 0 and 150° C., preferably at temperatures between 50 and 100° C.

The subsequent condensation for converting an amino group into a pyrrolo group is expediently carried out in a solvent such as dimethylformamide, toluene, acetonitrile, tetrahydrofuran, dimethylsulphoxide, methylene chloride or mixtures thereof, preferably in the presence of a acid such as formic acid, glacial acetic acid or trifluoroacetic acid or using the acid as the sole solvent with condesable 1,4-difunctional n-butylene or tetrahydrofuran derivatives, for example with 2,5-dimethoxytetrahydrofuran or 2,5-hexanedione, at temperatures between 0 and 120° C. or the boiling temperature of the reaction mixture.

The subsequent esterification or amidation is expediently carried out by reacting a corresponding reactive carboxylic acid derivative with a corresponding alcohol or amine as described hereinbefore.

The subsequent reduction of a cyano group is preferably carried out in a suitable solvent such as methanol, methanol/water, methanol/water/ammonia, ethanol, ether, tetrahydrofuran, dioxane, methylene chloride or dimethylformamide optionally with the addition of methanolic ammonia with hydrogen in the presence of a hydrogenation catalyst, e.g. in the presence of Raney nickel or palladium/charcoal, at a hydrogen pressure of 1 to 5 bar, preferably at temperatures between 20° C. and the boiling temperature of the solvent used.

The subsequent reaction with a cyanic acid or a corresponding isocyanate is preferably carried out in a suitable solvent such as ethanol, tetrahydrofuran or dioxane at temperatures between 0° C. and the boiling temperature of the reaction mixture; the cyanic acid used is expediently prepared in the reaction mixture by reacting a salt of cyanic acid with an acid, for example by reacting potassium cyanate with glacial acetic acid.

In the reactions described hereinbefore, any reactive groups present such as carboxy, amino, alkylamino or imino groups may be protected during the reaction by conventional protecting groups which are cleaved again after the reaction.

For example, a protecting group for a carboxyl group may be a trimethylsilyl, methyl, ethyl, tert.butyl, benzyl or tetrahydropyranyl group and protecting groups for an amino, alkylamino or imino group may be an acetyl, trifluoroacetyl, benzoyl, ethoxycarbonyl, tert.butoxycarbonyl, benzyloxycarbonyl, benzyl, methoxybenzyl or 2,4-dimethoxybenzyl group and additionally, for the amino group, a phthalyl group.

Any protecting group used is optionally subsequently cleaved for example by hydrolysis in an aqueous solvent, e.g. in water, isopropanol/water, tetrahydrofuran/water or dioxane/water, in the presence of a acid such as trifluoroacetic acid, hydrochloric acid or sulphuric acid or in the presence of an alkali metal base such as lithium hydroxide, sodium hydroxide or potassium hydroxide, at temperatures between 0 and 100° C., preferably at temperatures between 10 and 50° C.

However, a benzyl, methoxybenzyl or benzyloxycarbonyl group is cleaved, for example, hydrogenolytically, e.g. with hydrogen in the presence of a catalyst such as palladium/charcoal in a solvent such as methanol, ethanol, ethyl acetate, dimethylformamide, dimethylformamide/acetone or glacial acetic acid, optionally with the addition of an acid such as hydrochloric acid or glacial acetic acid at temperatures between 0 and 50° C., but preferably at ambient temperature, and at a hydrogen pressure of 1 to 7 bar, but preferably 3 to 5 bar.

A methoxybenzyl group may also be cleaved in the presence of an oxidising agent such as cerium(IV) ammonium nitrate in a solvent such as methylene chloride, acetonitrile or acetonitrile/water at temperatures of between 0 and 50° C., but preferably at ambient temperature.

A 2,4-dimethoxybenzyl group, however, is preferably cleaved in trifluoroacetic acid in the presence of anisol.

A tert.butyl or tert.butyloxycarbonyl group is preferably cleaved by treating with an acid such as trifluoroacetic acid or hydrochloric acid, optionally using a solvent such as methylene chloride, dioxane, ethyl acetate or ether.

A phthalyl group is preferably cleaved in the presence of hydrazine or a primary amine such as methylamine, ethylamine or n-butylamine in a solvent such as methanol, ethanol, isopropanol, toluene/water or dioxane at temperatures between 20 and 50° C.

Moreover, chiral compounds of general formula I obtained may be resolved into their enantiomers and/or diastereomers.

Thus, for example, the compounds of general formula I obtained which occur as racemates may be separated by methods known per se (cf. Allinger N. L. and Eliel E. L. in "Topics in Stereochemistry", Vol. 6, Wiley Interscience, 1971) into their optical antipodes and compounds of general formula I with at least 2 asymmetric carbon atoms may be resolved into their diastereomers on the basis of their physical-chemical differences using methods known per se, e.g. by chromatography and/or fractional crystallisation, and, if these compounds are obtained in racemic form, they may subsequently be resolved into the enantiomers as mentioned above.

The enantiomers are preferably separated by column separation on chiral phases or by recrystallisation from an optically active solvent or by reacting with an optically active substance which forms salts or derivatives such as e.g. esters or amides with the racemic compound, particularly acids and the activated derivatives or alcohols thereof, and separating the diastereomeric mixture of salts or derivatives thus obtained, e.g. on the basis of their differences in solubility, whilst the free antipodes may be released from the pure diastereomeric salts or derivatives by the action of suitable agents. Optically active acids in common use are e.g. the D- and L-forms of tartaric acid or dibenzoyltartaric acid, di-o-tolyltartaric acid, malic acid, mandelic acid, camphorsulphonic acid, glutamic acid, N-acetylglutamic acid, aspartic acid, N-acetylaspartic acid or quinic acid. An optically active alcohol may be for example (+)- or (−)-menthol and an optically active acyl group in amides, for example, may be a (+)- or (−)-menthyloxycarbonyl group.

Furthermore, the compounds of formula I obtained may be converted into the salts thereof, particularly for pharmaceutical use into the physiologically acceptable salts with inorganic or organic acids. Acids which may be used for this purpose include for example hydrochloric acid, hydrobromic acid, sulphuric acid, phosphoric acid, fumaric acid, succinic acid, lactic acid, citric acid, tartaric acid, maleic acid or methanesulphonic acid.

Moreover, if the new compounds of formula I thus obtained contain a carboxy group, they may subsequently, if desired, be converted into the salts thereof with inorganic or organic bases, particularly for pharmaceutical use into the physiologically acceptable salts thereof. Suitable bases for this purpose include for example sodium hydroxide, potassium hydroxide, cyclohexylamine, ethanolamine, diethanolamine and triethanolamine.

The compounds of general formulae IV to VII used as starting materials are known from the literature in some cases or may be obtained by methods known from the literature or are described in the Examples.

As already mentioned, the new compounds of general formula I wherein $R_4$ denotes a hydrogen atom or a prodrug group have valuable pharmacological properties, particularly inhibitory effects on various kinases, especially on receptor-tyrosine kinases such as VEGFR2, PDGFRα, PDGFRβ, FGFR1, FGFR3, EGFR, HER2, IGF1R and HGFR, as well as on complexes of CDK's (Cycline Dependent Kinases) such as CDK1, CDK2, CDK3, CDK4, CDK5, CDK6, CDK7, CDK8 and CDK9 with their specific cyclines (A, B1, B2, C, D1, D2, D3, E, F, G1, G2, H, I and K) and on viral cycline, on the proliferation of cultivated human cells, particularly endothelial cells, e.g. in angiogenesis, but also on the proliferation of other cells, particularly tumour cells.

The biological properties of the new compounds were tested by the following standard procedure, as follows:

Human umbilical endothelial cells (HUVEC) were cultivated in IMDM (Gibco BRL), supplemented with 10% foetal calf serum (FBS) (Sigma), 50 µM of β-mercaptoethanol (Fluka), standard antibiotics, 15 µg/ml of endothelial cell growth factor (ECGS, Collaborative Biomedical Products) and 100 µg/ml of heparin (Sigma) on gelatine-coated culture dishes (0.2% gelatine, Sigma) at 37° C., under 5% $CO_2$ in a water-saturated atmosphere.

In order to investigate the inhibitory activity of the compounds according to the invention the cells were "starved" for 16 hours, i.e. kept in culture medium without growth factors (ECGS+heparin). The cells were detached from the culture dishes using trypsin/EDTA and washed once in serum-containing medium. Then they were seeded out in amounts of $2.5 \times 10^3$ cells per well.

The proliferation of the cells was stimulated with 5 ng/ml of $VEGF_{165}$ (vascular endothelial growth factor; H. Weich, GBF Braunschweig) and 10 µg/ml of heparin. As a control, 6 wells in each dish were not stimulated.

The compounds according to the invention were dissolved in 100% dimethylsulphoxide and added to the cultures in various dilutions as triple measurements, the maximum dimethyl sulphoxide concentration being 0.3%.

The cells were incubated for 76 hours at 37° C., then for a further 16 hours $^3$H-thymidine (0.1 µCi/well, Amersham) was added in order to determine the DNA synthesis. Then the radioactively labelled cells were immobilised on filter mats and the radioactivity incorporated was measured in a β-counter. In order to determine the inhibitory activity of the compounds according to the invention the mean value of the non-stimulated cells was subtracted from the mean value of the factor-stimulated cells (in the presence or absence of the compounds according to the invention).

The relative cell proliferation was calculated as a percentage of the control (HUVEC without inhibitor) and the concentration of active substance which inhibits the proliferation of the cells by 50% ($IC_{50}$) was determined.

The following Table contains the results found:

| compound (Example No.) | $IC_{50}$ [µM] |
|---|---|
| 1 | 0.03 |
| 1 (3) | 0.27 |
| 1 (6) | 0.02 |
| 1 (8) | 0.05 |
| 1 (17) | 0.04 |
| 1 (18) | 0.04 |
| 1 (50) | 0.83 |
| 3 | 0.05 |
| 4 | 0.04 |

In addition the compound of Example 1 (6) was tested on mice for its tolerance. The approximate oral $LD_{50}$ for this compound is over 1,000 mg/kg. The compounds of general formula I are therefore well tolerated.

In view of their inhibitory effect on the proliferation of cells, particularly endothelial cells and tumour cells, the compounds of general formula I are suitable for treating diseases in which the proliferation of cells, particularly endothelial cells, plays a part.

Thus, for example, the proliferation of endothelial cells and the concomitant neovascularisation constitute a crucial stage in tumour progression (Folkman J. et al., Nature 339, 58–61, (1989); Hanahan D. and Folkman J., Cell 86, 353–365, (1996)). Furthermore, the proliferation of endothelial cells is also important in haemangiomas, in metastasisation, rheumatoid arthritis, psoriasis and ocular neovascularisation (Folkman J., Nature Med. 1, 27–31, (1995)). The therapeutic usefulness of inhibitors of endothelial cell proliferation was demonstrated in the animal model for example by O'Reilly et al. and Parangi et al. (O'Reilly M. S. et al., Cell 88, 277–285, (1997); Parangi S. et al., Proc Natl Acad Sci USA 93, 2002–2007, (1996)).

The compounds of general formula I, their tautomers, their stereoisomers or the physiologically acceptable salts thereof are thus suitable, for example, for treating solid tumours, diabetic retinopathy, rheumatoid arthritis and psoriasis, or other diseases in which cell proliferation or angiogenesis play a part.

By reason of their biological properties the compounds according to the invention may be used on their own or in conjunction with other pharmacologically active compounds, for example in tumour therapy, in monotherapy or in conjunction with other anti-tumour therapeutic agents, for example in combination with Topoisomerase inhibitors (e.g. Etoposide), mitosis inhibitors (e.g. Vinblastin, Taxol), compounds which interact with nucleic acids (e.g. cisplatin, Cyclophosphamide, Adriamycin), hormone antagonists (e.g. tamoxifen), inhibitors of metabolic processes (e.g. 5-FU etc.), cytokines (e.g. interferons), kinase inhibitos, antibodies, or in conjunction with radiotherapy, etc. These combinations may be administered either simultaneously or sequentially.

For pharmaceutical use the compounds according to the invention are generally used for warm-blooded vertebrates, particularly humans, in doses of 0.01–100 mg/kg of body weight, preferably 0.1–15 mg/kg. For administration they are formulated with one or more conventional inert carriers and/or diluents, e.g. with corn starch, lactose, glucose, microcrystalline cellulose, magnesium stearate, polyvinylpyrrolidone, citric acid, tartaric acid, water, water/ethanol, water/glycerol, water/sorbitol, water/polyethyleneglycol, propyleneglycol, stearylalcohol, carboxymethylcellulose or fatty substances such as hard fat or suitable mixtures thereof in conventional galenic preparations such as plain or coated tablets, capsules, powders, suspensions, solutions, sprays or suppositories.

The following Examples are intended to illustrate the present invention without restricting it:

Abbreviations:

TBTU=O-(benzotriazol-1-yl)-N,N,N',N'-bis(tetramethylene)-uronium hexafluorophosphate HOBt=1-hydroxy-1H-benzotriazole Preparation of the starting compounds:

EXAMPLE I 1-hydroxy-6-nitro-2-indolinone 2.0 g of 2,4-dinitrophenylacetic acid (prepared according to J: Chem. Soc. 1948, 1717) are dissolved in 40 ml ethanol and 6.0 ml of conc. hydrochloric acid and 4.1 g of tin-(II)-chloride-dihydrate are added in batches at ambient temperature. The mixture is stirred for 12 hours at ambient temperature and for 4 hours at 60° C. After cooling another 2.0 g of tin-(II)-chloride-dihydrate are added and the mixture is stirred for another 12 hours at ambient temperature. The reaction mixture is diluted with water, extracted with methylene chloride and the organic phase is dried over sodium sulphate. After elimination of the solvent the residue is triturated with ether and the precipitate is filtered off.

Yield: 0.6 g (35% of theory), $R_f$ value: 0.7 (silica gel, methylene chloride/methanol=9:1) $C_8H_6N_2O_4$ ESI mass spectrum: m/z=193 [M−H⁻]

EXAMPLE II 3,4-diethoxy-phenylacetic acid 0.8 g of 3,4-dihydroxy-phenylacetic acid and 6.9 g of barium hydroxide octahydrate are dissolved in 50 ml of water and at ambient temperature 2.9 ml of diethylsulphate are added dropwise. The solution is stirred for 2 hours at ambient temperature and for 2 hours at 40° C. After this time the solution is acidified with saturated potassium hydrogen sulphate solution, mixed with ethyl acetate and the suspension is filtered through Celite. The phases are separated and the ethyl acetate phase is dried over sodium sulphate and concentrated by evaporation. The residue obtained is purified through a silica gel column with toluene/ethyl acetate/ethanol (4:2:1) as eluant.

Yield: 0.5 g (42% of theory), $R_f$ value: 0.5 (silica gel, toluene/ethyl acetate/ethanol=4:2:1) $C_{12}H_{16}O_4$ ESI mass spectrum: m/z=223 [M−H⁻]

EXAMPLE III 4,5-diethoxy-2-nitro-phenylacetic acid 0.5 g of 3,4-diethoxy-phenylacetic acid are placed in 10 ml of acetic acid p.a. and 0.5 ml of 659 nitric acid are added dropwise, so that the internal temperature does not rise above 15° C. The mixture is then heated to 40° C. for 0.5 hours. After this time the solution is poured onto ice water and the precipitate formed is suction filtered. The product is washed with water and dried at 100° C.

Yield: 0.3 g (57% of theory), $R_f$ value 0.5 (silica gel, methylene chloride/methanol=10:1) $C_{12}H_{15}NO_6$ ESI mass spectrum: m/z=292 [M+Na⁺]

EXAMPLE IV tert.butyl 2-nitro-4-trifluormethyl-phenylacetate 2.6 g of potassium-tert.butoxide are placed in 45 ml of dimethylformamide and at an internal temperature of −5° C. 1.3 ml of 3-nitro-trifluorotoluene and 1.5 ml of tert.butyl chloroacetate in 1 ml of dimethylformamide are added dropwise. The mixture is stirred for another 5 minutes and the solution is then poured onto ice water and the precipitate formed is suction filtered.

Yield: 2.5 g (82% of theory), $R_f$ value: 0.4 (silica gel, petroleum ether/ethyl acetate=10:1)

Melting point: 45° C.

EXAMPLE V 2-nitro-4-trifluoromethyl-phenylacetic acid 16.7 g of tert.butyl 2-nitro-4-trifluoromethyl-phenylacetate and 50 ml of trifluoroacetic acid are dissolved in 50 ml of methylene chloride and stirred for 3 hours at ambient temperature. After elimination of the solvent the residue is taken up in petroleum ether/ether (10:1), suction filtered and dried in vacuo at 80° C.

Yield: 13.4 g (98% of theory), $R_f$ value: 0.5 (silica gel, toluene/ethyl acetate/ethanol=4:2:1) $C_9H_6F_3NO_4$ ESI mass spectrum: m/z=248 [M−H⁻]

EXAMPLE VI 5,6-diethoxy-2-indolinone 1.4 g of 4,5-diethoxy-2-nitro-phenylacetic acid are dissolved in 50 ml of acetic acid, 0.3 g of 10% palladium on carbon is added and the mixture is hydrogenated for 1 hour at ambient temperature and 50 psi. The catalyst is filtered off and the filtrate is concentrated by evaporation.

Yield: 1.15 g (100% of theory), $R_f$ value: 0.5 (silica gel, toluene/ethyl acetate/ethanol=4:2:1)

The following compounds are prepared analogously to Example VI:

(1) 6-trifluoromethyl-2-indolinone

Prepared from 2-nitro-4-trifluoromethyl-phenylacetic acid (2) 6-bromo-2-indolinone Prepared from 4-bromo-6-nitro-phenylacetic acid (according to Chem. Pharm. bull. (1985), 33, 1414–1418)

EXAMPLE VII 6-phenyl-2-indolinone 2.4 g of 6-bromo-2-indolinone are placed in 60 ml of dimethoxyethane, 1.9 g of phenylboric acid in 8 ml of ethanol and 0.3 g of tetrakistriphenylphosphine palladium are added and to this mixture 12 ml of 2N sodium carbonate solution are added dropwise at ambient temperature. The mixture is stirred for 6 hours at 85° C. After cooling the catalyst is filtered off, the solvent is eliminated and the residue is washed with 100 ml of water and 20 ml of 1N sodium hydroxide solution. The residue is purified through a silica gel column with petroleum ether/ethyl acetate (8:2) as eluant.

Yield: 1.5 g (65% of theory), $R_f$ value: 0.45 (silica gel, petroleum ether/ethyl acetate= 1:1)

Melting point: 167–170° C.

The following compound is prepared analogously to Example VII:

(1) 6-(2-Tolyl)-2-indolinone

Prepared from 6-bromo-2-indolinone and 2-tolylboric acid

EXAMPLE VIII 1-acetyl-5,6-dimethoxy-2-indolinone 16.0 g of 5,6-dimethoxy-2-indolinone (according to Hahn; Tulus; Chem. Ber. 74, 500 (1941)) are dissolved in 170 ml of acetic anhydride and stirred for more than 3 hours at 130° C. After cooling the residue is filtered off, washed with ether and dried in vacuo at 100° C.

Yield: 15.8 g (81% of theory), $R_f$ value: 0.8 (silica gel, methylene chloride/methanol= 10:1) $C_{12}H_{13}NO_4$ ESI mass spectrum: m/z=234 [M−H⁻]

The following compounds are prepared analogously to Example VIII:

(1) 1-acetyl-6-methoxy-2-indolinone

Prepared from 6-methoxy-2-indolinone (prepared according to Quallich, G. J.; Morrissey, P. M.; Synthesis 1993, 51) and acetic anhydride (2) 1-acetyl-5,6-diethoxy-2-indolinone Prepared from 5,6-diethoxy-2-indolinone and acetic anhydride (3) 1-acetyl-6-trifluoromethyl-2-indolinone Prepared from 6-trifluoromethyl-2-indolinone and acetic anhydride

EXAMPLE IX 1-acetyl-3-(1-ethoxy-1-phenylmethylidene)-5,6-dimethoxy-2-indolinone 10.0 g of 1-acetyl-5,6-dimethoxy-2-indolinone, 29.2 ml of triethyl orthobenzoate and 100 ml of acetic anhydride are stirred for 48 hours at 120° C. The solvent is eliminated and the residue evaporated with toluene, combined with ether and the precipitate formed (starting compounds is suction filtered. The filtrate is concentrated by evaporation and separated through a silica gel column with toluene, then with toluene/ethyl acetate (10:1). The product is triturated with ether, suction filtered and dried in vacuo at 100° C.

Yield: 1.4 g (9% of theory), $R_f$ value: 0.5 (silica gel, toluene/ethyl acetate 5:1) $C_{21}H_{21}NO_5$ ESI mass spectrum: m/z=390 [M+Na⁺]

The following compounds are prepared analogously to Example IX:

(1) 1-acetyl-3-(1-ethoxy-1-phenyl-methylidene)-6-methoxy-2-indolinone

Prepared from 1-acetyl-6-methoxy-2-indolinone, triethyl orthobenzoate and acetic anhydride (2) 1-acetyl-3-(1-ethoxy-1-ethyl-methylidene)-5,6-dimethoxy-2-indolinone Prepared from 1-acetyl-5,6-dimethoxy-2-indolinone, triethyl orthopropionate and acetic anhydride (3) 1-acetyl-3-(1-ethoxy-1-phenyl-methylidene)-5,6-diethoxy-2-indolinone Prepared from 1-acetyl-5,6-diethoxy-2-indolinone, triethyl orthopropionate and acetic anhydride (4) 1-acetyl-3-(1-ethoxy-1-phenyl-methylidene)-6-phenyl-2-indolinone Prepared from 6-phenyl-2-indolinone, triethyl orthopropionate and acetic anhydride (5) 1-acetyl-3-(1-ethoxy-1-phenyl-methylidene)-6-(2-tolyl)-2-indolinone Prepared from 6-(2-tolyl)-2-indolinone, triethyl orthopropionate and acetic anhydride

EXAMPLE X 1-acetyl-3-[1-hydroxy-1-(3-cyanophenyl)-methylidene]-5,6-dimethoxy-2-indolinone 2.0 g of 1-acetyl-5,6-dimethoxy-2-indolinone, 1.3 g of 2-cyanobenzoic acid, 3.3 g of TBTU, 1.6 g of HOBt and 7.5 ml of N-ethyl-diisopropylamine are dissolved in 30 ml of dimethylformamide and stirred for two days at ambient temperature. After this time the solution is combined with 400 ml of water and 20 ml of saturated potassium hydrogen sulphate solution. The precipitate formed is suction filtered, washed with water, a little methanol and a little ether and dried in vacuo at 100° C.

Yield: 2.6 g (84% of theory), $R_f$ value: 0.8 (silica gel, methylene chloride/methanol= 5:1) $C_2OH_{16}N_2O_5$ ESI mass spectrum: m/z=363 [M−H⁻]

The following compound is prepared analogously to Example X:

(1) 1-acetyl-3-(1-hydroxy-1-phenyl-methylidene)-6-trifluoromethyl-2-indolinone

Prepared from 1-acetyl-6-trifluoromethyl-2-indolinone and benzoic acid

EXAMPLE XI 1-acetyl-3-[1-chloro-1-(3-cyanophenyl)-methylidene]-5,6-dimethoxy-2-indolinone 2.5 g of 1-acetyl-3-[1-chloro-1-(3-cyanophenyl)-methylidene]-5,6-dimethoxy-2-indolinone and 1.6 g of phosphorus pentachloride are dissolved in 30 ml of toluene and stirred for 1 hour at 80° C. The suspension is cooled, combined with 50 ml of ether and the precipitate formed is suction filtered. After washing with ether the residue is dried in vacuo at 50° C.

Yield: 1.5 g (56% of theory), $R_f$ value: 0.6 (silica gel, methylene chloride/methanol= 40:1) $C_{20}H_{15}ClN_2O_4$ ESI mass spectrum: m/z=405/407 [M+Na⁺]

The following compound is prepared analogously to Example XI:
(1) 1-acetyl-3-(1-chloro-1-phenyl-methylidene)-6-trifluoromethyl-2-indolinone Prepared from 1-acetyl-3-(1-hydroxy-1-phenyl-methylidene)-6-trifluoromethyl-2-indoline and phosphorus pentachloride

EXAMPLE XII 3-(1-methoxy-1-phenyl-methylidene)-5,6-methylenedioxy-2-indolinone Under a nitrogen atmosphere 4.5 g of diethyl-1-methoxybenzylphosphonate (according to Burkhouse, D.; Zimmer, H.; Synthesis 1984, 330) are dissolved in 40 ml of absolute dimethylformamide and at −40° C. 4.0 g of potassium-tert-butoxide are added batchwise and stirred for 15 minutes at −10° C. 3.0 g of 5,6-methylenedioxyisatin (according to Lackey, K.; Sternbach, D. D.; Synthesis 1993, 993) are added to the clear solution and stirred for 1 hour at ambient temperature. After this time the mixture is poured into 20 ml of ice-cold saturated potassium hydrogen sulphate solution and extracted with ethyl acetate. The ethyl acetate phase is washed with water, dried over sodium sulphate and concentrated by evaporation. Finally the residue is separated through a silica gel column with toluene/ethyl acetate (5:1). The product obtained can be recrystallised from ether.

Yield: 1.6 g (35% of theory), $R_f$ value: 0.3 (silica gel, toluene/ethyl acetate=5:1) $C_{17}H_{13}NO_4$ ESI mass spectrum: m/z=318 [M+Na$^+$]

EXAMPLE XIII 1-acetoxy-3-(1-ethoxy-1-phenylmethylidene)-6-nitro-2-indolinone 300 mg of 1-hydroxy-6-nitro-2-indolinone are dissolved in 4.0 ml of acetic anhydride and 4.0 ml of triethyl orthobenzoate, stirred for 6 hours at 110° C., concentrated by evaporation and purified through a silica gel column with methylene chloride as eluant.

Yield: 0.28 g (49% of theory), $R_f$ value: 0.23 (silica gel, methylene chloride) $C_{19}H_{16}N_2O_6$ Mass spectrum: m/z=368 [M$^+$]

EXAMPLE XIV 3-(Z)-{1-[4-(piperidin-1-yl-methyl)-anilino]-1-phenyl-methylidene}6-nitro-2-indolinone 1.25 g of 1-acetoxy-3-(1-ethoxy-1-phenyl-methylidene)-6-nitro-2-indolinone and 0.65 g of 4-(piperidin-1-yl-methyl)-aniline are dissolved in 10 ml of dimethylformamide and stirred for 30 minutes at ambient temperature. After this time 46 mg of palladium on carbon (10%) are added and carefully hydrogenated for 1 hour at ambient temperature with 3 bar hydrogen. The catalyst is filtered off, the filtrate concentrated by evaporation and the residue purified through a silica gel column with methylene chloride/methanol (9:1).

Yield: 16 mg of (4% of theory), $R_f$ value: 0.4 (silica gel, methylene chloride/methanol= 9:1) $C_{27}H_{26}N_4O_3$ The following compound is prepared analogously to Example XIV:
(1) 1-acetoxy-3-(Z)-[1-(4-methoxycarbonyl-anilino)-1-phenyl-methylidene]-6-nitro-2-indolinone Prepared from 1-acetoxy-3-(1-ethoxy-1-phenyl-methylidene)-6-nitro-2-indolinone and methyl 4-aminobenzoate without subsequent hydrogenation ESI mass spectrum: m/z=472 [M−H$^-$]

EXAMPLE XV

N-(2-dimethylamino-ethyl)-N-methylsulphonyl-4-nitroaniline 38.9 g of N-methylsulphonyl-4-nitroaniline are dissolved in 2.0 l of acetone, 51.9 g of 1-chloro-2-dimethylamino-ethane, 77.4 g of potassium carbonate and 5.0 g of sodium iodide added and the mixture is stirred for a total of 4 days at 50° C., adding, after 12 hours, a further 25.9 g of 1-chloro-2-dimethylamino-ethane, 49.8 g of potassium carbonate and 5.0 g of sodium iodide in 500 ml of acetone and, after 36 hours, a further 26.0 g of 1-chloro-2-dimethylamino-ethane, 50.0 g of potassium carbonate and 5.0 g of sodium iodide in 100 ml of acetone. After this time the mixture is filtered and the filtrate is evaporated down. The residue is stirred with ether, suction filtered and dried at 40° C.

Yield: 25.3 g (49% of theory), $R_f$ value: 0.5 (silica gel, methylene chloride/methanol/ammonia=9:1:0.1) $C_{11}H_{17}N_3O_4S$ ESI mass spectrum: m/z=288 [M+H$^+$]

The following compound is prepared analogously to Example XV:
(1) N-carboxymethyl-N-methylsulphonyl-4-nitroaniline

EXAMPLE XVI

N-(dimethylaminocarbonyl-methyl)-N-methylsulphonyl-4-nitroaniline 7.0 g of N-carboxymethyl-N-methylsulphonyl-4-nitroaniline, 2.5 g of dimethylamine hydrochloride, 8.1 g of TBTU and 3.9 g of HOBT are dissolved in 125 ml of dimethylformamide and at 0° C. 17.6 ml of N-ethyl-diisopropylamine are added. The mixture is stirred for 4 hours at ambient temperature, diluted with 1 l water and the precipitate formed is suction filtered. After washing with water, ethanol and ether the residue is dried at 70° C. in vacuo.

Yield: 5.3 g (69% of theory), $R_f$ value: 0.40 (silica gel, methylene chloride/methanol= 9:1) $C_{11}H_{15}N_3O_5S$ ESI mass spectrum: m/z=300 [M−H$^-$]

The following compound is prepared analogously to Example XVI:
(1) N-[(2-dimethylamino-ethylamino)-carbonylmethyl]-N-methyl-sulphonyl-4-nitroaniline

EXAMPLE XVII

N-(dimethylaminomethylcarbonyl)-N-methyl-4-nitro-aniline 1.8 g of dimethylamine hydrochloride and 5.5 g of potassium carbonate are placed in 80 ml of acetone and 4.2 g of N-(2-bromomethylcarbonyl)-N-methyl-4-nitroaniline (prepared according to Chem. Ber. 119, 2430 (1986)) are added in three batches at ambient temperature. The mixture is stirred for 12 hours at ambient temperature. After this time the mixture is filtered and the filtrate is concentrated by evaporation. The residue is dissolved in ethyl acetate, washed twice with water, dried over sodium sulphate and finally concentrated by rotary evaporation.

Yield: 2.8 g (79% of theory), $R_f$ value: 0.5 (silica gel, ethyl acetate/methanol=7:3)

Melting point: 121–122° C.

EXAMPLE XVIII 4-(piperidin-1-yl-methyl)-nitrobenzene 40.0 g of 4-nitrobenzylbromide are in 500 ml of methylene chloride dissolved, 51.5 ml of triethylamine are added and 18.3 ml of piperidine are carefully added dropwise. After the end of the exothermic reaction the mixture is refluxed for a further 30 minutes. After cooling it is washed with water and the organic phase is dried over sodium sulphate. Finally, the organic phase is evaporated down.

Yield: 36.3 g (89% of theory), $R_f$ value: 0.6 (silica gel, methylene chloride/methanol=9:1) $C_{12}H_{16}N_2O_2$ Mass spectrum: m/z=221 [M$^+$]

The following compounds are prepared analogously to Example XVIII:
(1) 4-[(N-benzyl-N-methyl-amino)-methyl]-nitrobenzene
(2) 3-(dimethylaminomethyl)-nitrobenzene
(3) 4-(dimethylaminomethyl)-nitrobenzene
(4) 4-(2-dimethylamino-ethyl)-nitrobenzene
(5) 4-[2-(4-ethoxycarbonyl-piperidin-1-yl)-ethyl]-nitrobenzene
(6) 4-[(2,6-dimethyl-piperidin-1-yl)-methyl]-nitrobenzene
(7) 4-(pyrrolidin-1-yl-methyl)-nitrobenzene

EXAMPLE IXX 4-(4-methyl-piperazin-1-yl)-nitrobenzene 31.5 g of 4-chloro-1-nitrobenzene and 44.4 ml of 1-methyl-piperazine are combined and stirred for 18 hours at 90° C. Then the solution is poured onto ice water and the precipitate formed is suction filtered, washed with water and recrystallised from ethanol/water (1:1). The residue is dried in vacuo at 75° C.

Yield: 44.0 g (99% of theory), $R_f$ value: 0.5 (silica gel, methylene chloride/methanol=10:1)

Melting point: 108–112° C.

The following compounds are prepared analogously to Example IX:
(1) N-(2-dimethylaminoethyl)-N-methyl-4-nitroaniline
  Prepared from 1-fluoro-4-nitrobenzene and 1-dimethylamino-2-methylamino-ethane
(2) N-(3-dimethylaminopropyl)-N-methyl-4-nitroaniline
  Prepared from 1-fluoro-4-nitrobenzene and 1-dimethylamino-3-methylamino-propane

EXAMPLE XX

4-[N-acetyl-(2-dimethylaminoethyl)-amino]-nitrobenzene 3.6 g of 4-(2-dimethylamino-ethylamino)-nitrobenzene (according to Gabbay et al., J. Am. Chem. Soc. 91, 5136 (1969)) are dissolved in 50 ml of methylene chloride and 5.0 ml of triethylamine are added. To this mixture 1.3 ml of acetylchloride are slowly added dropwise at ambient temperature and the mixture is stirred for 2 hours at ambient temperature. After this time a further 5.0 ml of triethylamine and 1.3 ml of acetylchloride are added and the mixture is refluxed for a further 2 hours. The solvent is eliminated in vacuo, the residue is taken up in ethyl acetate and the organic phase is extracted twice with water. After drying over magnesium sulphate the solvent is eliminated and the residue is dried in vacua.

Yield: 2.0 g (45% of theory), $R_f$ value: 0.55 (silica gel, methylene chloride/methanol/ammonia=9:1:0.1) $C_{12}H_{17}N_3O_3$ ESI mass spectrum: m/z=252 [M+H$^+$]

The following compounds are prepared analogously to Example XX:
(1) 4-[N-acetyl-N-(3-dimethylaminopropyl)-amino]-nitrobenzene
  Prepared from 4-(3-dimethylamino-propylamino)-nitrobenzene and acetylchloride
(2) 4-[N-propionyl-N-(2-dimethylaminoethyl)-amino]-nitrobenzene
  Prepared from 4-(2-dimethylamino-ethylamino)-nitrobenzene and propionylchloride
(3) 4-[N-propionyl-N-(3-dimethylaminopropyl)-amino]-nitrobenzene
  Prepared from 4-(3-dimethylamino-propylamino)-nitrobenzene and propionylchloride

EXAMPLE XXI 4-nitro-N,N-dimethylbenzamide 10.0 g of 4-nitrobenzoic acid, 8.4 g of dimethylamine hydrochloride and 18.3 g of TBTU are placed in 50 ml of dimethylformamide, 78.4 ml of N-ethyl-diisopropylamine are added at ambient temperature and the mixture is stirred for 15 hours at ambient temperature. After this time the mixture is combined with water and extracted with ethyl acetate. The organic phase is again extracted with water and with 1N hydrochloric acid, dried over sodium sulphate and concentrated by evaporation. The product is recrystallised from ether.

Yield: 5.6 g (48% of theory), $R_f$ value: 0.6 (silica gel, methylene chloride/methanol=9:1)

Melting point: 61–63° C.

The following compound is prepared analogously to Example XXI:
(1) 4-(piperidin-1-yl-carbonyl)-nitrobenzene
  Prepared from 4-nitrobenzoic acid and piperidine

EXAMPLE XXII 4-(piperidin-1-yl-methyl)-aniline 37.0 g of 4-(piperidin-1-yl-methyl)-nitrobenzene are dissolved in 300 ml of methanol, 8.0 g of Raney nickel are added and the mixture is hydrogenated for 1 hour 25 minutes with 3 bar hydrogen at ambient temperature. The catalyst is filtered off and the filtrate is concentrated by evaporation.

Yield: 24.0 g (75% of theory), $R_f$ value: 0.4 (silica gel, methylene chloride/methanol=9:1) $C_{12}H_{18}N_2$ ESI mass spectrum: m/z=191 [M+H$^+$]

The following compounds are prepared analogously to Example XXII:

(1) 4-[(N-benzyl-N-methyl-amino)-methyl]-aniline
(2) N-(2-dimethylamino-ethyl)-N-methylsulphonyl-p-phenylenediamine
(3) 3-(dimethylaminomethyl)-aniline
(4) 4-(dimethylaminomethyl)-aniline
(5) 4-(2-dimethylamino-ethyl)-aniline
(6) N-(dimethylaminomethylcarbonyl)-N-methyl-p-phenylenediamine
(7) 4-[2-(4-ethoxycarbonyl-piperidin-1-yl)-ethyl]-aniline
(8) N-(dimethylaminocarbonylmethyl)-N-methylsulphonyl-p-phenylenediamine
(9) 4-[(2,6-dimethyl-piperidin-1-yl)-methyl]-aniline
(10) N-[(2-dimethylamino-ethylamino)-carbonylmethyl]-N-methyl-sulphonyl-p-phenylenediamine
(11) 4-(pyrrolidin-1-yl-methyl)-aniline
(12) 4-(4-methyl-piperazin-1-yl)-aniline
(13) N-(2-dimethylaminoethyl)-N-methyl-p-phenylenediamine
(14) N-(3-dimethylaminopropyl)-N-methyl-p-phenylenediamine
(15) N-acetyl-N-(2-dimethylaminoethyl)-p-phenylenediamine
(16) N-acetyl-N-(3-dimethylaminopropyl)-p-phenylenediamine
(17) N-propionyl-N-(2-dimethylaminoethyl)-p-phenylenediamine
(18) N-propionyl-N-(3-dimethylaminopropyl)-p-phenylenediamine
(19) N-methylsulphonyl-p-phenylenediamine
(20) 4-amino-N,N-dimethylbenzamide
(21) 4-(piperidin-1-yl-carbonyl)-aniline
(22) 4-tetrazol-5-yl-aniline Preparation of the final compounds:

EXAMPLE 1

3-(Z)-{1-[4-(piperidin-1-yl-methyl)-anilino]-1-phenyl-methylidene}-5,6-dimethoxy-2-indolinone 700 mg of 1-acetyl-3-(1-ethoxy-1-phenyl-methylidene)-5,6-dimethoxy-2-indolinone and 300 mg of 4-(piperidin-1-yl-methyl)-aniline are suspended in 3.0 ml of dimethylformamide and stirred for 2 hours at 110° C. After cooling 1.0 ml of piperidine is added and the mixture is stirred for 3 hours at ambient temperature, combined with water and the precipitate formed is suction filtered. The precipitate is separated through a silica gel column with methylene chloride/methanol/ammonia (10:1:0.01), stirred with ether, suction filtered and dried at 100° C.

Yield: 300 mg of (55% of theory), $R_f$ value: 0.4 (silica gel, methylene chloride/methanol= 5:1) $C_{29}H_{29}N_3O_4$ Mass spectrum: m/z=469 [M⁺]

The following compounds are prepared analogously to Example 1:

(1) 3-(Z)-[1-(4-methoxy-anilino)-1-phenyl-methylidene]-5,6-dimethoxy-2-indolinone
Prepared from 1-acetyl-3-(1-ethoxy-1-phenyl-methylidene)-5,6-dimethoxy-2-indolinone and p-anisidine
$R_f$ value: 0.4 (silica gel, methylene chloride/methanol= 10:1) $C_{24}H_{22}N_2O_4$
Mass spectrum: m/z=402 [M⁺]

(2) 3-(Z)-[1-(4-chloro-anilino)-1-phenyl-methylidene]-5,6-dimethoxy-2-indolinone
Prepared from 1-acetyl-3-(1-ethoxy-1-phenyl-methylidene)-5,6-dimethoxy-2-indolinone and 4-chloroaniline
$R_f$ value: 0.5 (silica gel, methylene chloride/methanol= 10:1) $C_{23}H_{19}ClN_2O_3$
Mass spectrum: m/z=406/408 [M⁺]

(3) 3-(Z)-(1-{4-[(N-benzyl-N-methyl-amino)-methyl]-anilino}-1-phenyl-methylidene)-5,6-dimethoxy-2-indolinone
Prepared from 1-acetyl-3-(1-ethoxy-1-phenyl-methylidene)-5,6-dimethoxy-2-indolinone and 4-[(N-benzyl-N-methyl-amino)-methyl]-aniline
$R_f$ value: 0.5 (silica gel, methylene chloride/methanol= 10:1) $C_{32}H_{31}N_3O_3$
Mass spectrum: m/z=505 [M⁺]

(4) 3-(Z)-(1-{4-[N-(2-dimethylaminoethyl)-N-methylsulphonyl-amino]-anilino}-1-phenyl-methylidene)-5,6-dimethoxy-2-indolinone
Prepared from 1-acetyl-3-(1-ethoxy-1-phenyl-methylidene)-5,6-dimethoxy-2-indolinone and N-(2-dimethylamino-ethyl)-N-methylsulphonyl-p-phenylenediamine
$R_f$ value: 0.5 (aluminium oxide, methylene chloride/methanol=20:1) $C_{28}H_{32}N_4O_5S$
Mass spectrum: m/z=536 [M⁺]

(5) 3-(Z)-{1-[3-(dimethylamino-methyl)-anilino]-1-phenyl-methylidene)-5,6-dimethoxy-2-indolinone
Prepared from 1-acetyl-3-(1-ethoxy-1-phenyl-methylidene)-5,6-dimethoxy-2-indolinone and 3-(dimethylaminomethyl)-aniline
$R_f$ value: 0.4 (silica gel, methylene chloride/methanol= 5:1) $C_{26}H_{27}N_3O_3$
Mass spectrum: m/z=429 [M⁺]

(6) 3-(Z)-(1-(4-(dimethylaminomethyl)-anilino]-1-phenyl-methylidene}-5,6-dimethoxy-2-indolinone
Prepared from 1-acetyl-3-(1-ethoxy-1-phenyl-methylidene)-5,6-dimethoxy-2-indolinone and 4-(dimethylaminomethyl)-aniline
$R_f$ value: 0.5 (silica gel, methylene chloride/methanol/ ammonia=10:1:1) $C_{26}H_{27}N_3O_3$
Mass spectrum: m/z=429 [M⁺]

(7) 3-(Z)-{1-[4-(2-dimethylamino-ethyl)-anilino]-1-phenyl-methylidene}-5,6-dimethoxy-2-indolinone
Prepared from 1-acetyl-3-(1-ethoxy-1-phenyl-methylidene)-5,6-dimethoxy-2-indolinone and 4-(2-dimethylamino-ethyl)-aniline
$R_f$ value: 0.6 (silica gel, methylene chloride/methanol/ ammonia 5:1:0.01) $C_{27}H_{29}N_3O_3$
Mass spectrum: m/z=443 [M⁺]

(8) 3-(Z)-{1-[4-(N-dimethylaminomethylcarbonyl-N-methyl-amino)-anilino]-1-phenyl-methylidene}-5,6-dimethoxy-2-indolinone
Prepared from 1-acetyl-3-(1-ethoxy-1-phenyl-methylidene)-5,6-dimethoxy-2-indolinone and N-(dimethylaminomethylcarbonyl)-N-methyl-p-phenylenediamine
$R_f$ value: 0.5 (silica gel, methylene chloride/methanol= 10:1) $C_{28}H_{30}N_4O_4$
Mass spectrum: m/z=486 [M⁺]

(9) 3-(Z)-{1-[4-(1H-imidazol-4-yl)-anilino]-1-phenyl-methylidene}-5,6-dimethoxy-2-indolinone
Prepared from 1-acetyl-3-(1-ethoxy-1-phenyl-methylidene)-5,6-dimethoxy-2-indolinone and 4-(1H-imidazo-4-yl)-aniline (prepared according to Chem. Pharm. bull. 38, 1803 (1990))

R_f value: 0.5 (silica gel, methylene chloride/methanol= 10:1) $C_{26}H_{22}N_4O_3$
ESI mass spectrum: m/z=439 [M+H$^+$]

(10) 3-(Z)-(1-{4-[2-(4-carboxyethyl-piperidin-1-yl)-ethyl]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and 4-[2-(4-ethoxycarbonyl-piperidin-1-yl)-ethyl]-aniline R_f value: 0.5 (silica gel, methylene chloride/methanol= 10:1) $C_{33}H_{37}N_3O_5$
ESI mass spectrum: m/z=554 [M−H$^-$]

(11) 3-(Z)-(1-{4-[N-(dimethylaminocarbonylmethyl)-N-methyl-sulphonyl-amino]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and N-(dimethylaminocarbonylmethyl)-N-methylsulphonyl-p-phenylenediamine R_f value: 0.5 (silica gel, methylene chloride/methanol= 10:1) $C_{28}H_{30}N_4O_6S$
Mass spectrum: m/z=550 [M$^+$]

(12) 3-(Z)-[1-(4-ethoxycarbonyl-anilino)-1-phenyl-methylidene]-5,6-dimethoxy-2-indolinone Prepared from 1-acetyl-3-(1-ethoxy-1-phenyl-methylidene)-5,6-dimethoxy-2-indolinone and ethyl 4-aminobenzoate R_f value: 0.5 (silica gel, methylene chloride/ethanol= 20:1) $C_{26}H_{24}N_2O_5$
Mass spectrum: m/z=444 [M$^+$]

(13) 3-(Z)-(1-{4-[(2,6-dimethyl-piperidin-1-yl)-methyl]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and 4-[(2,6-dimethyl-piperidin-1-yl)-methyl]-aniline R_f value: 0.5 (silica gel, methylene chloride/methanol/ammonia=10:1:0.01) $C_{31}H_{35}N_3O_3$
Mass spectrum: m/z=497 [M$^+$]

(14) 3-(Z)-[1-(4-{N-[(2-dimethylamino-ethylamino)-carbonyl-methyl]N-methylsulphonyl-amino}-anilino)-1-phenyl-methylidene]-5,6-dimethoxy-2-indolinone Prepared from 1-acetyl-3-(1-ethoxy-1-phenyl-methylidene)-5,6-dimethoxy-2-indolinone and N-[(2-dimethylamino-ethylamino)-carbonylmethyl]-N-methylsulphonyl-p-phenylenediamine R_f value: 0.3 (silica gel, methylene chloride/methanol= 4:1) $C_{30}H_{35}N_5O_6S$
Mass spectrum: m/z=593 [M$^+$]

(15) 3-(Z)-{1-[4-(pyrrolidin-1-yl-methyl)-anilino]-1-phenyl-methylidene}-5,6-dimethoxy-2-indolinone Prepared from 1-acetyl-3-(1-ethoxy-1-phenyl-methylidene)-5,6-dimethoxy-2-indolinone and 4-(pyrrolidin-1-yl-methyl)-aniline R_f value: 0.4 (silica gel, methylene chloride/methanol= 5:1) $C_{28}H_{29}N_3O_3$
Mass spectrum: m/z=455 [M$^+$]

(16) 3-(Z)-{1-[4-(4-methyl-piperazin-1-yl)-anilino]-1-phenyl-methylidene}-5,6-dimethoxy-2-indolinone Prepared from 1-acetyl-3-(1-ethoxy-1-phenyl-methylidene)-5,6-dimethoxy-2-indolinone and 4-(4-methyl-piperazin-1-yl)-aniline R_f value: 0.4 (silica gel, methylene chloride/methanol= 10:1) $C_{28}H_{30}N_4O_3$
Mass spectrum: m/z=470 [M$^+$]

(17) 3-(Z)-(1-{4-[N-acetyl-N-(2-dimethylamino-ethyl)-amino]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and N-acetyl-N-(2-dimethylamino-ethyl)-p-phenylenediamine R_f value: 0.5 (silica gel, methylene chloride/methanol= 9:1) $C_{29}H_{32}N_4O_4$
ESI mass spectrum: m/z=499 [M−H$^-$]

(18) 3-(Z)-(1-{4-[N-acetyl-N-(3-dimethylamino-propyl)-amino]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and N-acetyl-N-(3-dimethylamino-propyl)-p-phenylenediamine R_f value: 0.45 (silica gel, methylene chloride/methanol= 10:1) $C_{30}H_{34}N_4O_4$
ESI mass spectrum: m/z=515 [M+H$^+$]

(19) 3-(Z)-(1-{4-[N-propionyl-N-(2-dimethylamino-ethyl)-amino]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and N-propionyl-N-(2-dimethylamino-ethyl)-p-phenylenediamine R_f value: 0.5 (silica gel, methylene chloride/methanol= 9:1) $C_{30}H_{34}N_4O_4$
ESI mass spectrum: m/z=515 [M+H$^+$]

(20) 3-(Z)-(1-{4-[N-propionyl-N-(3-dimethylamino-propyl)-amino]-anilino}-1-phenyl-methylidene)-5,6-dimethoxy-2-indolinone Prepared from 1-acetyl-3-(1-ethoxy-1-phenyl-methylidene)-5,6-dimethoxy-2-indolinone and N-propionyl-N-(3-dimethylamino-propyl)-p-phenylenediamine R_f value: 0.5 (silica gel, methylene chloride/methanol= 10:1) $C_{31}H_{36}N_4O_4$
ESI mass spectrum: m/z=529 [M+H$^+$]

(21) 3-(Z)-[1-(4-aminocarbonyl-anilino)-1-phenyl-methylidene]-5,6-dimethoxy-2-indolinone Prepared from 1-acetyl-3-(1-ethoxy-1-phenyl-methylidene)-5,6-dimethoxy-2-indolinone and 4-aminobenzamide R_f value: 0.4 (silica gel, toluene/ethyl acetate/ethanol= 4:2:1) $C_{24}H_{21}N_3O_4$
ESI mass spectrum: m/z=414 [M−H$^-$]

(22) 3-(Z)-[1-{4-dimethylaminocarbonyl-anilino)-1-phenyl-methylidene]-5,6-dimethoxy-2-indolinone Prepared from 1-acetyl-3-(1-ethoxy-1-phenyl-methylidene)-5,6-dimethoxy-2-indolinone and 4-amino-dimethylbenzamide R_f value: 0.4 (silica gel, toluene/ethyl acetate/ethanol= 4:2:1) $C_{26}H_{25}N_3O_4$
ESI mass spectrum: m/z=442 [M−H$^-$]

(23) 3-(Z)-(1-[4-(piperidin-1-yl-carbonyl)-anilino)-1-phenyl-methylidene}-5,6-dimethoxy-2-indolinone Prepared from 1-acetyl-3-(1-ethoxy-1-phenyl-methylidene)-5,6-dimethoxy-2-indolinone and 4-(piperidin-1-yl-carbonyl)-aniline R_f value: 0.4 (silica gel, toluene/ethyl acetate/ethanol= 4:2:1) $C_{29}H_{29}N_3O_4$
ESI mass spectrum: m/z=482 [M−H$^-$]

(24) 3-(Z)-[1-(4-ethoxycarbonylmethyl-anilino)-1-phenyl-methylidene]-5,6-dimethoxy-2-indolinone Prepared from 1-acetyl-3-(1-ethoxy-1-phenyl-methylidene)-5,6-dimethoxy-2-indolinone and ethyl 4-aminophenylacetate $R_f$ value: 0.5 (silica gel, petroleum ether/ethyl acetate/ethanol=7:2:1) $C_{22}H_{26}N_2O_5$
ESI mass spectrum: m/z=457 [M−H⁻]

(25) 3-(Z)-{1-[4-(tetrazol-5-yl)-anilino]-1-phenyl-methylidene}-5,6-dimethoxy-2-indolinone Prepared from 1-acetyl-3-(1-ethoxy-1-phenyl-methylidene)-5,6-dimethoxy-2-indolinone and 4-tetrazol-5-yl-aniline $R_f$ value: 0.4 (silica gel, toluene/ethyl acetate/ethanol=4:2:1) $C_{24}H_{20}N_6O_3$
ESI mass spectrum: m/z=439 [M−H⁻]

(26) 3-(Z)-[1-anilino-1-(3-cyanophenyl)-methylidene]-5,6-dimethoxy-2-indolinone

Prepared from 1-acetyl-3-(1-chloro-1-(3-cyanophenyl)-methylidene]-5,6-dimethoxy-2-indolinone and aniline $R_f$ value: 0.5 (silica gel, methylene chloride/methanol=10:1) $C_{24}H_{19}N_3O_3$
ESI mass spectrum: m/z=396 [M−H⁻]

(27) 3-(Z)-{1-[4-(piperidin-1-yl-methyl)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and 4-(piperidin-1-yl-methyl)-aniline $R_f$ value: 0.4 (silica gel, methylene chloride/methanol=5:1) $C_{25}H_{31}N_3O_3$
Mass spectrum: m/z=421 [M⁺]

(28) 3-(Z)-{1-[4-(dimethylaminomethyl)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and 4-(dimethylaminomethyl)-aniline $R_f$ value: 0.5 (silica gel, methylene chloride/methanol=5:1) $C_{22}H_{27}N_3O_3$
Mass spectrum: m/z=381 [M⁺]

(29) 3-(Z)-(1-anilino-1-ethyl-methylidene)-5,6-dimethoxy-2-indolinone

Prepared from 1-acetyl-3-(1-ethoxy-1-ethyl-methylidene)-5,6-dimethoxy-2-indolinone and aniline $R_f$ value: 0.3 (silica gel, methylene chloride/methanol=20:1) $C_{19}H_{20}N_2O_3$
Mass spectrum: m/z=324 [M⁺]

(30) 3-(Z)-(1-{4-[N-(2-dimethylamino-ethyl)-N-methylsulphonyl amino)-anilino}-1-ethyl-methylidene)-5,6-dimethoxy-2-indolinone Prepared from 1-acetyl-3-(1-ethoxy-1-ethyl-methylidene)-5,6-dimethoxy-2-indolinone and N-(2-dimethylamino-ethyl)-N-methylsulphonyl-p-phenylenediamine $R_f$ value: 0.4 (Alox, methylene chloride/ethanol=20:1) $C_{24}H_{32}N_4O_5S$
ESI mass spectrum: m/z=489 [M+H⁺]

(31) 3-(Z)-(1-{4-[N-(2-dimethylaminoethyl))-N-methyl-amino]-anilino}-1-ethyl-methylidene)-5,6-dimethoxy-2-indolinone Prepared from 1-acetyl-3-(1-ethoxy-1-ethyl-methylidene)-5,6-dimethoxy-2-indolinone and N-(2-dimethylaminoethyl)-N-methyl-p-phenylenediamine $R_f$ value: 0.5 (silica gel, methylene chloride/methanol=5:1) $C_{24}H_{32}N_4O_3$
ESI mass spectrum: m/z=425 [M+H⁺]

(32) 3-(Z)-(1-{4-(N-(3-dimethylaminopropyl)-N-methyl-amino]-anilino}-1-ethyl-methylidene)-5,6-dimethoxy-2-indolinone Prepared from 1-acetyl-3-(1-ethoxy-1-ethyl-methylidene)-5,6-dimethoxy-2-indolinone and N-(3-dimethylaminopropyl)-N-methyl-p-phenylenediamine $R_f$ value: 0.6 (silica gel, methylene chloride/methanol/ammonia=5:1:0.01) $C_{25}H_{34}N_4O_3$
ESI mass spectrum: m/z=439 [M+H⁺]

(33) 3-(Z)-(1-{4-[N-acetyl-N-(3-dimethylaminopropyl)-amino]-anilino}-1-ethyl-methylidene)-5,6-dimethoxy-2-indolinone Prepared from 1-acetyl-3-(1-ethoxy-1-ethyl-methylidene)-5,6-dimethoxy-2-indolinone and N-acetyl-N-(3-dimethylamino-propyl)-p-phenylenediamine $R_f$ value: 0.4 (Alox, methylene chloride/ethanol=25:1) $C_{26}H_{34}N_4O_4$
ESI mass spectrum: m/z=467 [M+H⁺]

(34) 3-(Z)-{1-[4-(N-methylsulphonylamino)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and N-methylsulphonyl-p-phenylenediamine $R_f$ value: 0.5 (silica gel, methylene chloride/methanol=10:1) $C_{21}H_{25}N_3O_5S$
ESI mass spectrum: m/z=430 [M−H⁻]

(35) 3-(Z)-{1-[4-(N-acetylamino)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and N-acetyl-p-phenylenediamine $R_f$ value: 0.5 (silica gel, methylene chloride/methanol=9:1) $C_{22}H_{25}N_3O_4$
ESI mass spectrum: m/z=394 [M−H⁻]

(36) 3-(Z)-(1-{4-[N-(dimethylaminocarbonylmethyl)-N-methyl-sulphonyl-amino]-anilino}-1-ethyl-methylidene)-5,6-dimethoxy-2-indolinone Prepared from 1-acetyl-3-(1-ethoxy-1-ethyl-methylidene)-5,6-dimethoxy-2-indolinone and N-(dimethylaminocarbonylmethyl)-N-methylsulphonyl-p-phenylenediamine $R_f$ value: 0.5 (silica gel, methylene chloride/methanol=10:1) $C_{24}H_{30}N_4O_6S$
Mass spectrum: m/z=502 [M⁺]

(37) 3-(Z)-[1-(4-ethoxycarbonyl-anilino)-1-ethyl-methylidene]-5,6-dimethoxy-2-indolinone Prepared from 1-acetyl-3-(1-ethoxy-1-ethyl-methylidene)-5,6-dimethoxy-2-indolinone and ethyl 4-aminobenzoate $R_f$ value: 0.6 (silica gel, toluene/ethyl acetate/ethanol=4:2:1) $C_{22}H_{24}N_2O_5$
ESI mass spectrum: m/z=395 [M−H⁻]

(38) 3-(Z)-[1-(4-aminocarbonyl-anilino)-1-ethyl-methylidene]-5,6-dimethoxy-2-indolinone Prepared from 1-acetyl-3-(1-ethoxy-1-ethyl-methylidene)-5,6-dimethoxy-2-indolinone and 4-aminobenzamide $R_f$ value: 0.45 (silica gel, methylene chloride/methanol=9:1) $C_{20}H_{21}N_3O_4$
Mass spectrum: m/z=367 [M⁺]

(39) 3-(Z)-[1-(4-dimethylaminocarbonyl-anilino)-1-ethyl-methylidene]-5,6-dimethoxy-2-indolinone Prepared from 1-acetyl-3-(1-ethoxy-1-ethyl-methylidene)-5,6-dimethoxy-2-indolinone and 4-amino-dimethylbenzamide $R_f$ value: 0.5 (silica gel, methylene chloride/methanol=10:1) $C_{22}H_{25}N_3O_4$
ESI mass spectrum: m/z=394 [M−H⁻]

(40) 3-(Z)-{1-[4-(ethoxycarbonylmethyl)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and ethyl 4-aminophenylacetate $R_f$ value: 0.4 (silica gel, toluene/ethyl acetate/ethanol=4:2:1) $C_{23}H_{26}N_2O_5$
Mass spectrum: m/z=410 [M⁺]

(41) 3-(Z)-{1-[4-(tetrazol-5-yl)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and 4-tetrazol-5-yl-aniline $R_f$ value: 0.45 (silica gel, methylene chloride/methanol= 9:1) $C_{20}H_{20}N_6O_3$ ESI mass spectrum: m/z=391 [M−H⁻]

(42) 3-(Z)-{1-[4-(piperidin-1-yl-methyl)-anilino]-1-phenyl-methylidene}-5,6-methylenedioxy-2-indolinone Prepared from 3-(1-methoxy-1-phenyl-methylidene)-5,6-methylenedioxy-2-indolinone and 4-(piperidin-1-yl-methyl)-aniline $R_f$ value: 0.5 (silica gel, methylene chloride/methanol= 5:1) $C_{28}H_{27}N_3O_3$ Mass spectrum: m/z=453 [M⁺]

(43) 3-(Z)-{1-[4-(dimethylaminomethyl)-anilino]-1-phenyl-methylidene}-5,6-methylenedioxy-2-indolinone Prepared from 3-(1-methoxy-1-phenyl-methylidene)-5,6-methylenedioxy-2-indolinone and 4-(dimethylaminomethyl)-aniline $R_f$ value: 0.5 (silica gel, methylene chloride/methanol= 5:1) $C_{25}H_{23}N_3O_3$ Mass spectrum: m/z=413 [M⁺]

(44) 3-(Z)-(1-{4-[(N-benzyl-N-methyl-amino)-methyl]-anilino}-1-phenyl-methylidene)-5,6-methylenedioxy-2-indolinone Prepared from 3-(1-methoxy-1-phenyl-methylidene)-5,6-methylenedioxy-2-indolinone and 4-[(N-benzyl-N-methyl-amino)-methyl]-aniline $R_f$ value: 0.5 (silica gel, methylene chloride/methanol= 5:1) $C_{31}H_{27}N_3O_3$ Mass spectrum: m/z=489 [M⁺]

(45) 3-(Z)-(1-{4-[N-(2-dimethylaminoethyl)-N-methylsulphonyl-amino]-anilino}-1-phenyl-methylidene)-5,6-methylenedioxy-2-indolinone Prepared from 3-(1-methoxy-1-phenyl-methylidene)-5,6-methylenedioxy-2-indolinone and N-(2-dimethylamino-ethyl)-N-methylsulphonyl-p-phenylenediamine $R_f$ value: 0.6 (silica gel, methylene chloride/methanol= 5:1) $C_{27}H_{28}N_4O_5S$ Mass spectrum: m/z=520 [M⁺]

(46) 3-(Z)-{1-[4-(N-dimethylaminomethylcarbonyl-N-methyl-amino)-anilino]-1-phenyl-methylidene}-5,6-methylenedioxy-2-indolinone Prepared from 3-(1-methoxy-1-phenyl-methylidene)-5,6-methylenedioxy-2-indolinone and N-(dimethylaminomethylcarbonyl)-N-methyl-p-phenylenediamine $R_f$ value: 0.3 (silica gel, methylene chloride/methanol= 5:1) $C_{27}H_{26}N_4O_4$ Mass spectrum: m/z=470 [M⁺]

(47) 3-(Z)-{1-[4-(piperidin-1-yl-methyl)-anilino]-1-phenyl-methylidene}-6-methoxy-2-indolinone Prepared from 1-acetyl-3-(1-ethoxy-1-phenyl-methylidene)-6-methoxy-2-indolinone and 4-(piperidin-1-yl-methyl)-aniline $R_f$ value: 0.4 (aluminium oxide, toluene/ethyl acetate/methanol=4:2:0.25) $C_{28}H_{29}N_3O_2$ Mass spectrum: m/z=439 [M⁺]

(48) 3-(Z)-(1-{4-[(N-benzyl-N-methyl-amino)-methyl]-anilino}1-phenyl-methylidene)-6-methoxy-2-indolinone Prepared from 1-acetyl-3-(1-ethoxy-1-phenyl-methylidene)-6-methoxy-2-indolinone and 4-[(N-benzyl-N-methyl-amino)-methyl]-aniline $R_f$ value: 0.5 (aluminium oxide, toluene/ethyl acetate/ethanol=4:2:0.25) $C_{31}H_{29}N_3O_2$ Mass spectrum: m/z=475 [M⁺]

(49) 3-(Z)-{1-[3-(dimethylaminomethyl)-anilino]-1-phenyl-methylidene}-6-methoxy-2-indolinone Prepared from 1-acetyl-3-(1-ethoxy-1-phenyl-methylidene)-6-methoxy-2-indolinone and 3-(dimethylaminomethyl)-aniline $R_f$ value: 0.5 (silica gel, methylene chloride/methanol= 5:1) $C_{25}H_{25}N_3O_2$ Mass spectrum: m/z=399 [M⁺]

(50) 3-(Z)-{1-[4-(N-dimethylaminomethylcarbonyl-N-methylamino)-anilino]-1-ethyl-methylidene}-5,6-dimethoxy-2-indolinone Prepared from 1-acetyl-3-(1-ethoxy-1-ethyl-methylidene)-5,6-dimethoxy-2-indolinone and N-(dimethylaminomethylcarbonyl)-N-methyl-p-phenylenediamine $R_f$ value; 0.5 (silica gel, methylene chloride/methanol= 5:1) $C_{24}H_{30}N_4O_4$ Mass spectrum: m/z=438 [M⁺]

(51) 3-(Z)-{1-[4-(piperidin-1-yl-methyl)-anilino]-1-phenyl-methylidene}-5,6-diethoxy-2-indolinone Prepared from 1-acetyl-3-(1-ethoxy-1-phenyl-methylidene)-5,6-diethoxy-2-indolinone and 4-(piperidin-1-yl-methyl)-aniline $R_f$ value: 0.4 (aluminium oxide, toluene/ethyl acetate= 2:1) $C_{31}H_{35}N_3O_3$ ESI mass spectrum: m/z=498 [M+H⁺]

(52) 3-(Z)-{1-[4-(piperidin-1-yl-methyl)-anilino]-1-phenyl-methylidene}-6-trifluoromethyl-2-indolinone Prepared from 1-acetyl-3-(1-chloro-1-phenyl-methylidene)-6-trifluoromethyl-2-indolinone and 4-(piperidin-1-yl-methyl)-aniline $R_f$ value: 0.5 (silica gel, methylene chloride/methanol= 10:1) $C_{28}H_{26}F_3N_3O$ ESI mass spectrum: m/z=476 [M−H⁻]

(53) 3-(Z)-(1-{4-[N-(2-dimethylamino-ethyl)-N-methylsulphonyl-amino]-anilino}-1-phenyl-methylidene)-6-trifluoromethyl-2-indolinone Prepared from 1-acetyl-3-(1-chloro-1-phenyl-methylidene)-6-trifluoromethyl-2-indolinone and N-(2-dimethylamino-ethyl)-N-methylsulphonyl-p-phenylenediamine $R_f$ value: 0.5 (silica gel, methylene chloride/methanol= 10:1) $C_{27}H_{27}F_3N_4O_3S$ ESI mass spectrum: m/z=543 [M−H⁻]

(54) 3-(Z)-{1-[4-(N-dimethylaminomethylcarbonyl-N-methyl-amino)-anilino]-1-phenyl-methylidene}-6-trifluoromethyl-2-indolinone Prepared from 1-acetyl-3-(1-chloro-1-phenyl-methylidene)-6-trifluoromethyl-2-indolinone and N-(dimethylaminomethylcarbonyl)-N-methyl-p-phenylenediamine $R_f$ value: 0.4 (silica gel, methylene chloride/methanol= 10:1) $C_{27}H_{25}F_3N_4O_2$ ESI mass spectrum: m/z=493 [M−H⁻]

(55) 3-(Z)-{1-[4-(piperidin-1-yl-methyl)-anilino)-1-phenyl-methylidene}-6-phenyl-2-indolinone Prepared from 1-acetyl-3-(1-ethoxy-1-phenyl-methylidene)-6-phenyl-2-indolinone and 4-(piperidin-1-yl-methyl)-aniline $R_f$ value: 0.45 (silica gel, methylene chloride/methanol= 9:1) $C_{33}H_{31}N_3O$ ESI mass spectrum: m/z=486 [M+H⁺]

(56) 3-(Z)-(1-{4-[(N-benzyl-N-methyl-amino)-methyl]-anilino}-1-phenyl-methylidene)-6-phenyl-2-indolinone Prepared from 1-acetyl-3-(1-ethoxy-1-phenyl-methylidene)-6-phenyl-2-indolinone and 4-[(N-benzyl-N-methyl-amino)-methyl]-aniline $R_f$ value: 0.45 (silica gel, methylene chloride/methanol= 9:1) $C_{33}H_{31}N_3O$ ESI mass spectrum: m/z=486 [M+H⁺]

(57) 3-(Z)-(1-{4-[N-(2-dimethylamino-ethyl)-N-methylsulphonyl-amino]-anilino}-1-phenyl-methylidene)-6-phenyl-2-indolinone Prepared from 1-acetyl-3-(1-ethoxy-1-phenyl-methylidene)-6-phenyl-2-indolinone and N-(2-dimethylamino-ethyl)-N-methylsulphonyl-p-phenylenediamine $R_f$ value: 0.4 (silica gel, methylene chloride/methanol= 9:1) $C_{32}H_{32}N_4O_3S$ ESI mass spectrum: m/z=553 [M+H$^+$]

(58) 3-(Z)-{1-[3-(dimethylaminomethyl)-anilino]-1-phenyl-methylidene}-6-phenyl-2-indolinone Prepared from 1-acetyl-3-(1-ethoxy-1-phenyl-methylidene)-6-phenyl-2-indolinone and 3-(dimethylaminomethyl)-aniline $R_f$ value: 0.55 (silica gel, methylene chloride/methanol= 10:1) $C_{30}H_{27}N_3O$ ESI mass spectrum: m/z=446 [M+H$^+$]

(59) 3-(Z)-{1-[4-(N-dimethylaminomethylcarbonyl-N-methyl-amino)-anilino]-1-phenyl-methylidene}-6-phenyl-2-indolinone Prepared from 1-acetyl-3-(1-ethoxy-1-phenyl-methylidene)-6-phenyl-2-indolinone and N-(dimethylaminomethylcarbonyl)-N-methyl-p-phenylenediamine $R_f$ value: 0.45 (silica gel, methylene chloride/methanol= 9:1) $C_{32}H_{30}N_4O_2$ Mass spectrum: m/z=502 [M$^+$]

(60) 3-(Z)-{1-[4-(piperidin-1-yl-methyl)-anilino]-1-phenyl-methylidene}-6-(2-tolyl)-2-indolinone Prepared from 1-acetyl-3-(1-ethoxy-1-phenyl-methylidene)-6-(2-tolyl)-2-indolinone and 4-(piperidin-1-yl-methyl)-aniline $R_f$ value: 0.5 (silica gel, methylene chloride/methanol= 9:1) $C_{34}H_{33}N_3O$ ESI mass spectrum: m/z=500 [M+H$^+$]

(61) 3-(Z)-{1-[4-(dimethylaminomethyl)-anilino]-1-phenyl-methylidene}-6-(2-tolyl)-2-indolinone Prepared from 1-acetyl-3-(1-ethoxy-1-phenyl-methylidene)-6-(2-tolyl)-2-indolinone and 4-(dimethylaminomethyl)-aniline $R_f$ value: 0.45 (silica gel, methylene chloride/methanol= 9:1) $C_{31}H_{29}N_3O$ Mass spectrum: m/z=459 [M$^+$]

(62) 3-(Z)-[1-(4-ethoxycarbonyl-anilino)-1-phenyl-methylidene]-6-(2-tolyl)-2-indolinone Prepared from 1-acetyl-3-(1-ethoxy-1-phenyl-methylidene)-6-(2-tolyl)-2-indolinone and ethyl 4-aminobenzoate $R_f$ value: 0.5 (silica gel, toluene/ethyl acetate/ethanol= 4:2:1) $C_{31}H_{26}N_2O_3$ Mass spectrum: m/z=474 [M$^+$]

EXAMPLE 2

3-(Z)-(1-{4-[2-(4-carboxy-piperidin-1-yl)-ethyl]-anilino}-1-phenyl-methylidene)-5,6-dimethoxy-2-indolinone 0.4 g of 3-(Z)-(1-{4-[2-(4-ethoxycarbonyl-piperidin-1-yl)-ethyl]-anilino}-1-phenyl-methylidene)-5,6-dimethoxy-2-indolinone are dissolved in 8.0 ml of ethanol and 2.0 ml of 1N sodium hydroxide solution are added. The mixture is stirred for 1 hour at 50° C. 2.0 ml of 1N HCl are added to the clear solution and the precipitate formed is suction filtered. The precipitate is washed with water and ethanol and dried in vacuo at 100° C.

Yield: 0.2 g (64% of theory), $R_f$ value: 0.2 (silica gel, methylene chloride/methanol= 2:1) $C_{31}H_{33}N_3O_5$ ESI mass spectrum: m/z=526 [M−H$^-$]

The following compounds are prepared analogously to Example 2:

(1) 3-(Z)-[1-(4-carboxy-anilino)-1-phenyl-methylidene]-5,6-dimethoxy-2-indolinone Prepared from 3-(Z)-[1-(4-ethoxycarbonyl-anilino)-1-phenyl-methylidene]-5,6-dimethoxy-2-indolinone $R_f$ value: 0.4 (silica gel, methylene chloride/methanol= 10:1) $C_{24}H_{20}N_2O_5$ ESI mass spectrum: m/z=415 [M−H$^-$]

(2) 3-(Z)-{1-[4-(carboxymethyl)-anilino]-1-phenyl-methylidene}-5,6-dimethoxy-2-indolinone Prepared from 3-(Z)-{1-[4-(ethoxycarbonylmethyl)-anilino]-1-phenyl-methylidene}-5,6-dimethoxy-2-indolinone $R_f$ value: 0.1 (silica gel, petroleum ether/ethyl acetate/ethanol=7:2:1) $C_{25}H_{22}N_2O_5$ ESI mass spectrum: m/z=429 [M−H$^-$]

(3) 3-(Z)-[1-(4-carboxy-anilino)-1-ethyl-methylidene]-5,6-dimethoxy-2-indolinone Prepared from 3-(Z)-[1-(4-ethoxycarbonyl-anilino)-1-ethyl-methylidene]-5,6-dimethoxy-2-indolinone $R_f$ value: 0.4 (silica gel, methylene chloride/methanol= 9:1) $C_{20}H_{20}N_2O_5$ ESI mass spectrum: m/z=367 [M−H$^-$]

(4) 3-(Z)-{1-[4-(carboxymethyl)-anilino]-1-ethyl-methylidene}-5,6-dimethoxy-2-indolinone Prepared from 3-(Z)-{1-[4-(ethoxycarbonylmethyl)-anilino]-1-ethyl-methylidene}-5,6-dimethoxy-2-indolinone $R_f$ value; 0.4 (silica gel, toluene/ethyl acetate/ethanol= 4:2:1) $C_{21}H_{22}N_2O_5$ ESI mass spectrum: m/z=381 [M−H$^-$]

(5) 3-(Z)-[1-(4-carboxy-anilino)-1-phenyl-methylidene]-6-ureido-2-indolinone

Prepared from 3-(Z)-[1-(4-methoxycarbonyl-anilino)-1-phenyl-methylidene]-6-ureido-2-indolinone $R_f$ value: 0.45 (silica gel, methylene chloride/methanol= 4:1) $C_{23}H_{18}N_4O_4$ ESI mass spectrum: m/z=413 [M−H$^-$]

EXAMPLE 3

3-(Z)-(1-{4-[2-(4-dimethylcarbamoyl-piperidin-1-yl)-ethyl]-anilino}-1-phenyl-methylidene)-5,6-dimethoxy-2-indolinone 0.2 g of 3-(Z)-(1-{4-[2-(4-carboxy-piperidin-1-yl)-ethyl]-anilino}-1-phenyl-methylidene)-5,6-dimethoxy-2-indolinone are dissolved in 5.0 ml of dimethylformamide and 0.2 g of TBTU, 0.1 g of HOBT and 0.5 ml of triethylamine are added. Finally 0.2 g of dimethylamine hydrochloride are added and the mixture is stirred for 2 hours at ambient temperature. The solvent is eliminated and the residue is stirred with water, suction filtered and washed with isopropanol and ether. The residue is dried in vacuo at 100° C.

Yield: 0.2 g (95% of theory), $R_f$ value: 0.5 (silica gel, methylene chloride/methanol= 10:1) $C_{33}H_{38}N_4O_4$ Mass spectrum: m/z=554 [M$^+$]

The following compounds are prepared analogously to Example 3:

(1) 3-(Z)-{1-[4-(aminocarbonylmethyl)-anilino]-1-phenyl-methylidene}-5,6-dimethoxy-2-indolinone Prepared from 3-(Z)-(1-[4-(carboxymethyl)-anilino]-1-phenyl-methylidene)-5,6-dimethoxy-2-indolinone and N-hydroxy-succinimide-ammonium salt $R_f$ value: 0.4 (silica gel, petroleum ether/ethyl acetate/ethanol=4:2:1) $C_{25}H_{23}N_3O_4$ ESI mass spectrum: m/z=428 [M−H$^-$]

(2) 3-(Z)-{1-[4-(dimethylaminocarbonylmethyl)-anilino]-1-phenyl-methylidene}-5,6-dimethoxy-2-indolinone Prepared from 3-(Z)-{1-[4-(carboxymethyl)-anilino]-1-phenyl-methylidene}-5,6-dimethoxy-2-indolinone and dimethylamine-hydrochloride $R_f$ value: 0.45 (silica gel, petroleum ether/ethyl acetate/ethanol=4:2:1) $C_{27}H_{27}N_3O_4$ ESI mass spectrum: m/z=456 [M−H⁻]

(3) 3-(Z)-{1-[4-(aminocarbonylmethyl)-anilino]-1-ethyl-methylidene}-5,6-dimethoxy-2-indolinone Prepared from 3-(Z)-{1-[4-(carboxymethyl)-anilino]-1-ethyl-methylidene}-5,6-dimethoxy-2-indolinone and N-hydroxy-succinimide-ammonium salt $R_f$ value: 0.45 (silica gel, toluene/ethyl acetate/ethanol=4:2:1) $C_{21}H_{23}N_3O_4$ ESI mass spectrum: m/z=380 [M−H⁻]

(4) 3-(Z)-{1-[4-(dimethylaminocarbonylmethyl)-anilino]-1-ethyl-methylidene}-5,6-dimethoxy-2-indolinone Prepared from 3-(Z)-{1-[4-(carboxymethyl)-anilino]-1-ethyl-methylidene}-5,6-dimethoxy-2-indolinone and dimethylamine-hydrochloride $R_f$ value: 0.7 (silica gel, toluene/ethyl acetate/ethanol=4:2:1) $C_{23}H_{27}N_3O_4$ ESI mass spectrum: m/z=408 [M−H⁻]

EXAMPLE 4

6-amino-3-(Z)-{1-[4-(piperidin-1-yl-methyl)-anilino]-1-phenyl-methylidene}-2-indolinone 11.2 g of 3-(Z)-{1-[4-(piperidin-1-yl-methyl)-anilino]-1-phenyl-methylidene}-6-nitro-2-indolinone are dissolved in 120 ml of methanol and 60 ml of methylene chloride, 1.1 g of palladium on carbon (10%) are added and the mixture is hydrogenated for 2 hours 45 minutes at ambient temperature with 3 bar hydrogen. The catalyst is filtered off, the filtrate is concentrated by evaporation and the residue is purified through a silica gel column with methylene chloride/methanol (4:1).

Yield: 5.2 g (52% of theory), $R_f$ value: 0.25 (silica gel, methylene chloride/methanol=4:1) $C_{27}H_{28}N_4O$ ESI mass spectrum: m/z=425 [M+H⁺]

The following compound is prepared analogously to Example 4:

(1) 6-amino-3-(Z)-[1-(4-methoxycarbonyl-anilino)-1-phenyl-methylidene]-2-indolinone Prepared from 1-acetoxy-3-(Z)-[1-(4-methoxycarbonyl-anilino)-1-phenyl-methylidene]-6-nitro-2-indolinone $R_f$ value: 0.74 (silica gel, methylene chloride/methanol=4:1) $C_{23}H_{19}N_3O_3$ ESI mass spectrum: m/z=384 [M−H⁻]

EXAMPLE 5

3-(Z)-[1-(4-methoxycarbonyl-anilino)-1-phenyl-methylidene]-6-ureido-2-indolinone 560 mg of 6-amino-3-(Z)-[1-(4-methoxycarbonyl-anilino)-1-phenyl-methylidene]-2-indolinone, 236 mg of potassium cyanate and 3.8 ml of glacial acetic acid are dissolved in 20 ml of ethanol and refluxed for 1 hour. After this time the solvent is evaporated, the residue is taken up in methylene chloride, washed with water and dried over sodium sulphate. After evaporation, the product is dried in the desiccator.

Yield: 280 mg of (45% of theory), $R_f$ value: 0.25 (silica gel, ethyl acetate/cyclohexane/methanol=4.5:4.5:1) $C_{24}H_{20}N_4O_4$ ESI mass spectrum: m/z=427 [M−H⁻]

EXAMPLE 6

3-(Z)-[1-anilino-1-(3-aminomethyl-phenyl)-methylidene]-5,6-dimethoxy-2-indolinone 0.8 g of 3-(Z)-[1-anilino-1-(3-cyanophenyl)-methylidene]-5,6-dimethoxy-2-indolinone are dissolved in 50 ml of methanolic ammonia and 30 ml of methylene chloride are added. After the addition of 500 mg of Raney nickel the mixture is hydrogenated for 2 hours at ambient temperature at a pressure of 50 psi. After the end of the reaction the catalyst is filtered off and the filtrate is concentrated by evaporation. The residue is separated over a silica gel column with methylene chloride/methanol (5:1) as eluant. The product is suspended in 3 ml of dioxane, 0.4 ml of 1N hydrochloric acid are added and the solution formed is concentrated by evaporation after 10 minutes' stirring at ambient temperature. The residue thus obtained is triturated with ether, suction filtered and dried in vacuo at 80° C.

Yield: 0.1 g (14% of theory), $R_f$ value: 0.7 (silica gel, methylene chloride/methanol/ammonia=5:1:0.01) $C_{24}H_{23}N_3O_3$ ESI mass spectrum: m/z=402 [M+H⁺]

EXAMPLE 7

6-benzoylamino-3-(Z)-{1-[4-(piperidin-1-yl-methyl)-anilino]-1-phenyl-methylidene}-2-indolinone 0.4 g of 6-amino-3-(Z)-{1-[4-(piperidin-1-yl-methyl)-anilino]-1-phenyl-methylidene}-2-indolinone are dissolved in 25 ml of methylene chloride, 12.5 ml of pyridine are added and at ambient temperature 0.1 ml of benzoylchloride are added dropwise. The reaction mixture is stirred for 12 hours at ambient temperature, concentrated by evaporation and purified through a silica gel column with methylene chloride/methanol=4:1 as eluant.

Yield: 160 mg of (32% of theory), $R_f$ value: 0.3 (silica gel, methylene chloride/methanol=9:1) $C_{34}H_{32}N_4O_2$ ESI mass spectrum: m/z=529 [M+H⁺]

The following compounds are prepared analogously to Example 7:

(1) 6-acetylamino-3-(Z)-{1-[4-(piperidin-1-yl-methyl)-anilino]-1-phenyl-methylidene}-2-indolinone Prepared from 6-amino-3-(Z)-{1-[4-(piperidin-1-yl-methyl)-anilino]-1-phenyl-methylidene}-2-indolinone and acetylchloride $R_f$ value: 0.48 (silica gel, methylene chloride/methanol=4:1) $C_{29}H_{30}N_4O_2$ ESI mass spectrum: m/z=467 [M+H⁺]

(2) 6-(2-phenylacetylamino)-3-(Z)-{1-[4-(piperidin-1-yl-methyl)-anilino]-1-phenyl-methylidene}-2-indolinone Prepared from 6-amino-3-(Z)-{1-[4-(piperidin-1-yl-methyl)-anilino]-1-phenyl-methylidene}-2-indolinone and phenylacetic acid chloride $R_f$ value: 0.67 (silica gel, methylene chloride/methanol=4:1) $C_{35}H_{34}N_4O_2$ ESI mass spectrum: m/z=543 [M+H⁺]

(3) 6-methanesulphonylamino-3-(Z)-{1-[4-(piperidin-1-yl-methyl)-anilino]-1-phenyl-methylidene}-2-indolinone Prepared from 6-amino-3-(Z)-{1-[4-(piperidin-1-yl-methyl)-anilino]-1-phenyl-methylidene}-2-indolinone and methanesulphonylchloride $R_f$ value: 0.56 (silica gel, methylene chloride/methanol=4:1) $C_{28}H_{30}N_4O_3S$ ESI mass spectrum: m/z=503 [M+H⁺]

(4) 6-benzenesulphonylamino-3-(Z)-{1-[4-(piperidin-1-yl-methyl)-anilino]-1-phenyl-methylidene}-2-indolinone Prepared from 6-amino-3-(Z)-{1-[4-(piperidin-1-yl-methyl)-anilino]-1-phenyl-methylidene}-2-indolinone and benzenesulphonyl chloride $R_f$ value: 0.53 (silica gel, methylene chloride/methanol= 4:1) $C_{33}H_{32}N_4O_3S$ ESI mass spectrum: m/z=565 [M+H$^+$]

(5) 3-(Z)-{1-anilino-1-[3-(acetylaminomethyl)-phenyl]-methylidene}-5,6-dimethoxy-2-indolinone Prepared from 3-(Z)-[1-anilino-1-(3-aminomethyl-phenyl)-methylidene]-5,6-dimethoxy-2-indolinone and acetic anhydride $R_f$ value: 0.5 (silica gel, methylene chloride/methanol= 10:1) $C_{26}H_{25}N_3O_4$ ESI mass spectrum: m/z=442 [M−H$^-$]

EXAMPLE 8

6-methylamino-3-(Z)-{1-[4-(piperidin-1-yl-methyl)-anilino]-1-phenyl-methylidene}-2-indolinone and 6-dimethylamino-3-(Z)-{1-[4-(piperidin-1-yl-methyl)-anilino]-1-phenyl-methylidene}-2-indolinone 0.1 ml of formaldehyde solution (37%) are dissolved in 20 ml of methanol, 0.5 g of 6-amino-3-(Z)-{1-[4-(piperidin-1-yl-methyl)-anilino]-1-phenyl-methylidene}-2-indolinone are added and the mixture is stirred for 1 hour at ambient temperature. A precipitate is formed which is brought into solution by the addition of 5 ml of methylene chloride. To this mixture are added 75 mg of sodium cyanoborohydride and the mixture is stirred for 12 hours at ambient temperature. After this time 5 ml of conc. HCl are added, the solvent is substantially eliminated, the residue taken up in water and made basic with sodium hydroxide solution. The aqueous phase is extracted with methylene chloride, dried over sodium sulphate, concentrated by evaporation and purified through a silica gel column with methylene chloride/methanol (4:1).

Yield: 70 mg of (13% of theory) 6-methylamino-3-(Z)-{1-[4 (piperidin-1-yl-methyl)-anilino]-1-phenyl-methylidene}-2-indolinone, $R_f$ value: 0.64 (silica gel, methylene chloride/methanol= 4:1) $C_{28}H_{30}N_4O$ Mass spectrum: m/z=438 [M$^{+]}$ 35 mg of (6% of theory) 6-dimethylamino-3-(Z)-{1-[4-(piperidin-1-yl-methyl)-anilino]-1-phenyl-methylidene}-2-indolinone, $R_f$ value: 0.58 (silica gel, methylene chloride/methanol= 4:1) $C_{29}H_{34}N_4O$ ESI mass spectrum: m/z=453 [M+H$^+$]

EXAMPLE 9

3-(Z)-{1-[4-(piperidin-1-yl-methyl)-anilino]-1-phenyl-methylidene}-6-(pyrrol-1-yl)-2-indolinone 0.5 g of 6-amino-3-(Z)-{1-[4-(piperidin-1-yl-methyl)-anilino]-1-phenyl-methylidene}-2-indolinone are dissolved in 20 ml of glacial acetic acid and 0.2 ml of 2,5-dimethoxytetrahydrofuran are added. The mixture is refluxed for 1 hour, concentrated by evaporation and the residue is taken up in 20 ml of water. After another 2 hours' stirring the mixture is made basic with 1N sodium hydroxide solution, the aqueous phase is extracted with methylene chloride and the organic phase is dried over sodium sulphate. After elimination of the solvent the residue is purified through a silica gel column with methylene chloride/methanol (4:1) as eluant.

Yield: 200 mg of (36% of theory), $R_f$ value: 0.73 (silica gel, methylene chloride/methanol= 4:1) $C_{31}H_{30}N_4O$ ESI mass spectrum: m/z=475 [M+H$^+$]

EXAMPLE 10

3-(Z)-{1-[4-(piperidin-1-yl-methyl)-anilino]-1-phenyl-methylidene}-6-(pyrrolidin-1-yl)-2-indolinone 0.3 g of 6-amino-3-(Z)-{1-[4-(piperidin-1-yl-methyl)-anilino]-1-phenyl-methylidene}-2-indolinone are dissolved in 10 ml of dimethylformamide and 180 mg of potassium carbonate are added. 0.1 ml of 1,4-dibromobutane (dissolved in 1.0 ml of dimethylformamide) is added dropwise at ambient temperature and the reaction mixture is stirred for 12 hours at 80° C. After cooling the mixture is poured onto water and the precipitate formed is filtered off.

Yield: 110 mg of (33% of theory), $R_f$ value: 0.41 (silica gel, methylene chloride/methanol= 9:1) $C_{31}H_{34}N_4O$ ESI mass spectrum: m/z=479 [M+H$^+$]

The following compound is prepared analogously to Example 10:

(1) 6-methoxycarbonylmethylamino-3-(Z)-{1-[4-(piperidin-1-yl-methyl)-anilino]-1-phenyl-methylidene}-2-indolinone Prepared from 6-amino-3-(Z)-{1-[4-(piperidin-1-yl-methyl)-anilino]-1-phenyl-methylidene}-2-indolinone and methyl bromoacetate Yield: 230 mg of (28% of theory), $R_f$ value: 0.36 (silica gel, methylene chloride/methanol= 9:1) $C_{30}H_{32}N_4O_3$ ESI mass spectrum: m/z=497 [M+H$^+$]

EXAMPLE 11

6-carboxymethylamino-3-(Z)-{1-[4-(piperidin-1-yl-methyl)-anilino]-1-phenyl-methylidene}-2-indolinone 180 mg of 6-methoxycarbonylmethylamino-3-(Z)-{1-[4-(piperidin-1-yl-methyl)-anilino]-1-phenyl-methylidene}-2-indolinone are placed in 10 ml of methanol, 1.0 ml of 1N sodium hydroxide solution are added and the mixture is stirred for 1 hour at 40° C. After cooling it is neutralised with 1.0 ml of 1N hydrochloric acid and the solvent is eliminated. The residue is dissolved in methylene chloride and a little methanol and dried over sodium sulphate.

Yield: 76 mg of (44% of theory), $R_f$ value: 0.05 (silica gel, methylene chloride/methanol= 9:1) $C_{29}H_{30}N_4O_3$ ESI mass spectrum: m/z=483 [M+H$^+$]

The following compounds may be prepared analogously to the preceding Examples:

(1) 3-(Z)-(1-anilino-1-phenyl-methylidene)-5,6-dimethoxy-2-indolinone (2) 3-(Z)-[1-(4-nitro-anilino)-1-phenyl-methylidene]-5,6-dimethoxy-2-indolinone (3) 3-(Z)-1-[(4-fluoro-anilino)-1-phenyl-methylidene]-5,6-dimethoxy-2-indolinone (4) 3-(Z)-[1-(4-bromo-anilino)-1-phenyl-methylidene]-5,6-dimethoxy-2-indolinone (5) 3-(Z)-[1-(4-iodo-anilino)-1-phenyl-methylidene]-5,6-dimethoxy-2-indolinone
(6) 3-(Z)-[1-(4-cyano-anilino)-1-phenyl-methylidene]-5,6-dimethoxy-2-indolinone
(7) 3-(Z)-[1-(4-ethoxy-anilino)-1-phenyl-methylidene]-5,6-dimethoxy-2-indolinone
(8) 3-(Z)-[1-(4-trifluoromethyl-anilino)-1-phenyl-methylidene]-5,6-dimethoxy-2-indolinone
(9) 3-(Z)-[1-(4-methyl-anilino)-1-phenyl-methylidene]-5,6-dimethoxy-2-indolinone
(10) 3-(Z)-[1-(4-methylmercapto-anilino)-1-phenyl-methylidene]-5,6-dimethoxy-2-indolinone
(11) 3-(Z)-[1-(4-aminomethyl-anilino)-1-phenyl-methylidene]-5,6-dimethoxy-2-indolinone
(12) 3-(Z)-{1-[4-(methylaminomethyl)-anilino]-1-phenyl-methylidene}-5,6-dimethoxy-2-indolinone
(13) 3-(Z)-{1-[4-(isopropylaminomethyl)-anilino]-1-phenyl-methylidene}-5,6-dimethoxy-2-indolinone
(14) 3-(Z)-{1-[4-(phenylaminomethyl)-anilino]-1-phenyl-methylidene}-5,6-dimethoxy-2-indolinone
(15) 3-(Z)-{1-[4-(ethylaminomethyl)-anilino]-1-phenyl-methylidene}-5,6-dimethoxy-2-indolinone
(16) 3-(Z)-{1-[4-(propylaminomethyl)-anilino]-1-phenyl-methylidene}-5,6-dimethoxy-2-indolinone
(17) 3-(Z)-{1-[4-(butylaminomethyl)-anilino]-1-phenyl-methylidene}-5,6-dimethoxy-2-indolinone
(18) 3-(Z)-{1-[4-(isobutylaminomethyl)-anilino]-1-phenyl-methylidene}-5,6-dimethoxy-2-indolinone
(19) 3-(Z)-{1-[4-(cyclohexylaminomethyl)-anilino]-1-phenyl-methylidene}-5,6-dimethoxy-2-indolinone
(20) 3-(Z)-{1-[4-(benzylaminomethyl)-anilino]-1-phenyl-methylidene}-5,6-dimethoxy-2-indolinone
(21) 3-(Z)-1-{4-[(N-ethyl-N-methyl-amino)-methyl]-anilino}-1-phenyl-methylidene)-5,6-dimethoxy-2-indolinone
(22) 3-(Z)-{1-[4-(diethylaminomethyl)-anilino]-1-phenyl-methylidene}-5,6-dimethoxy-2-indolinone
(23) 3-(Z)-(1-{4-[(N-methyl-N-propyl-amino)-methyl]-anilino}-1-phenyl-methylidene)-5,6-dimethoxy-2-indolinone
(24) 3-(Z)-(1-{4-[(N-isopropyl-N-methyl-amino)-methyl]-anilino}-1-phenyl-methylidene)-5,6-dimethoxy-2-indolinone
(25) 3-(Z)-(1-{4-[(N-ethyl-N-propyl-amino)-methyl]-anilino}-1-phenyl-methylidene)-5,6-dimethoxy-2-indolinone
(26) 3-(Z)-(1-{4-[(N-ethyl-N-isopropyl-amino)-methyl]-anilino}-1-phenyl-methylidene)-5,6-dimethoxy-2-indolinone
(27) 3-(Z)-{1-[4-(dipropylaminomethyl)-anilino]-1-phenyl methylidene}-5,6-dimethoxy-2-indolinone
(28) 3-(Z)-{1-[4-(diisopropylaminomethyl)-anilino]-1-phenyl-methylidene}-5,6-dimethoxy-2-indolinone
(29) 3-(Z)-(1-{4-[(N-benzyl-N-ethyl-amino)-methyl]-anilino}-1-phenyl-methylidene)-5,6-dimethoxy-2-indolinone
(30) 3-(Z)-{1-[4-(dibenzylaminomethyl)-anilino]-1-phenyl-methylidene}-5,6-dimethoxy-2-indolinone
(31) 3-(Z)-{1-[4-(3,6-dihydro-2H-pyridine-1-yl-methyl)-anilino]-1-phenyl-methylidene}-5,6-dimethoxy-2-indolinone
32) 3-(Z)-{1-[4-(3,5-dimethyl-piperidin-1-yl-methyl)-anilino]-1-phenyl-methylidene}-5,6-dimethoxy-2-indolinone
(33) 3-(Z)-{1-[4-(azepan-1-yl-methyl)-anilino]-1-phenyl-methylidene}-5,6-dimethoxy-2-indolinone
(34) 3-(Z)-{1-[4-(piperazin-1-yl-methyl)-anilino]-1-phenyl-methylidene}-5,6-dimethoxy-2-indolinone
(35) 3-(Z)-{1-[4-(morpholin-4-yl-methyl)-anilino]-1-phenyl-methylidene}-5,6-dimethoxy-2-indolinone
(36) 3-(Z)-{1-[4-(thiomorpholin-4-yl-methyl)-anilino]-1-phenyl-methylidene}-5,6-dimethoxy-2-indolinone
(37) 3-(Z)-{1-[4-(1-oxo-thiomorpholin-4-yl-methyl)-anilino]-1-phenyl-methylidene}-5,6-dimethoxy-2-indolinone
(38) 3-(Z)-{1-[4-(acetylamino-methyl)-anilino]-1-phenyl-methylidene}-5,6-dimethoxy-2-indolinone
(39) 3-(Z)-{1-[4-(2-amino-ethyl)-anilino]-1-phenyl-methylidene}-5,6-dimethoxy-2-indolinone
(40) 3-(Z)-{1-[4-(2-methylamino-ethyl)-anilino]-1-phenyl-methylidene}-5,6-dimethoxy-2-indolinone
(41) 3-(Z)-{1-[4-(2-ethylamino-ethyl)-anilino]-1-phenyl-methylidene}-5,6-dimethoxy-2-indolinone
(42) 3-(Z)-{1-[4-(2-diethylamino-ethyl)-anilino]-1-phenyl-methylidene}-5,6-dimethoxy-2-indolinone
(43) 3-(Z)-{1-[4-(2-piperidin-1-yl-ethyl)-anilino]-1-phenyl-methylidene}-5,6-dimethoxy-2-indolinone
(44) 3-(Z)-{1-[4-(2-acetylamino-ethyl)-anilino]-1-phenyl-methylidene}-5,6-dimethoxy-2-indolinone
(45) 3-(Z)-{1-[4-(3-amino-propyl)-anilino]-1-phenyl-methylidene}-5,6-dimethoxy-2-indolinone
(46) 3-(Z)-{1-[4-(3-dimethylamino-propyl)-anilino]-1-phenyl-methylidene}-5,6-dimethoxy-2-indolinone
(47) 3-(Z)-{1-[4-(N-aminomethylcarbonyl-N-methyl-amino)-anilino]-1-phenyl-methylidene}-5,6-dimethoxy-2-indolinone
(48) 3-(Z)-{1-[4-(N-methylaminomethylcarbonyl-N-methyl-amino)-anilino]-1-phenyl-methylidene}-5,6-dimethoxy-2-indolinone
(49) 3-(Z)-{1-[4-(N-ethylaminomethylcarbonyl-N-methyl-amino)-anilino]-1-phenyl-methylidene}-5,6-dimethoxy-2-indolinone
(50) 3-(Z)-{1-[4-(N-diethylaminomethylcarbonyl-N-methyl-amino)-anilino]-1-phenyl-methylidene}-5,6-dimethoxy-2-indolinone
(51) 3-(Z)-(1-{4-[N-(piperidin-1-yl-methylcarbonyl)-N-methylamino]-anilino}-1-phenyl-methylidene)-5,6-dimethoxy-2-indolinone
(52) 3-(Z)-(1-{4-[N-(morpholin-4-yl-methylcarbonyl)-N-methylamino]-anilino}-1-phenyl-methylidene)-5,6-dimethoxy-2-indolinone
(53) 3-(Z)-(1-{4-[N-(piperazin-1-yl-methylcarbonyl)-N-methylamino]-anilino}-1-phenyl-methylidene)-5,6-dimethoxy-2-indolinone
(54) 3-(Z)-(1-{4-[N-(2-amino-ethyl-carbonyl)-N-methyl-amino]-anilino}-1-phenyl-methylidene)-5,6-dimethoxy-2-indolinone
(55) 3-(Z)-(1-{4-[N-(2-methylamino-ethyl-carbonyl)-N-methylamino]-anilino}-1-phenyl-methylidene)-5,6-dimethoxy-2-indolinone
(56) 3-(Z)-(1-{4-[N-(2-diethylamino-ethyl-carbonyl)-N-methylamino]-anilino}-1-phenyl-methylidene)-5,6-dimethoxy-2-indolinone
(57) 3-(Z)-(1-{4-[N-acetyl-N-(2-aminoethyl)-amino]-anilino}-1-phenyl-methylidene)-5,6-dimethoxy-2-indolinone
(58) 3-(Z)-(1-{4-[N-acetyl-N-(2-methylamino-ethyl)-amino]-anilino}-1-phenyl-methylidene)-5,6-dimethoxy-2-indolinone
(59) 3-(Z)-(1-{4-[N-acetyl-N-(3-amino-propyl)-amino]-anilino}-1-phenyl-methylidene)-5,6-dimethoxy-2-indolinone
(60) 3-(Z)-(1-{4-[N-acetyl-N-(2-methylamino-propyl)-amino]-anilino}-1-phenyl-methylidene)-5,6-dimethoxy-2-indolinone

(61) 3-(Z)-(1-{4-[N-acetyl-N-(2-piperidin-1-yl-ethyl)-amino]-anilino}-1-phenyl-methylidene)-5,6-dimethoxy-2-indolinone

(62) 3-(Z)-(1-{4-[N-acetyl-N-(aminocarbonylmethyl)-amino]-anilino}-1-phenyl-methylidene)-5,6-dimethoxy-2-indolinone

(63) 3-(Z)-(1-{4-[N-acetyl-N-(dimethylaminocarbonylmethyl)-amino]-anilino}-1-phenyl-methylidene)-5,6-dimethoxy-2-indolinone

(64) 3-(Z)-(1-{4-[N-acetyl-N-(piperidin-1-yl-carbonylmethyl)-amino]-anilino}-1-phenyl-methylidene)-5,6-dimethoxy-2-indolinone

(65) 3-(Z)-(1-{4-[N-methyl-N-(aminocarbonyl)-amino]-anilino}-1-phenyl-methylidene)-5,6-dimethoxy-2-indolinone

(66) 3-(Z)-(1-{4-[N-methyl-N-(methylaminocarbonyl)-amino]-anilino}-1-phenyl-methylidene)-5,6-dimethoxy-2-indolinone

(67) 3-(Z)-(1-{4-[N-methyl-N-(dimethylaminocarbonyl)-amino]-anilino}-1-phenyl-methylidene)-5,6-dimethoxy-2-indolinone

(68) 3-(Z)-(1-{4-[N-methyl-N-(piperidin-1-yl-carbonyl)-amino]-anilino}-1-phenyl-methylidene)-5,6-dimethoxy-2-indolinone

(69) 3-(Z)-(1-{4-[N-(2-aminoethyl)-N-methylsulphonyl-amino]-anilino}-1-phenyl-methylidene)-5,6-dimethoxy-2-indolinone

(70) 3-(Z)-(1-{4-[N-(2-methylamino-ethyl)-N-methylsulphonyl-amino]-anilino}-1-phenyl-methylidene)-5,6-dimethoxy-2-indolinone

(71) 3-(Z)-(1-{4-[N-(2-ethylamino-ethyl)-N-methylsulphonyl-amino]-anilino}-1-phenyl-methylidene)-5,6-dimethoxy-2-indolinone

(72) 3-(Z)-(1-{4-[N-(2-diethylamino-ethyl)-N-methylsulphonyl-amino]-anilino}-1-phenyl-methylidene)-5,6-dimethoxy-2-indolinone

(73) 3-(Z)-(1-{4-[N-(2-pyrrolidin-1-yl-ethyl)-N-methylsulphonyl-amino]-anilino}-1-phenyl-methylidene)-5,6-dimethoxy-2-indolinone

(74) 3-(Z)-(1-{4-[N-(2-piperidin-1-yl-ethyl)-N-methylsulphonyl-amino]-anilino}-1-phenyl-methylidene)-5,6-dimethoxy-2-indolinone

(75) 3-(Z)-(1-{4-[N-(2-piperazin-1-yl-ethyl)-N-methylsulphonyl-amino]-anilino}-1-phenyl-methylidene)-5,6-dimethoxy-2-indolinone

(76) 3-(Z)-[1-(4-{N-[2-(morpholin-4-yl)-ethyl]-N-methylsulphonyl-amino}-anilino)-1-phenyl-methylidene]-5,6-dimethoxy-2-indolinone

(77) 3-(Z)-(1-{4-[N-(aminocarbonylmethyl)-N-methylsulphonyl-amino]-anilino}-1-phenyl-methylidene)-5,6-dimethoxy-2-indolinone

(78) 3-(Z)-(1-{4-[N-(methylaminocarbonylmethyl)-N-methylsulphonyl-amino]-anilino}-1-phenyl-methylidene)-5,6-dimethoxy-2-indolinone

(79) 3-(Z)-(1-{4-[N-(ethylaminocarbonylmethyl)-N-methylsulphonyl-amino]-anilino}-1-phenyl-methylidene)-5,6-dimethoxy-2-indolinone

(80) 3-(Z)-[1-(4-{N-[N-(2-dimethylamino-ethyl)-N-methyl-amino)-carbonylmethyl]-N-methylsulphonyl-amino}-anilino)-1-phenyl-methylidene]-5,6-dimethoxy-2-indolinone

(81) 3-(Z)-(1-{4-[N-(diethylaminocarbonylmethyl)-N-methylsulphonyl-amino]-anilino}-1-phenyl-methylidene)-5,6-dimethoxy-2-indolinone

(82) 3-(Z)-(1-{4-[N-(pyrrolidin-1-yl-carbonylmethyl)-N-methyl-sulphonyl-amino]-anilino}-1-phenyl-methylidene)-5,6-dimethoxy-2-indolinone

(83) 3-(Z)-(1-{4-[N-(piperidin-1-yl-carbonylmethyl)-N-methyl-sulphonyl-amino]-anilino}-1-phenyl-methylidene)-5,6-dimethoxy-2-indolinone

(84) 3-(Z)-(1-{4-[N-(piperazin-1-yl-carbonylmethyl)-N-methyl-sulphonyl-amino]-anilino}-1-phenyl-methylidene)-5,6-dimethoxy-2-indolinone

(85) 3-(Z)-[1-(4-{N-[(morpholin-4-yl)-carbonylmethyl]-N-methylsulphonyl-amino}-anilino)-1-phenyl-methylidene]-5,6-dimethoxy-2-indolinone

(86) 3-(Z)-{1-[4-(2-dimethylamino-ethoxy)-anilino]-1-phenyl-methylidene}-5,6-dimethoxy-2-indolinone

(87) 3-(Z)-{1-[4-(3-dimethylamino-propoxy)-anilino]-1-phenyl-methylidene}-5,6-dimethoxy-2-indolinone

(88) 3-(Z)-{1-[4-(2-aminocarbonyl-ethyl)-anilino]-1-phenyl-methylidene}-5,6-dimethoxy-2-indolinone

(89) 3-(Z)-{1-[4-(pyridine-2-yl)-anilino]-1-phenyl-methylidene}-5,6-dimethoxy-2-indolinone

(90) 3-(Z)-{1-[4-(pyridine-3-yl)-anilino]-1-phenyl-methylidene}-5,6-dimethoxy-2-indolinone

(91) 3-(Z)-{1-[4-(pyridine-4-yl)-anilino]-1-phenyl-methylidene}-5,6-dimethoxy-2-indolinone

(92) 3-(Z)-[1-(4-nitro-anilino)-1-ethyl-methylidene]-5,6-dimethoxy-2-indolinone

(93) 3-(Z)-1-[(4-fluoro-anilino)-1-ethyl-methylidene]-5,6-dimethoxy-2-indolinone (0.94) 3-(Z)-1-[(4-chloro-anilino)-1-ethyl-methylidene]-5,6-dimethoxy-2-indolinone

(95) 3-(Z)-[1-(4-bromo-anilino)-1-ethyl-methylidene]-5,6-dimethoxy-2-indolinone

(96) 3-(Z)-[1-(4-iodo-anilino)-1-ethyl-methylidene]-5,6-dimethoxy-2-indolinone

(97) 3-(Z)-[1-(4-cyano-anilino)-1-ethyl-methylidene]-5,6-dimethoxy-2-indolinone

(98) 3-(Z)-[1-(4-methoxy-anilino)-1-ethyl-methylidene]-5,6-dimethoxy-2-indolinone

(99) 3-(Z)-[1-(4-ethoxy-anilino)-1-ethyl-methylidene]-5,6-dimethoxy-2-indolinone (100) 3-(Z)-[1-(4-trifluoromethyl-anilino)-1-ethyl-methylidene]-5,6-dimethoxy-2-indolinone (101) 3-(Z)-[1-(4-methyl-anilino)-1-ethyl-methylidene]-5,6-dimethoxy-2-indolinone (102) 3-(Z)-[1-(4-methylmercapto-anilino)-1-ethyl-methylidene]-5,6-dimethoxy-2-indolinone (103) 3-(Z)-[1-(4-aminomethyl-anilino)-1-ethyl-methylidene]-5,6-dimethoxy-2-indolinone (104) 3-(Z)-{1-[4-(methylaminomethyl)-anilino]-1-ethyl-methylidene}-5,6-dimethoxy-2-indolinone (105) 3-(Z)-{1-[4-(isopropylaminomethyl)-anilino]-1-ethyl-methylidene}-5,6-dimethoxy-2-indolinone (106) 3-(Z)-{1-[4-(phenylaminomethyl)-anilino]-1-ethyl-methylidene}-5,6-dimethoxy-2-indolinone (107) 3-(Z)-{1-[4-(ethylaminomethyl)-anilino]-1-ethyl-methylidene}-5,6-dimethoxy-2-indolinone (108) 3-(Z)-{1-[4-(propylaminomethyl)-anilino]-1-ethyl-methylidene}-5,6-dimethoxy-2-indolinone (109) 3-(Z)-{1-[4-(butylaminomethyl)-anilino]-1-ethyl-methylidene}-5,6-dimethoxy-2-indolinone (110) 3-(Z)-{1-[4-(isobutylaminomethyl)-anilino]-1-ethyl-methylidene}-5,6-dimethoxy-2-indolinone (111) 3-(Z)-{1-[4-(cyclohexylaminomethyl)-anilino]-1-ethyl-methylidene}-5,6-dimethoxy-2-indolinone (112) 3-(Z)-{1-[4-(benzylaminomethyl)-anilino]-1-ethyl-methylidene}-5,6-dimethoxy-2-indolinone (113) 3-(Z)-{1-[3-(dimethylamino-methyl)-anilino]-1-ethyl-methylidene}-5,6-dimethoxy-2-indolinone (114) 3-(Z)-(1-{4-[(N-ethyl-N-methyl-amino)-methyl]-anilino}-1-ethyl-methylidene)-5,6-dimethoxy-2-indolinone (115) 3-(Z)-{1-[4-(diethylaminomethyl)-anilino]-1-ethyl-methylidene}-5,6-dimethoxy-2-indolinone
(116) 3-(Z)-(1-{4-[(N-methyl-N-propyl-amino)-methyl)-anilino}-1-ethyl-methylidene)-5,6-dimethoxy-2-indolinone
(117) 3-(Z)-(1-{4-[(N-isopropyl-N-methyl-amino)-methyl]-anilino}-1-ethyl-methylidene)-5,6-dimethoxy-2-indolinone
(118) 3-(Z)-(1-{4-[(N-ethyl-N-propyl-amino)-methyl)-anilino}-1-ethyl-methylidene)-5,6-dimethoxy-2-indolinone
(119) 3-(Z)-(1-{4-[(N-ethyl-N-isopropyl-amino)-methyl]-anilino}-1-ethyl-methylidene)-5,6-dimethoxy-2-indolinone
(120) 3-(Z)-{1-[4-(dipropylaminomethyl)-anilino]-1-ethyl-methylidene}-5,6-dimethoxy-2-indolinone
(121) 3-(Z)-{1-[4-(diisopropylaminomethyl)-anilino]-1-ethyl-methylidene}-5,6-dimethoxy-2-indolinone
(122) 3-(Z)-(1-{4-[(N-benzyl-N-methyl-amino)-methyl]-anilino}-1-ethyl-methylidene)-5,6-dimethoxy-2-indolinone
(123) 3-(Z)-(1-{4-[(N-benzyl-N-ethyl-amino)-methyl]-anilino}1-ethyl-methylidene)-5,6-dimethoxy-2-indolinone
(124) 3-(Z)-{1-[4-(dibenzylaminomethyl)-anilino]-1-ethyl-methylidene}-5,6-dimethoxy-2-indolinone
(125) 3-(Z)-{1-[4-(pyrrolidin-1-yl-methyl)-anilino]-1-ethyl-methylidene}-5,6-dimethoxy-2-indolinone
(126) 3-(Z)-{1-[4-(3,6-dihydro-2H-pyridine-1-yl-methyl)-anilino]-1-ethyl-methylidene}-5,6-dimethoxy-2-indolinone
(127) 3-(Z)-{1-(4-(2,6-dimethyl-piperidin-1-yl-methyl)-anilino]-1-ethyl-methylidene}-5,6-dimethoxy-2-indolinone
(128) 3-(Z)-{1-[4-(3,5-dimethyl-piperidin-1-yl-methyl)-anilino]-1-ethyl-methylidene}-5,6-dimethoxy-2-indolinone
(129) 3-(Z)-{1-[4-(azepan-1-yl-methyl)-anilino]-1-ethyl-methylidene}-5,6-dimethoxy-2-indolinone
(130) 3-(Z)-{1-[4-(piperazin-1-yl-methyl)-anilino]-1-ethyl-methylidene}-5,6-dimethoxy-2-indolinone
(131) 3-(Z)-{1-[4-(morpholin-4-yl-methyl)-anilino]-1-ethyl-methylidene}-5,6-dimethoxy-2-indolinone
(132) 3-(Z)-{1-[4-(thiomorpholin-4-yl-methyl)-anilino]-1-ethyl-methylidene}-5,6-dimethoxy-2-indolinone
(133) 3-(Z)-{1-[4-(1-oxo-thiomorpholin-4-yl-methyl)-anilino]-1-ethyl-methylidene}-5,6-dimethoxy-2-indolinone
(134) 3-(Z)-{1-[4-(acetylamino-methyl)-anilino]-1-ethyl-methylidene}-5,6-dimethoxy-2-indolinone
(135) 3-(Z)-{1-[4-(2-amino-ethyl)-anilino]-1-ethyl-methylidene}-5,6-dimethoxy-2-indolinone
(136) 3-(Z)-1-{[4-(2-methylamino-ethyl)-anilino]-1-ethyl-methylidene}-5,6-dimethoxy-2-indolinone
(137) 3-(Z)-{1-[4-(2-ethylamino-ethyl)-anilino]-1-ethyl-methylidene}-5,6-dimethoxy-2-indolinone
(138) 3-(Z)-{1-[4-(2-dimethylamino-ethyl)-anilino]-1-ethyl-methylidene}-5,6-dimethoxy-2-indolinone
(139) 3-(Z)-{1-[4-(2-diethylamino-ethyl)-anilino]-1-ethyl-methylidene}-5,6-dimethoxy-2-indolinone
(140) 3-(Z)-{1-[4-(2-piperidin-1-yl-ethyl)-anilino]-1-ethyl-methylidene}-5,6-dimethoxy-2-indolinone
(141) 3-(Z)-(1-{4-[2-(4-ethoxycarbonyl-piperidin-1-yl)-ethyl]-anilino}-1-ethyl-methylidene)-5,6-dimethoxy-2-indolinone
(142) 3-(Z)-(1-{4-[2-(4-carboxy-piperidin-1-yl)-ethyl]-anilino}-1-ethyl-methylidene)-5,6-dimethoxy-2-indolinone
(143) 3-(Z) (1-{4-[2-(4-dimethylcarbamoyl-piperidin-1-yl)-ethyl]-anilino}-1-ethyl-methylidene)-5,6-dimethoxy-2-indolinone
(144) 3-(Z)-{1-[4(2-acetylamino-ethyl)-anilino]-1-ethyl-methylidene}-5,6-dimethoxy-2-indolinone
(145) 3-(Z)-{1-[4-(3-amino-propyl)-anilino]-1-ethyl-methylidene}-5,6-dimethoxy-2-indolinone
(146) 3-(Z)-{1-[4-(3-dimethylamino-propyl)-anilino]-1-ethyl-methylidene}-5,6-dimethoxy-2-indolinone
(147) 3-(Z)-{1-[4-(N-aminomethylcarbonyl-N-methyl-amino)-anilino]-1-ethyl-methylidene}-5,6-dimethoxy-2-indolinone
(148) 3-(Z)-{1-[4-(N-methylaminomethylcarbonyl-N-methyl-amino)-anilino]-1-ethyl-methylidene}-5,6-dimethoxy-2-indolinone
(149) 3-(Z)-{1-[4-(N-ethylaminomethylcarbonyl-N-methyl-amino)-anilino]-1-ethyl-methylidene}-5,6-dimethoxy-2-indolinone
(150) 3-(Z)-{1-[4-(N-diethylaminomethylcarbonyl-N-methyl-amino)-anilino]-1-ethyl-methylidene}-5,6-dimethoxy-2-indolinone
(151) 3-(Z)-(1-{4-[N-(piperidin-1-yl-methylcarbonyl)-N-methyl-amino]-anilino}-1-ethyl-methylidene)-5,6-dimethoxy-2-indolinone
(152) 3-(Z)-(1-{4-[N-(morpholin-4-yl-methylcarbonyl)-N-methyl-amino]-anilino}-1-ethyl-methylidene)-5,6-dimethoxy-2-indolinone
(153) 3-(Z)-(1-{4-[N-(piperazin-1-yl-methylcarbonyl)-N-methyl-amino]-anilino}-1-ethyl-methylidene)-5,6-dimethoxy-2-indolinone
(154) 3-(Z)-(1-{4-[N-(2-amino-ethyl-carbonyl)-N-methyl-amino]-anilino}-1-ethyl-methylidene)-5,6-dimethoxy-2-indolinone
(155) 3-(Z)-(1-{4-[N-(2-methylamino-ethyl-carbonyl)-N-methyl-amino]-anilino}-1-ethyl-methylidene)-5,6-dimethoxy-2-indolinone
(156) 3-(Z)-(1-{4-[N-(2-diethylamino-ethyl-carbonyl)-N-methyl-amino]-anilino}-1-ethyl-methylidene)-5,6-dimethoxy-2-indolinone
(157) 3-(Z)-(1-{4-[N-acetyl-N-(2-aminoethyl)-amino]-anilino}-1-ethyl-methylidene)-5,6-dimethoxy-2-indolinone
(158) 3-(Z)-(1-{4-[N-acetyl-N-(2-methylamino-ethyl)-amino]-anilino}-1-ethyl-methylidene)-5,6-dimethoxy-2-indolinone
(159) 3-(Z)-(1-{4-[N-acetyl-N-(2-dimethylaminoethyl)-amino]-anilino}-1-ethyl-methylidene)-5,6-dimethoxy-2-indolinone
(160) 3-(Z)-(1-{4-[N-acetyl-N-(3-amino-propyl)-amino]-anilino}-1-ethyl-methylidene)-5,6-dimethoxy-2-indolinone
(161) 3-(Z)-(1-{4-[N-acetyl-N-(2-methylamino-propyl)-amino]-anilino}-1-ethyl-methylidene)-5,6-dimethoxy-2-indolinone
(162) 3-(Z)-(1-{4-[N-acetyl-N-(2-piperidin-1-yl-ethyl)-amino]-anilino}-1-ethyl-methylidene)-5,6-dimethoxy-2-indolinone
(163) 3-(Z)-(1-{4-[N-acetyl-N-(aminocarbonylmethyl)-amino]-anilino}-1-ethyl-methylidene)-5,6-dimethoxy-2-indolinone
(164) 3-(Z)-(1-{4-[N-acetyl-N-(dimethylaminocarbonylmethyl)-amino]-anilino}-1-ethyl-methylidene)-5,6-dimethoxy-2-indolinone
(165) 3-(Z)-(1-{4-[N-acetyl-N-(piperidin-1-yl-carbonylmethyl)-amino]-anilino}-1-ethyl-methylidene)-5,6-dimethoxy-2-indolinone
(166) 3-(Z)-(1-{4-[N-methyl-N-(aminocarbonyl)-amino]-anilino}-1-ethyl-methylidene)-5,6-dimethoxy-2-indolinone (167) 3-(Z)-(1-{4-[N-methyl-N-(methylaminocarbonyl)-amino]-anilino}-1-ethyl-methylidene)-5,6-dimethoxy-2-indolinone
(168) 3-(Z)-(1-{4-[N-methyl-N-(dimethylaminocarbonyl)-amino]-anilino}-1-ethyl-methylidene)-5,6-dimethoxy-2-indolinone
(169) 3-(Z)-(1-{4-[N-methyl-N-(piperidin-1-yl-carbonyl)amino]-anilino}-1-ethyl-methylidene)-5,6-dimethoxy-2-indolinone
(170) 3-(Z)-(1-{4-[N-(2-aminoethyl)-N-methylsulphonyl-amino]-anilino}-1-ethyl-methylidene)-5,6-dimethoxy-2-indolinone
(171) 3-(Z)-(1-{4-[N-(2-methylamino-ethyl)-N-methylsulphonyl-amino]-anilino}-1-ethyl-methylidene)-5,6-dimethoxy-2-indolinone
(172) 3-(Z)-(1-{4-[N-(2-ethylamino-ethyl)-N-methylsulphonyl-amino]-anilino}-1-ethyl-methylidene)-5,6-dimethoxy-2-indolinone
(173) 3-(Z)-(1-{4-[N-(2-diethylamino-ethyl)-N-methylsulphonyl-amino]-anilino}-1-ethyl-methylidene)-5,6-dimethoxy-2-indolinone
(174) 3-(Z)-(1-{4-[N-(2-pyrrolidin-1-yl-ethyl)-N-methylsulphonyl-amino]-anilino}-1-ethyl-methylidene)-5,6-dimethoxy-2-indolinone
(175) 3-(Z)-(1-{4-[N-(2-piperidin-1-yl-ethyl)-N-methylsulphonyl-amino]-anilino}-1-ethyl-methylidene)-5,6-dimethoxy-2-indolinone
(176) 3-(Z)-(1-{4-[N-(2-piperazin-1-yl-ethyl)-N-methylsulphonyl-amino]-anilino}-1-ethyl-methylidene)-5,6-dimethoxy-2-indolinone
(177) 3-(Z)-[1-(4-{N-(2-(morpholin-4-yl)-ethyl]-N-methylsulphonyl-amino}-anilino)-1-ethyl-methylidene]-5,6-dimethoxy-2-indolinone
(178) 3-(Z)-(1-{4-[N-(aminocarbonylmethyl)-N-methylsulphonyl-amino]-anilino}-1-ethyl-methylidene)-5,6-dimethoxy-2-indolinone
(179) 3-(Z)-(1-{4-[N-(methylaminocarbonylmethyl)-N-methylsulphonyl-amino]-anilino}-1-ethyl-methylidene)-5,6-dimethoxy-2-indolinone
(180) 3-(Z)-(1-{4-[N-(ethylaminocarbonylmethyl)-N-methylsulphonyl-amino]-anilino}-1-ethyl-methylidene)-5,6-dimethoxy-2-indolinone
(181) 3-(Z)-[1-(4-{N-[(2-dimethylamino-ethylamino)-carbonylmethyl]-N-methylsulphonyl-amino}-anilino)-1-ethyl-methylidene]-5,6-dimethoxy-2-indolinone
(182) 3-(Z)-[1-(4-{N-[N-(2-dimethylamino-ethyl)-N-methyl-amino)-carbonylmethyl]-N-methylsulphonyl-amino}-anilino)-1-ethyl-methylidene]-5,6-dimethoxy-2-indolinone
(183) 3-(Z)-(1-{4-[N-(diethylaminocarbonylmethyl)-N-methylsulphonyl-amino]-anilino}-1-ethyl-methylidene)-5,6-dimethoxy-2-indolinone
(184) 3-(Z)-(1-{4-[N-(pyrrolidin-1-yl-carbonylmethyl)-N-methylsulphonyl-amino]-anilino}-1-ethyl-methylidene)-5,6-dimethoxy-2-indolinone
(185) 3-(Z)-(1-{4-[N-(piperidin-1-yl-carbonylmethyl)-N-methylsulphonyl-amino]-anilino}-1-ethyl-methylidene)-5,6-dimethoxy-2-indolinone
(186) 3-(Z)-(1-{4-[N-(piperazin-1-yl-carbonylmethyl)-N-methylsulphonyl-amino]-anilino}-1-ethyl-methylidene)-5,6-dimethoxy-2-indolinone
(187) 3-(Z)-[1-[4-{N-[(morpholin-4-yl)-carbonylmethyl]-N-methylsulphonyl-amino]-anilino}-1-ethyl-methylidene]-5,6-dimethoxy-2-indolinone
(188) 3-(Z)-{1-[4-(2-dimethylamino-ethoxy)-anilino]-1-ethyl-methylidene}-5,6-dimethoxy-2-indolinone
(189) 3-(Z)-{1-[4-(3-dimethylamino-propoxy)-anilino]-1-ethyl-methylidene}-5,6-dimethoxy-2-indolinone
(190) 3-(Z)-{1-[4-(2-aminocarbonyl-ethyl)-anilino]-1-ethyl-methylidene}-5,6-dimethoxy-2-indolinone
(191) 3-(Z)-{1-[4-(1H-imidazol-4-yl)-anilino]-1-ethyl-methylidene}-5,6-dimethoxy-2-indolinone
(192) 3-(Z)-{1-[4-(pyridine-2-yl)-anilino]-1-ethyl-methylidene}-5,6-dimethoxy-2-indolinone
(193) 3-(Z)-{1-[4-(pyridine-3-yl)-anilino]-1-ethyl-methylidene}-5,6-dimethoxy-2-indolinone
(194) 3-(Z)-{1-[4-(pyridine-4-yl)-anilino]-1-ethyl-methylidene}-5,6-dimethoxy-2-indolinone
(195) 3-(Z)-(1-anilino-1-phenyl-methylidene)-5,6-diethoxy-2-indolinone
(196) 3-(Z)-[1-(4-nitro-anilino)-1-phenyl-methylidene]-5,6-diethoxy-2-indolinone
(197) 3-(Z)-[1-(4-ethoxycarbonyl-anilino)-1-phenyl-methylidene]-5,6-diethoxy-2-indolinone
(198) 3-(Z)-[1-(4-carboxy-anilino)-1-phenyl-methylidene]-5,6-diethoxy-2-indolinone
(199) 3-(Z)-1-[(4-fluoro-anilino)-1-phenyl-methylidene]-5,6-diethoxy-2-indolinone
(200) 3-(Z)-1-[(4-chloro-anilino)-1-phenyl-methylidene]-5,6-diethoxy-2-indolinone
(201) 3-(Z)-[1-(4-bromo-anilino)-1-phenyl-methylidene]-5,6-diethoxy-2-indolinone
(202) 3-(Z)-[1-(4-iodo-anilino)-1-phenyl-methylidene]-5,6-diethoxy-2-indolinone
(203) 3-(Z)-[1-(4-cyano-anilino)-1-phenyl-methylidene]-5,6-diethoxy-2-indolinone
(204) 3-(Z)-[1-(4-methoxy-anilino)-1-phenyl-methylidene]-5,6-diethoxy-2-indolinone
(205) 3-(Z)-[1-(4-ethoxy-anilino)-1-phenyl-methylidene]-5,6-diethoxy-2-indolinone
(206) 3-(Z)-[1-(4-trifluoromethyl-anilino)-1-phenyl-methylidene]-5,6-diethoxy-2-indolinone
(207) 3-(Z)-[1-(4-methyl-anilino)-1-phenyl-methylidene]-5,6-diethoxy-2-indolinone
(208) 3-(Z)-[1-(4-methylmercapto-anilino)-1-phenyl-methylidene]-5,6-diethoxy-2-indolinone
(209) 3-(Z)-[1-(4-aminomethyl-anilino)-1-phenyl-methylidene]-5,6-diethoxy-2-indolinone
(210) 3-(Z)-{1-[4-(methylaminomethyl)-anilino]-1-phenyl-methylidene}-5,6-diethoxy-2-indolinone
(211) 3-(Z)-{1-[4-(isopropylaminomethyl)-anilino]-1-phenyl-methylidene}-5,6-diethoxy-2-indolinone
(212) 3-(Z)-{1-[4-(phenylaminomethyl)-anilino]-1-phenyl-methylidene}-5,6-diethoxy-2-indolinone
(213) 3-(Z)-{1-[4-(ethylaminomethyl)-anilino]-1-phenyl-methylidene}-5,6-diethoxy-2-indolinone
(214) 3-(Z)-{1-[4-(propylaminomethyl)-anilino]-1-phenyl-methylidene}5,6-diethoxy-2-indolinone
(215) 3-(Z)-{1-[4-(butylaminomethyl)-anilino]-1-phenyl-methylidene}-5,6-diethoxy-2-indolinone
(216) 3-(Z)-{1-[4-(isobutylaminomethyl)-anilino]-1-phenyl-methylidene}-5,6-diethoxy-2-indolinone
(217) 3-(Z)-{1-[4-(cyclohexylaminomethyl)-anilino]-1-phenyl-methylidene}-5,6-diethoxy-2-indolinone
(218) 3-(Z)-{1-[4-(benzylaminomethyl)-anilino]-1-phenyl-methylidene}-5,6-diethoxy-2-indolinone
(219) 3-(Z)-{1-[4-(dimethylaminomethyl)-anilino]-1-phenyl-methylidene}-5,6-diethoxy-2-indolinone
(220) 3-(Z)-{1-[3-(dimethylaminomethyl)-anilino]-1-phenyl-methylidene}-5,6-diethoxy-2-indolinone
(221) 3-(Z)-(1-{4-[(N-ethyl-N-methyl-amino)-methyl]-anilino}-1-phenyl-methylidene)-5,6-diethoxy-2-indolinone
(222) 3-(Z)-{1-[4-(diethylaminomethyl)-anilino]-1-phenyl-methylidene}-5,6-diethoxy-2-indolinone (223) 3-(Z)-(1-{4-[(N-methyl-N-propyl-amino)-methyl]-anilino}-1-phenyl-methylidene) 5,6-diethoxy-2-indolinone
(224) 3-(Z)-(1-{4-[(N-isopropyl-N-methyl-amino)-methyl]-anilino}-1-phenyl-methylidene)-5,6-diethoxy-2-indolinone
(225) 3-(Z)-(1-{4-[(N-ethyl-N-propyl-amino)-methyl]-anilino}-1-phenyl-methylidene)-5,6-diethoxy-2-indolinone
(226) 3-(Z)-(1-{4-[(N-ethyl-N-isopropyl-amino)-methyl]-anilino}-1-phenyl-methylidene)-5,6-diethoxy-2-indolinone
(227) 3-(Z)-{1-[4-(dipropylaminomethyl)-anilino]-1-phenyl-methylidene}-5,6-diethoxy-2-indolinone
(228) 3-(Z)-{1-[4-(diisopropylaminomethyl)-anilino]-1-phenyl-methylidene}-5,6-diethoxy-2-indolinone
(229) 3-(Z)-(1-{4-[(N-benzyl-N-methyl-amino)-methyl]-anilino}-1-phenyl-methylidene)-5,6-diethoxy-2-indolinone
(230) 3-(Z)-(1-{4-[(N-benzyl-N-ethyl-amino)-methyl]-anilino}-1-phenyl-methylidene)-5,6-diethoxy-2-indolinone
(231) 3-(Z)-{1-[4-(dibenzylaminomethyl)-anilino]-1-phenyl-methylidene}-5,6-diethoxy-2-indolinone
(232) 3-(Z)-{1-[4-(pyrrolidin-1-yl-methyl)-anilino]-1-phenyl-methylidene}-5,6-diethoxy-2-indolinone
(233) 3-(Z)-{1-[4-(3,6-dihydro-2H-pyridine-1-yl-methyl)-anilino]-1-phenyl-methylidene}-5,6-diethoxy-2-indolinone
(234) 3-(Z)-{1-[4-(2,6-dimethyl-piperidin-1-yl-methyl)-anilino]-1-phenyl-methylidene}-5,6-diethoxy-2-indolinone
(235) 3-(Z)-{1-[4-(3,5-dimethyl-piperidin-1-yl-methyl)-anilino]-1-phenyl-methylidene}-5,6-diethoxy-2-indolinone
(236) 3-(Z)-{i-[4-(azepan-1-yl-methyl)-anilino]-1-phenyl-methylidene}-5,6-diethoxy-2-indolinone
(237) 3-(Z)-{1-[4-(piperazin-1-yl-methyl)-anilino]-1-phenyl-methylidene}-5,6-diethoxy-2-indolinone
(238) 3-(Z)-{1-[4-(morpholin-4-yl-methyl)-anilino]-1-phenyl-methylidene}-5,6-diethoxy-2-indolinone
(239) 3-(Z)-{1-[4-(thiomorpholin-4-yl-methyl)-anilino]-1-phenyl-methylidene}-5,6-diethoxy-2-indolinone
(240) 3-(Z)-{1-[4-(1-oxo-thiomorpholin-4-yl-methyl)-anilino]-1-phenyl-methylidene}-5,6-diethoxy-2-indolinone
(241) 3-(Z)-{1-[4-(acetylamino-methyl)-anilino]-1-phenyl-methylidene}-5,6-diethoxy-2-indolinone
(242) 3-(Z)-{1-[4-(2-amino-ethyl)-anilino]-1-phenyl-methylidene}-5,6-diethoxy-2-indolinone
(243) 3-(Z)-{1-[4-(2-methylamino-ethyl)-anilino]-1-phenyl-methylidene}-5,6-diethoxy-2-indolinone
(244) 3-(Z)-{1-[4-(2-ethylamino-ethyl)-anilino]-1-phenyl-methylidene}-5,6-diethoxy-2-indolinone
(245) 3-(Z)-{1-[4-(2-dimethylamino-ethyl)-anilino]-1-phenyl-methylidene}-5,6-diethoxy-2-indolinone
(246) 3-(Z)-{1-[4-(2-diethylamino-ethyl)-anilino]-1-phenyl-methylidene}-5,6-diethoxy-2-indolinone
(247) 3-(Z)-{1-[4-(2-piperidin-1-yl-ethyl)-anilino]-1-phenyl-methylidene}-5,6-diethoxy-2-indolinone
(248) 3-(Z)-(1-{4-[2-(4-ethoxycarbonyl-piperidin-1-yl)-ethyl]-anilino}-1-phenyl-methylidene)-5,6-diethoxy-2-indolinone
(249) 3-(Z)-(1-{4-[2-(4-carboxy-piperidin-1-yl)-ethyl]-anilino}-1-phenyl-methylidene)-5,6-diethoxy-2-indolinone
(250) 3-(Z)-(1-{4-(2-(4-dimethylcarbamoyl-piperidin-1-yl)-ethyl]-anilino}-1-phenyl-methylidene)-5,6-diethoxy-2-indolinone
(251) 3-(Z)-{1-[4-(2-acetylamino-ethyl)-anilino]-1-phenyl-methylidene}-5,6-diethoxy-2-indolinone
(252) 3-(Z)-{1-[4-(3-amino-propyl)-anilino]-1-phenyl-methylidene}-5,6-diethoxy-2-indolinone
(253) 3-(Z)-{1-[4-(3-dimethylamino-propyl)-amino]-1-phenyl-methylidene}-5,6-diethoxy-2-indolinone
(254) 3-(Z)-{1-[4-(N-aminomethylcarbonyl-N-methyl-amino)-anilino]-1-phenyl-methylidene}-5,6-diethoxy-2-indolinone
(255) 3-(Z)-{1-[4-(N-methylaminomethylcarbonyl-N-methyl-amino)-anilino]-1-phenyl-methylidene}-5,6-diethoxy-2-indolinone
(256) 3-(Z)-{1-[4-(N-dimethylaminomethylcarbonyl-N-methyl-amino)-anilino]-1-phenyl-methylidene}-5,6-diethoxy-2-indolinone
(257) 3-(Z)-{1-[4-(N-ethylaminomethylcarbonyl-N-methyl-amino)-anilino]-1-phenyl-methylidene}-5,6-diethoxy-2-indolinone
(258) 3-(Z)-{1-[4-(N-diethylaminomethylcarbonyl-N-methyl-amino)-anilino]-1-phenyl-methylidene}-5,6-diethoxy-2-indolinone
(259) 3-(Z)-(1-{4-[N-(piperidin-1-yl-methylcarbonyl)-N-methyl-amino]-anilino}-1-phenyl-methylidene)-5,6-diethoxy-2-indolinone
(260) 3-(Z)-(1-{4-[N-(morpholin-4-yl-methylcarbonyl)-N-methyl-amino]-anilino}-1-phenyl-methylidene)-5,6-diethoxy-2-indolinone
(261) 3-(Z)-(1-{4-[N-(piperazin-1-yl-methylcarbonyl)-N-methyl-amino]-anilino}-1-phenyl-methylidene)-5,6-diethoxy-2-indolinone
(262) 3-(Z)-(1-{4-[N-(2-amino-ethyl-carbonyl)-N-methyl-amino]-anilino}-1-phenyl-methylidene)-5,6-diethoxy-2-indolinone
(263) 3-(Z)-(1-{4-[N-(2-methylamino-ethyl-carbonyl)-N-methyl-amino]-anilino}-1-phenyl-methylidene)-5,6-diethoxy-2-indolinone
(264) 3-(Z)-(1-{4-[N-(2-diethylamino-ethyl-carbonyl)-N-methyl-amino]-anilino}-1-phenyl-methylidene)-5,6-diethoxy-2-indolinone
(265) 3-(Z)-(1-{4-[N-acetyl-N-(2-aminoethyl)-amino]-anilino}-1-phenyl-methylidene)-5,6-diethoxy-2-indolinone
(266) 3-(Z)-(1-{4-[N-acetyl-N-(2-methylamino-ethyl)-amino]-anilino}-1-phenyl-methylidene)-5,6-diethoxy-2-indolinone
(267) 3-(Z)-(1-{4-[N-acetyl-N-(2-dimethylaminoethyl)-amino]-anilino}-1-phenyl-methylidene)-5,6-diethoxy-2-indolinone
(268) 3-(Z)-(1-{4-[N-acetyl-N-(3-amino-propyl)-amino]-anilino}-1-phenyl-methylidene)-5,6-diethoxy-2-indolinone
(269) 3-(Z)-(1-{4-[N-acetyl-N-(3-dimethylamino-propyl)-amino]-anilino}-1-phenyl-methylidene)-5,6-diethoxy-2-indolinone
(270) 3-(Z)-(1-{4-[N-acetyl-N-(2-methylamino-propyl)-amino]-anilino}-1-phenyl-methylidene)-5,6-diethoxy-2-indolinone
(271) 3-(Z)-(1-{4-[N-acetyl-N-(2-piperidin-1-yl-ethyl)-amino]-anilino}-1-phenyl-methylidene)-5,6-diethoxy-2-indolinone
(272) 3-(Z)-(1-{4-[N-acetyl-N-(aminocarbonylmethyl)-amino]-anilino}-1-phenyl-methylidene)-5,6-diethoxy-2-indolinone
(273) 3-(Z)-(1-{4-[N-acetyl-N-(dimethylaminocarbonylmethyl)-amino]-anilino}-1-phenyl-methylidene)-5,6-diethoxy-2-indolinone
(274) 3-(Z)-(1-{4-[N-acetyl-N-(piperidin-1-yl-carbonylmethyl)-amino]-anilino}-1-phenyl-methylidene)-5,6-diethoxy-2-indolinone (275) 3-(Z)-(1-{4-(N-methyl-N-(aminocarbonyl)-amino]-anilino}-1-phenyl-methylidene)-5,6-diethoxy-2-indolinone
(276) 3-(Z)-(1-{4-[N-methyl-N-(methylaminocarbonyl)-amino]-anilino}-1-phenyl-methylidene)-5,6-diethoxy-2-indolinone
(277) 3-(Z)-(1-{4-[N-methyl-N-(dimethylaminocarbonyl)-amino]-anilino}-1-phenyl-methylidene)-5,6-diethoxy-2-indolinone
(278) 3-(Z)-(1-{4-[N-methyl-N-(piperidin-1-yl-carbonyl)-amino]-anilino}-1-phenyl-methylidene)-5,6-diethoxy-2-indolinone
(279) 3-(Z)-(1-{4-[N-(2-aminoethyl)-N-methylsulphonyl-amino]-anilino}-1-phenyl-methylidene)-5,6-diethoxy-2-indolinone
(280) 3-(Z)-(1-{4-[N-(2-methylamino-ethyl)-N-methylsulphonyl-amino]-anilino}-1-phenyl-methylidene)-5,6-diethoxy-2-indolinone
(281) 3-(Z)-(1-{4-[N-(2-ethylamino-ethyl)-N-methylsulphonyl-amino]-anilino}-1-phenyl-methylidene)-5,6-diethoxy-2-indolinone
(282) 3-(Z)-(1-{4-[N-(2-dimethylamino-ethyl)-N-methylsulphonyl-amino]-anilino}-1-phenyl-methylidene)-5,6-diethoxy-2-indolinone
(283) 3-(Z)-(1-{4-[N-(2-diethylamino-ethyl)-N-methylsulphonyl-amino)-anilino}-1-phenyl-methylidene)-5,6-diethoxy-2-indolinone
(284) 3-(Z)-(1-{4-[N-(2-pyrrolidin-1-yl-ethyl)-N-methylsulphonyl-amino]-anilino}-1-phenyl-methylidene)-5,6-diethoxy-2-indolinone
(285) 3-(Z)-(1-{4-[N-(2-piperidin-1-yl-ethyl)-N-methylsulphonyl-amino]-anilino}-1-phenyl-methylidene)-5,6-diethoxy-2-indolinone
(286) 3-(Z)-(!-{4-[N-(2-piperazin-1-yl-ethyl)-N-methylsulphonyl-amino]-anilino}-1-phenyl-methylidene)-5,6-diethoxy-2-indolinone
(287) 3-(Z)-[1-(4-{N-[2-(morpholin-4-yl)-ethyl]-N-methylsulphonyl-amino}-anilino)-1-phenyl-methylidene]-5,6-diethoxy-2-indolinone
(288) 3-(Z)-(1-{4-[N-(aminocarbonylmethyl)-N-methylsulphonyl-amino]-anilino}-1-phenyl-methylidene)-5,6-diethoxy-2-indolinone
(289) 3-(Z)-(1-{4-[N-(methylaminocarbonylmethyl)-N-methylsulphonyl-amino]-anilino}-1-phenyl-methylidene)-5,6-diethoxy-2-indolinone
(290) 3-(Z)-(1-{4-[N-(ethylaminocarbonylmethyl)-N-methylsulphonyl-amino]-anilino}-1-phenyl-methylidene)-5,6-diethoxy-2-indolinone
(291) 3-(Z)-[1-(4-{N-[(2-dimethylamino-ethylamino)-carbonylmethyl]-N-methylsulphonyl-amino}-anilino)-1-phenyl-methylidene]-5,6-diethoxy-2-indolinone
(292) 3-(Z)-[1-(4-{N-[N-(2-dimethylamino-ethyl)-N-methyl-amino)-carbonylmethyl]-N-methylsulphonyl-amino}-anilino)-1-phenyl-methylidene]-5,6-diethoxy-2-indolinone
(293) 3-(Z)-(1-{4-[N-(dimethylaminocarbonylmethyl)-N-methyl-sulphonyl-amino]-anilino}-1-phenyl-methylidene)-5,6-diethoxy-2-indolinone
(294) 3-(Z)-(1-{4-[N-(diethylaminocarbonylmethyl)-N-methylsulphonyl-amino]-anilino}-1-phenyl-methylidene)-5,6-diethoxy-2-indolinone
(295) 3-(Z)-(1-{4-[N-(pyrrolidin-1-yl-carbonylmethyl)-N-methylsulphonyl-amino]-anilino}-1-phenyl-methylidene)-5,6-diethoxy-2-indolinone
(296) 3-(Z)-(1-{4-[N-(piperidin-1-yl-carbonylmethyl)-N-methyl-sulphonyl-amino]-anilino}-1-phenyl-methylidene)-5,6-diethoxy-2-indolinone
(297) 3-(Z)-(1-{4-[N-(piperazin-1-yl-carbonylmethyl)-N-methyl-sulphonyl-amino]-anilino}-1-phenyl-methylidene)-5,6-diethoxy-2-indolinone
(298) 3-(Z)-[1-[4-{N-[(morpholin-4-yl)-carbonylmethyl]-N-methylsulphonyl-amino]-anilino]-1-phenyl-methylidene]-5,6-diethoxy-2-indolinone
(299) 3-(Z)-{1-[4-(2-dimethylamino-ethoxy)-anilino]-1-phenyl-methylidene}-5,6-diethoxy-2-indolinone
(300) 3-(Z)-{1-[4-(3-dimethylamino-propoxy)-anilino]-1-phenyl-methylidene}-5,6-diethoxy-2-indolinone
(301) 3-(Z)-{1-[4-(aminocarbonylmethyl)-anilino]-1-phenyl-methylidene}-5,6-diethoxy-2-indolinone
(302) 3-(Z)-{1-[4-(2-aminocarbonyl-ethyl)-anilino]-1-phenyl-methylidene}-5,6-diethoxy-2-indolinone
(303) 3-(Z)-{1-[4-(1H-imidazol-4-yl)-anilino]-1-phenyl-methylidene}-5,6-diethoxy-2-indolinone
(304) 3-(Z)-{1-[4-(pyridine-2-yl)-anilino]-1-phenyl-methylidene}-5,6-diethoxy-2-indolinone
(305) 3-(Z)-{1-[4-(pyridine-3-yl)-anilino]-1-phenyl-methylidene}-5,6-diethoxy-2-indolinone
(306) 3-(Z)-{1-[4-(pyridine-4-yl)-anilino]-1-phenyl-methylidene}-5,6-diethoxy-2-indolinone

EXAMPLE 12

Dry ampoule containing 75 mg of active substance per 10 ml
Composition:

| Active substance | 75.0 mg |
|---|---|
| Mannitol | 50.0 mg |
| water for injections | ad 10.0 ml |

Preparation:
Active substance and mannitol are dissolved in water. After packaging the solution is freeze-dried. To produce the solution ready for use, the product is dissolved in water for injections.

EXAMPLE 13

Dry ampoule containing 35 mg of active substance per 2 ml
Composition:

| Active substance | 35.0 mg |
|---|---|
| Mannitol | 100.0 mg |
| water for injections | ad 2.0 ml |

Preparation:
Active substance and mannitol are dissolved in water. After packaging, the solution is freeze-dried.
To produce the solution ready for use, the product is dissolved in water for injections.

EXAMPLE 14

Tablet containing 50 mg of active substance
Composition:

| (1) | Active substance | 50.0 mg |
|---|---|---|
| (2) | Lactose | 98.0 mg |
| (3) | Maize starch | 50.0 mg |

-continued

| | | |
|---|---|---|
| (4) | Polyvinylpyrrolidone | 15.0 mg |
| (5) | Magnesium stearate | 2.0 mg |
| | | 215.0 mg |

Preparation:

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 9 mm.

EXAMPLE 15

Tablet containing 350 mg of active substance
Preparation:

| | | |
|---|---|---|
| (1) | Active substance | 350.0 mg |
| (2) | Lactose | 136.0 mg |
| (3) | Maize starch | 80.0 mg |
| (4) | Polyvinylpyrrolidone | 30.0 mg |
| (5) | Magnesium stearate | 4.0 mg |
| | | 600.0 mg |

(1), (2) and (3) are mixed together and granulated with an aqueous solution of (4). (5) is added to the dried granulated material. From this mixture tablets are pressed, biplanar, faceted on both sides and with a dividing notch on one side. Diameter of the tablets: 12 mm.

EXAMPLE 16

Capsules containing 50 mg of active substance
Composition:

| | | |
|---|---|---|
| (1) | Active substance | 50.0 mg |
| (2) | Dried maize starch | 58.0 mg |
| (3) | Powdered lactose | 50.0 mg |
| (4) | Magnesium stearate | 2.0 mg |
| | | 160.0 mg |

Preparation:

(1) is triturated with (3). This trituration is added to the mixture of (2) and (4) with vigorous mixing.

This powder mixture is packed into size 3 hard gelatin capsules in a capsule filling machine.

EXAMPLE 17

Capsules containing 350 mg of active substance
Composition:

| | | |
|---|---|---|
| (1) | Active substance | 350.0 mg |
| (2) | Dried maize starch | 46.0 mg |
| (3) | Powdered lactose | 30.0 mg |
| (4) | Magnesium stearate | 4.0 mg |
| | | 430.0 mg |

Preparation:

(1) is triturated with (3). This trituration is added to the mixture of (2) and (4) with vigorous mixing.

This powder mixture is packed into size 0 hard gelatin capsules in a capsule filling machine.

EXAMPLE 18

Suppositories containing 100 mg of active substance

| 1 suppository contains: | |
|---|---|
| Active substance | 100.0 mg |
| Polyethyleneglycol (M.W. 1500) | 600.0 mg |
| Polyethyleneglycol (M.W. 6000) | 460.0 mg |
| Polyethylenesorbitan monostearate | 840.0 mg |
| | 2,000.0 mg |

Preparation:

The polyethyleneglycol is melted together with polyethylene sorbitanmonostearate. At 40° C. the ground active substance is homogeneously dispersed in the melt. It is cooled to 38° C. and poured into slightly chilled suppository moulds.

What is claimed is:

1. A compound of the formula (I):

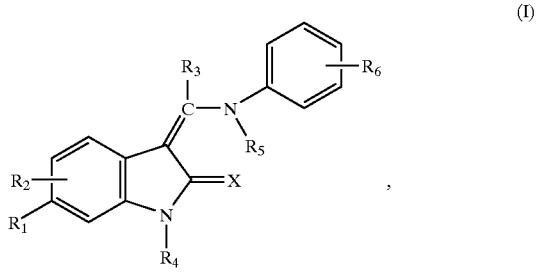

wherein:

X denotes an oxygen or sulphur atom;

$R_1$ denotes a $C_{2-3}$-alkenyl, $C_{2-3}$-alkynyl, aryl, aryl-$C_{1-3}$-alkyl, heteroaryl, heteroaryl-$C_{1-3}$-alkyl, trifluoromethyl or cyano group, a hydroxy, $C_{1-3}$-alkoxy, hydroxy-$C_{1-3}$-alkyl, $C_{1-3}$-alkoxy-$C_{1-3}$-alkyl, aryloxy or heteroaryloxy group, a mercapto, $C_{1-3}$-alkylsulphenyl, phenylsulphenyl, benzylsulphenyl, $C_{1-3}$-alkylsulphinyl, phenylsulphinyl, benzylsulphinyl, $C_{1-3}$-alkylsulphonyl, phenylsulphonyl, benzylsulphonyl, sulpho, $C_{1-3}$-alkoxysulphonyl, phenoxysulphonyl or benzyloxysulphonyl group, an amino, $C_{1-3}$-alkylamino, di-($C_{1-3}$-alkyl)-amino, hydroxycarbonyl-$C_{1-3}$-alkylamino, N—($C_{1-3}$-alkyl)-hydroxycarbonyl-$C_{1-3}$-alkylamino, $C_{1-3}$-alkoxycarbonyl-$C_{1-3}$-alkylamino, N—($C_{1-3}$-alkyl)-$C_{1-3}$-alkoxycarbonyl-$C_{1-3}$-alkyl amino, phenylamino, N-phenyl-$C_{1-3}$-alkylamino, N,N-diphenylamino, benzylamino, N-benzyl-$C_{1-3}$-alkylamino, N,N-dibenzylamino, $C_{1-3}$-alkylcarbonylamino, benzoylamino, benzylcarbonylamino group or an N—($C_{1-3}$-alkyl)-$C_{1-3}$-alkylcarbonylamino group wherein the two alkyl groups are optionally replaced by a $C_{2-5}$-n-alkylene bridge or wherein one or both alkyl groups are optionally replaced by a phenyl or benzyl group, a $C_{1-3}$-alkylsulphonylamino, phenylsulphonylamino or benzylsulphonylamino group or an N—($C_{1-3}$-alkyl)-$C_{1-3}$-alkylsulphonylamino group wherein the two alkyl groups are optionally replaced by a C$_{2-5}$-n-alkylene bridge or wherein one or both alkyl groups are optionally replaced by a phenyl or benzyl group, an aminosulphonyl, C$_{1-3}$-alkylaminosulphonyl, phenylaminosulphonyl, benzylaminosulphonyl, di-(C$_{1-3}$-alkyl)-aminosulphonyl, N,N-diphenyl-aminosulphonyl or N,N-dibenzyl-aminosulphonyl group, a phosphono, (C$_{1-3}$-alkoxy)PO(H), (C$_{1-3}$-alkoxy)PO(C$_{1-3}$-alkyl), (C$_{1-3}$-alkoxy)PO(OH), di-(C$_{1-3}$-alkoxy)-PO or (C$_{2-4}$-n-alkylenedioxy)-PO group, a ureido group optionally mono-, di- or trisubstituted by C$_{1-3}$-alkyl groups, a 4- to 7-membered cycloalkyleneimino or cycloalkyleneiminosulphonyl group, wherein in each case the methylene group in the 4 position of a 6- or 7-membered cycloalkyleneimino group is optionally replaced by an oxygen or sulphur atom, by a sulphinyl, sulphonyl, —NH or —N(C$_{1-3}$-alkyl) group;

R$_2$ denotes a hydrogen, fluorine, chlorine, bromine or iodine atom, a C$_{1-6}$-alkyl or trifluoromethyl group, a hydroxy, C$_{1-3}$-alkoxy, mercapto, C$_{1-3}$-alkylsulphenyl, C$_{1-3}$-alkylsulphinyl, C$_{1-3}$-alkylsulphonyl, sulpho, C$_{1-3}$-alkoxysulphonyl, aminosulphonyl, C$_{1-3}$-alkylaminosulphonyl or di-(C$_{1-3}$-alkyl)-aminosulphonyl group, a nitro, amino, C$_{1-3}$-alkylamino or di-(C$_{1-3}$-alkyl)-amino group, a C$_{1-3}$-alkylcarbonyl, cyano, carboxy, C$_{1-3}$-alkoxycarbonyl, aminocarbonyl, C$_{1-3}$-alkylaminocarbonyl or di-(C$_{1-3}$-alkyl)-aminocarbonyl group, a phosphono, (C$_{1-3}$-alkoxy)PO(H), (C$_{1-3}$-alkoxy)PO(C$_{1-3}$-alkyl), (C$_{1-3}$-alkoxy)PO(OH) or di-(C$_{1-3}$-alkoxy)-PO group, a 4- to 7-membered cycloalkyleneimino, cycloalkyleneiminocarbonyl or cycloalkyleneiminosulphonyl group, wherein in each case the methylene group in the 4 position of a 6- or 7-membered cycloalkyleneimino group is optionally replaced by an oxygen or sulphur atom, by a sulphinyl, sulphonyl, —NH or —N(C$_{1-3}$-alkyl) group, or R$_1$ and R$_2$ together denote a methylenedioxy, ethylenedioxy, n-propylene, n-butylene or 1,4-butadienylene group;

R$_3$ denotes a phenyl;

R$_4$ denotes a hydrogen atom or a C$_{1-3}$-alkyl group;

R$_5$ denotes a hydrogen atom or a C$_{1-3}$-alkyl group and

R$_6$ denotes a hydrogen, fluorine, chlorine, bromine or iodine atom, a trifluoromethyl or heteroaryl group, a C$_{1-3}$-alkoxy group optionally substituted by 1 to 3 fluorine atoms, an amino-C$_{1-3}$-alkoxy, C$_{1-3}$-alkylamino-C$_{2-3}$-alkoxy or benzylamino-C$_{2-3}$-alkoxy group, a cycloalkyleneimino-C$_{2-3}$-alkoxy group with 4 to 7 ring members, a di-(C$_{1-13}$-alkyl)-amino-C$_{2-3}$-alkoxy or C$_{1-3}$-alkylmercapto group, a nitro, cyano, carboxy, C$_{1-3}$-alkoxycarbonyl, aminocarbonyl, C$_{1-3}$-alkylaminocarbonyl, di-(C$_{1-3}$-alkyl)-aminocarbonyl, piperidinocarbonyl or tetrazolyl group, a C$_{1-3}$-alkylcarbonylamino group optionally substituted at the nitrogen atom by a C$_{1-3}$-alkyl group, an imidazolyl or piperazino group optionally substituted at the imino group by a C$_{1-3}$-alkyl group, a C$_{1-4}$-alkyl group, which may be terminally substituted by a hydroxy, C$_{1-3}$-alkoxy, carboxy, C$_{1-3}$-alkoxycarbonyl, amino, C$_{1-4}$-alkylamino, di-(C$_{1-4}$-alkyl)-amino, phenylamino, N-phenyl-C$_{1-3}$-alkylamino, phenyl-n-C$_{1-3}$-alkylamino, N—(C$_{1-3}$-alkyl)-phenyl-n-C$_{1-3}$-alkylamino or di-(phenyl-n-C$_{1-3}$-alkyl)-amino group, by a 4- to 7-membered cycloalkyleneimino group wherein a methylene group linked to the imino group is optionally replaced by a carbonyl or sulphonyl group or one or two hydrogen atoms is optionally replaced by a C$_{1-3}$-alkyl group and/or in each case the methylene group in the 4 position of a 6- or 7-membered cycloalkyleneimino group is optionally substituted by a carboxy, C$_{1-3}$-alkoxycarbonyl, aminocarbonyl, C$_{1-3}$-alkylaminocarbonyl, di-(C$_{1-3}$-alkyl)-aminocarbonyl, phenyl-n-C$_{1-3}$-alkylamino or N—(C$_{1-3}$-alkyl)-phenyl-n-C$_{1-3}$-alkylamino group or is optionally replaced by an oxygen or sulphur atom, by a sulphinyl, sulphonyl, —NH or —N(C$_{1-3}$-alkyl) group, by a 5- to 7-membered cycloalkenyleneimino group wherein the double bond is isolated from the nitrogen atom, by a C$_{4-7}$-cycloalkylamino, N—(C$_{1-3}$-alkyl)-C$_{4-7}$-cycloalkylamino or C$_{5-7}$-cycloalkenylamino group wherein position 1 of the ring is not involved in the double bond and wherein the nitrogen atom is optionally substituted by a C$_{1-3}$-alkyl group, by a C$_{1-3}$-alkylcarbonylamino, N—(C$_{1-13}$-alkyl)-C$_{1-3}$-alkylcarbonylamino, aminocarbonyl, C$_{1-3}$-alkylaminocarbonyl or di-(C$_{1-3}$-alkyl)-aminocarbonyl group, or R$_6$ denotes a group of formula

$$-N(R_a)-CO-(CH_2)_n-R_b \qquad (II),$$

wherein

R$_a$ denotes a C$_{1-3}$-alkyl group, n one of the numbers 0, 1 or 2 and

R$_b$ denotes an amino, C$_{1-4}$-alkylamino, phenylamino, N—(C 14-alkyl)-phenylamino, benzylamino, N—(C$_{1-4}$-alkyl)-benzylamino or di-(C$_{1-4}$-alkyl)-amino group or a 4- to 7-membered cycloalkyleneimino group, wherein in each case the methylene group in the 4 position of a 6- or 7-membered cycloalkyleneimino group is optionally replaced by an oxygen or sulphur atom, by a sulphinyl, sulphonyl, —NH or —N(C$_{1-3}$-alkyl) group, a group of formula

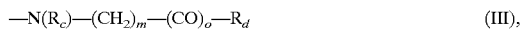

$$-N(R_c)-(CH_2)_m-(CO)_o-R_d \qquad (III),$$

wherein

R$_c$ denotes a C$_{1-3}$-alkyl, C$_{1-3}$-alkylcarbonyl, arylcarbonyl, benzylcarbonyl, C$_{1-3}$-alkylsulphonyl, arylsulphonyl or benzylsulphonyl group, m denotes one of the numbers 1, 2, 3 or 4, o denotes one of the numbers 0 or 1 and $R_d$ has the meanings given for $R_b$ hereinbefore or denotes a di-($C_{1-4}$-alkyl)-amino-$C_{1-3}$-alkylamino group optionally substituted in the 1 position by a $C_{1-3}$-alkyl group, or $R_6$ denotes an N—($C_{1-3}$-alkyl)-$C_{1-3}$-alkylsulphonylamino group;

or the physiologically acceptable salts and isomers thereof.

2. The compound according to claim 1, wherein

X denotes an oxygen atom;

$R_1$ denotes a $C_{1-3}$-alkoxy, trifluoromethyl, di-($C_{1-3}$-alkyl)-amino, pyrrolidino or pyrrolo group,
    an amino or $C_{1-3}$-alkylamino group wherein an amino-hydrogen atom is optionally replaced by a $C_{1-3}$-alkylcarbonyl, phenyl-$C_{1-3}$-alkylcarbonyl, benzoyl, aminocarbonyl, $C_{1-3}$-alkylsulphonyl, phenylsulphonyl, carboxy-$C_{1-3}$-alkyl or $C_{1-3}$-alkyloxycarbonyl-$C_{1-3}$-alkyl group, or
    a phenyl group optionally substituted by a $C_{1-3}$-alkyl group;

$R_2$ denotes a hydrogen atom or a $C_{1-3}$-alkoxy group or $R_1$ and $R_2$ together denote a methylenedioxy group;

$R_4$ denotes a hydrogen atom;

$R_5$ denotes a hydrogen atom and $R_6$ denotes a hydrogen, fluorine, chlorine, bromine or iodine atom,
    a trifluoromethyl, 4-($C_{1-3}$-alkyl)-piperazino, pyridinyl, imidazolyl, tetrazolyl, $C_{1-3}$-alkoxy or $C_{1-3}$-alkylmercapto group,
    a nitro, cyano, carboxy or $C_{1-3}$-alkyloxycarbonyl group or a $C_{1-3}$-alkylcarbonylamino group optionally substituted at the nitrogen atom by a $C_{1-3}$-alkyl group,
    a piperidinocarbonyl group or an aminocarbonyl group optionally substituted by one or two $C_{1-3}$-alkyl groups,
    a $C_{1-3}$-alkyl group optionally terminally substituted
        by an amino, $C_{1-4}$-alkylamino, di-($C_{1-4}$-alkyl)-amino, phenylamino, N-phenyl-$C_{1-3}$-alkylamino, phenyl-n-$C_{1-3}$-alkylamino, N—($C_{1-3}$-alkyl)-phenyl-n-$C_{1-3}$-alkylamino or di-phenyl-n-$C_{1-3}$-alkyl)-amino group,
        by a pyrrolidino, piperidino, hexamethyleneimino, morpholino, thiomorpholino, 1-oxido-thiomorpholino or piperazino group wherein the piperidino group may additionally be substituted by one or two $C_{1-3}$-alkyl groups or by a carboxy, $C_{1-3}$-alkoxycarbonyl, aminocarbonyl, $C_{1-3}$-alkylaminocarbonyl-di-($C_{1-3}$-alkyl)-aminocarbonyl or N—($C_{1-3}$-alkyl)-phenyl-n-$C_{1-3}$-alkylamino group,
        by a $C_{5-7}$-cycloalkylamino or $C_{5-7}$-cycloalkenylamino group wherein position 1 of the ring is not involved in the double bond,
        by a $C_{1-3}$-alkylcarbonylamino, N—($C_{1-3}$-alkyl)-$C_{1-3}$-alkylcarbonylamino, carboxy, $C_{1-3}$-alkoxycarbonyl, aminocarbonyl, $C_{1-3}$-alkylaminocarbonyl or di-($C_{1-3}$-alkyl)-aminocarbonyl group, a $C_{1-3}$-alkoxy group, which is terminally substituted by an amino, $C_{1-3}$-alkylamino or di-($C_{1-3}$-alkyl)-amino group, a group of formula $$-N(R_a)-CO-(CH_2)_n-R_b \quad (II),$$

wherein $R_a$ denotes a $C_{1-3}$-alkyl group, n denotes one of the numbers 0, 1 or 2 and $R_b$ denotes an amino, $C_{1-4}$-alkylamino or di-($C_{1-4}$-alkyl)-amino group or a pyrrolidino, piperidino, hexamethyleneimino, morpholino, thiomorpholino, 1-oxido-thiomorpholino or piperazino group, a group of formula

$$-N(R_c)-(CH_2)_m-(CO)_o-R_d \quad (III),$$

wherein $R_c$ denotes a $C_{1-3}$-alkyl, $C_{1-3}$-alkylcarbonyl or $C_{1-3}$-alkylsulphonyl group, m denotes one of the numbers 1, 2, 3 or 4, o denotes one of the numbers 0 or 1 and $R_d$ has the meanings given for $R_b$ hereinbefore or denotes a di-($C_{1-4}$-alkyl)-amino-$C_{1-3}$-alkylamino group optionally substituted in the 1 position by a $C_{1-3}$-alkyl group, or $R_6$ denotes an N—($C_{1-3}$-alkyl)-$C_{1-3}$-alkylsulphonylamino group.

3. The compound according to claim 1, wherein

X denotes an oxygen atom;

$R_1$ denotes a methoxy, ethoxy, trifuoromethyl, phenyl, methylphenyl, dimethylamino, pyrrolidino or pyrrolo group,
    an amino group which is optionally substituted by a methyl, carboxymethyl, methoxycarbonylmethyl, acetyl, phenylacetyl, benzoyl, methanesulphonyl, benzenesulphonyl or aminocarbonyl group;

$R_2$ denotes a hydrogen atom, a methoxy or ethoxy group or $R_1$ and $R_2$ together denote a methylenedioxy group;

$R_4$ denotes a hydrogen atom;

$R_5$ denotes a hydrogen atom and $R_6$ denotes a hydrogen, fluorine, chlorine, bromine or iodine atom,
    a methyl, trifluoromethyl, methoxy, ethoxy, methylmercapto, cyano, carboxy, methoxycarbonyl, ethoxycarbonyl, aminocarbonyl, dimethylaminocarbonyl, piperidinocarbonyl, nitro, 4-methyl-piperazino, imidazolyl, pyridinyl or tetrazolyl group,
    an ethyloxy or n-propyloxy group terminally substituted by a dimethylamino group,
    a methyl or ethyl group substituted by a carboxy, methoxycarbonyl, ethoxycarbonyl, aminocarbonyl or dimethylaminocarbonyl group, a $C_{1-3}$-alkyl group, which is optionally terminally substituted
    by an amino, $C_{1-4}$-alkylamino, cyclohexylamino, benzylamino or phenylamino group wherein a hydrogen atom of the amino-nitrogen atom is optionally replaced in each case by a $C_{1-3}$-alkyl, benzyl, acetyl or dimethylaminocarbonyl group,
    by a piperidino group optionally substituted by one or two methyl groups,
    by a piperidino group substituted by a carboxy, methoxycarbonyl, ethoxycarbonyl or dimethylaminocarbonyl group,
    by a pyrrolidino, 3,4-dehydro-piperidino, hexamethyleneimino, morpholino, thiomorpholino, 1-oxo-thiomorpholino or piperazino group, a $C_{1-3}$-alkylamino group wherein the hydrogen atom of the amino-nitrogen atom is replaced
    by an ethyl or n-propyl group, each of which is terminally substituted by a dimethylamino group, by a $C_{2-3}$-alkanoyl group which is optionally substituted in the 2 or 3 position by an amino, $C_{1-3}$-alkylamino, di-($C_{1-3}$-alkyl)-amino, pyrrolidino, piperidino, morpholino or piperazino group, by an aminocarbonyl, methylaminocarbonyl, dimethylaminocarbonyl, piperidinocarbonyl or methanesulphonyl group, wherein the $C_{1-3}$-alkyl moiety of the $C_{1-3}$-alkylamino group is further optionally substituted by an aminocarbonyl group, by a $C_{1-3}$-alkylaminocarbonyl or di-($C_{1-3}$-alkyl)-aminocarbonyl group wherein a $C_{2-3}$-alkyl moiety may additionally be terminally substituted by a dimethylamino group, by a pyrrolidinocarbonyl, piperidinocarbonyl, morpholinocarbonyl or piperazinocarbonyl group, and wherein the $C_{2-3}$-alkyl moiety of the abovementioned $C_{1-3}$-alkylamino group is also further optionally terminally substituted by an amino, $C_{1-3}$-alkylamino, di-($C_{1-3}$-alkyl)-amino, pyrrolidino, piperidino, morpholino or piperazino group.

4. The compound according to claim 3,
wherein
$R_2$ denotes a hydrogen atom.

5. The compound according to claim 2,
wherein
$R_1$ and $R_2$, which are identical or different, each denote a $C_{1-3}$-alkoxy group.

6. The compound according to claim 1, wherein
X denotes an oxygen atom;
$R_1$ denotes an amino, methoxy or ethoxy group;
$R_2$ denotes a hydrogen atom or in position 5 a methoxy or ethoxy group;
$R_4$ and $R_5$ each denote a hydrogen atom and
$R_6$ denotes a methyl or ethyl group substituted by a methylamino, ethylamino, piperidino or 4-(dimethylaminocarbonyl)-piperidino group, wherein the amino-hydrogen atom of the methylamino- and ethylamino group is replaced by a methyl or benzyl group, an N-dimethylaminomethylcarbonyl-N-methyl-amino group or an N-acetyl-N—($C_{2-3}$-alkyl)-amino group wherein the $C_{2-3}$-alkyl moiety in each case is terminally substituted by a dimethylamino group.

7. A compound chosen from (a) 3-(Z)-{1-[4-(piperidin-1-yl-methyl)-anilino]-1-phenyl-methylidene}-5,6-dimethoxy-2-indolinone, (b) 3-(Z)-(1-{4-[(N-benzyl-N-methyl-amino)-methyl]-anilino}-1-phenyl-methylidene)-5,6-dimethoxy-2-indolinone, (c) 3-(Z)-{1-(4-(dimethylamino-methyl)-anilino]-1-phenyl-methylidene}-5,6-dimethoxy-2-indolinone, (d) 3-(Z)-{1-[4-(N-dimethylaminomethylcarbonyl-N-methyl-amino)-anilino]-1-phenyl-methylidene}-5,6-dimethoxy-2-indolinone, (e) 3-(Z)-(1-{4-[2-(4-dimethylcarboxamide-piperidin-1-yl)-ethyl]-anilino}-1-phenyl-methylidene)-5,6-dimethoxy-2-indolinone, (g) 6-amino-3-(Z)-{1-[4-(piperidin-1-yl-methyl)-anilino]-1-phenyl-methylidene}-2-indolinone, (h) 3-(Z)-(1-{4-[N-acetyl-N-(2-dimethylamino-ethyl)-amino]-anilino}-1-phenyl-methylidene)-5,6-dimethoxy-2-indolinone and (i) 3-(Z)-(1-{4-[N-acetyl-N-(3-dimethylamino-propyl)-amino]-anilino}-1-phenyl-methylidene)-5,6-dimethoxy-2-indolinone or the physiologically acceptable salts and isomers thereof.

8. A pharmaceutical composition comprising a therapeutically effective amount of a compound according to claim 1 and one or more inert carriers and/or diluents.

* * * * *